(12) United States Patent
Bhide et al.

(10) Patent No.: US 10,023,576 B2
(45) Date of Patent: Jul. 17, 2018

(54) HETEROARYL SUBSTITUTED PYRROLOTRIAZINE AMINE COMPOUNDS AS PI3K INHIBITORS

(71) Applicant: BRISTOL-MYERS SQUIBB COMPANY, Princeton, NJ (US)

(72) Inventors: Rajeev S. Bhide, Bangalore (IN); Zheming Ruan, Dayton, NJ (US); Robert J. Cherney, Newtown, PA (US); Lyndon A. M. Cornelius, Jackson, NJ (US); T. G. Murali Dhar, Newtown, PA (US); Hua Gong, King of Prussia, PA (US); David Marcoux, Pennington, NJ (US); Michael A. Poss, Lawrenceville, NJ (US); Lan-ying Qin, Plainsboro, NJ (US); Qing Shi, Princeton, NJ (US); Joseph A. Tino, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/521,199

(22) PCT Filed: Oct. 21, 2015

(86) PCT No.: PCT/US2015/056577
§ 371 (c)(1),
(2) Date: Apr. 21, 2017

(87) PCT Pub. No.: WO2016/064958
PCT Pub. Date: Apr. 28, 2016

(65) Prior Publication Data
US 2017/0355698 A1 Dec. 14, 2017

Related U.S. Application Data

(60) Provisional application No. 62/067,092, filed on Oct. 22, 2014.

(51) Int. Cl.
C07D 487/04 (2006.01)
(52) U.S. Cl.
CPC .................. *C07D 487/04* (2013.01)
(58) Field of Classification Search
CPC ................................................. C07D 253/065
See application file for complete search history.

(56) References Cited

U.S. PATENT DOCUMENTS

| 8,084,620 B2 | 12/2011 | Liu et al. |
| 9,447,101 B2 | 9/2016 | Yang et al. |
| 2007/0112005 A1 | 5/2007 | Chen et al. |
| 2011/0044942 A1 | 2/2011 | Puri et al. |
| 2012/0009147 A1 | 1/2012 | Cho et al. |

FOREIGN PATENT DOCUMENTS

| WO | WO 2005/097052 | 10/2005 | |
| WO | WO 2005/113556 | 12/2005 | |
| WO | WO 2007/056170 | * 5/2007 | ............. A61K 31/53 |
| WO | WO 2007/061882 | 5/2007 | |
| WO | WO 2007/064883 | 6/2007 | |
| WO | WO 2007/064931 | 6/2007 | |
| WO | WO 2007/079164 | 7/2007 | |
| WO | WO 2007/087395 | 8/2007 | |
| WO | WO 2008/089105 | 7/2008 | |
| WO | WO 2009/117482 | 9/2009 | |
| WO | WO 2009/136966 | 11/2009 | |
| WO | WO 2010/051042 | 5/2010 | |
| WO | WO 2010/051043 | 5/2010 | |
| WO | WO 2010/126960 | 11/2010 | |
| WO | WO 2011/011550 | 1/2011 | |
| WO | WO 2011/014726 | 2/2011 | |

(Continued)

OTHER PUBLICATIONS

International Search Report Application No. PCT/US2015/056577 dated Jan. 18, 2016.
Vanhaesebroeck et al., "The emerging mechanisms of isoform-specific PI3K signaling," Nature Review, Mol. Cell Biol. vol. 11, pp. 329-341 (2010).
Vanhaesebroeck et al., "PI3K signaling: the path to discovery and understandings," Nature Review. Mol. Cell Biol. vol. 13, pp. 195-203 (2012).
Ali et al., "Inactivation of PI92)K p110δ breaks regulatory T-cell-mediated immune tolerance to cancer," Nature, vol. 510, pp. 407-411 (2014).
Lu et al., "Suppression of Phosphoinositide 3-Kinase Signaling and Alteration of Multiple Ion Currents in Drug-Induced Long QT Syndrome," Science Translational Medicine, vol. 4, Issue 131 ra150, pp. 1-10 (2012).
Maxwell et al., "Attenuation of phosphoinositide 3-kinase δ signaling restrains autoimmune disease," Journal of Autoimmunity, 38, pp. 381-391 (2012).

*Primary Examiner* — Erich A Leeser
(74) *Attorney, Agent, or Firm* — Gary Greenblatt

(57) ABSTRACT

Disclosed are compounds of Formula (I); or a salt thereof; wherein Qi is (i) Cl, Br, I, —CN, —CH₃, or —CF₃; or (ii) pyrazole, triazole, or pyridinyl, each substituted with R₁; Q₂ is pyridinyl, indazolyl, isoquinolinyl, or benzo[d]imidazolyl substituted with R₂ and R₃; and R₁, R₂, and R₃ are defined herein. Also disclosed are methods of using such compounds as modulators of PI3K, and pharmaceutical compositions comprising such compounds. These compounds are useful in treating, preventing, or slowing inflammatory and autoimmune diseases.

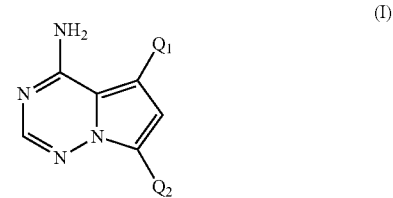

(I)

10 Claims, No Drawings

(56) References Cited

FOREIGN PATENT DOCUMENTS

| | | |
|---|---|---|
| WO | WO 2011/123493 | 10/2011 |
| WO | WO 2011/159857 | 12/2011 |
| WO | WO 2012/007493 | 1/2012 |
| WO | WO 2012/148540 | 11/2012 |
| WO | WO 2012/151562 | 11/2012 |
| WO | WO 2013/004551 | 1/2013 |
| WO | WO 2013/028263 | 2/2013 |
| WO | WO 2013/095761 | 6/2013 |
| WO | WO 2013/104610 | 7/2013 |
| WO | WO 2013/104611 | 7/2013 |
| WO | WO 2013/124316 | 8/2013 |
| WO | WO 2013/124826 | 8/2013 |
| WO | WO 2014/011568 | 1/2014 |
| WO | WO 2014/033196 | 3/2014 |
| WO | WO 2015/058084 | 4/2015 |
| WO | WO 2016/064957 | 4/2016 |
| WO | WO 2007/056170 | 5/2017 |

\* cited by examiner

HETEROARYL SUBSTITUTED PYRROLOTRIAZINE AMINE COMPOUNDS AS PI3K INHIBITORS

CROSS-REFERENCE TO RELATED APPLICATIONS

This application is a national phase application under 35 U.S.C. § 371 of International Patent Application No. PCT/US2015/056577, filed Oct. 21, 2015, which claims priority to U.S. Provisional Application 62/067,092, filed Oct. 22, 2014, which are expressly incorporated fully herein by reference.

DESCRIPTION

The present invention generally relates to heteroaryl substituted pyrrolotriazine amine compounds useful as kinase inhibitors, including the modulation of phosphoinositide 3-kinases (PI3Ks). Provided herein are heteroaryl substituted pyrrolotriazine amine compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including PI3K.

Phosphoinositide 3-kinases are lipid kinases that phosphorylate the 3-OH position of the inositol ring of membrane-based phosphoinositol substrates, i.e., phosphoinositol (PI), phosphatidylinositol-4-phosphate (PIP) and phosphatidylinositol-4,5-bisphosphate (PI-4,5-P2). The resulting 3-phosphate inositides are homing sites for signaling proteins that bind via their lipid-binding domains (Vanhaesebroeck, B. et al., *Nature Rev. Mol. Cell Biol.*, 11:329-341 (2010)). PI3Ks have been divided into 3 classes based on sequence homology and substrate specificity. Class I converts PI-4,5-P2 to PI-3,4,5 trisphosphate (PIP3); Class II converts PI-4-P to PI-3,4-P2 and PI to PI-3-P; and Class III converts PI into PI-3-P. Class I enzymes are the most extensively studied. Their activity generates PIP3 that forms a docking site for proteins with pleckstrin homology domains. These proteins are upstream components of multiple signaling pathways. (Vanhaesebroeck, B. et al., *Nature Rev. Mol. Cell Biol.*, 13:195-203 (2012)).

Class I PI3Ks are subdivided into Class IA and IB. In both subclasses, the enzymes are heterodimers consisting of a catalytic subunit and a regulatory subunit (Vanhaesebroeck, B. et al., *Nature Rev. Mol. Cell Biol.*, 11:329-341 (2010)). In Class IA, the catalytic subunits are p110α, β, and δ. Each associates with a regulatory subunit of which the most common is p85α, but others have also been identified (p85β, p55α, p55γ, p50α). The p85α regulatory subunit contains two SH2 domains that bind tyrosine phosphorylated following activation of tyrosine kinase receptors. Binding relieves the baseline inhibition that the regulatory subunit exercises on the catalytic subunit. In Class IB, the catalytic subunit p110γ is associated with regulatory subunits p101 or p87. This isoform is activated by the γ,β subunits of G protein-coupled receptors, a pathway that can also be utilized by the other isoforms including PI3kδ.

Class I PI3K isoforms a and 13 are ubiquitously expressed and mediate a large variety of functions in multiple cell types. They have critical roles in development such that homozygous deletion of each of the genes in mice is embryonic lethal (Vanhaesebroeck, B. et al., *Trends Biochem. Sci.*, 30:194-204 (2005)). These isoforms control important metabolic pathways including insulin-dependent glucose uptake (Shepherd, P. R., *Acta Physiol. Scand.*, 183:3-12 (2005)). In addition, PI3Kα protects against myocardial infarction (Lin, R. C. Y. et al., *Arterioscler. Thromb. Vasc. Biol.*, 30:724-732 (2010)) and its inhibition can elicit ion channel perturbation that manifests as QT prolongation (Lu, Z. et al., *Science Trans. Med.*, 4:131ra150 (2012)). PI3Kγ is also expressed within the cardiovascular system and mediates effects on blood pressure (Carnevale, D. et al., *Cardiovasc. Res.*, 93:200-209 (2012)). Its principal expression is on leukocytes, however. PI3Kδ is also expressed mainly on leukocytes. Both PI3Kγ and δ isoforms mediate a large number of functions associated with immune cell activation and survival. While gene deletion in mice is not lethal in either case, it results in marked impairment of immune function (Vanhaesebroeck, B. et al., *Trends Biochem. Sci.*, 30:194-204 (2005)). Relative to PI3γ, PI3Kδ plays a more prominent role in B cell development such that PI3Kδ knockout mice exhibit blockade of B cell differentiation. It also mediates BCR signaling, antibody generation and class switching. The PI3Kδ isoform plays an important role in T cell function and survival though the other isoforms also participate (So, L. et al., *Biochem. J.*, 442:465-481 (2012)). The involvement of PI3Kδ in autoimmunity disease has been demonstrated preclinically in mouse and rat models of a variety of autoimmune diseases including rheumatoid arthritis (Puri, K. D. et al., *J. Immunol.*, 182(Suppl. 50):14 (2009)) and systemic lupus erythematosus (SLE) (Maxwell, M. J. et al., *J. Autoimmunity*, 38:381-391 (2012)). In the clinic, PI3Kδ has been found to be activated in peripheral T cells from patients with SLE and tracks with disease severity (Suarez-Fueyo, A. et al., *J. Immunol.*, 187:2376-2385 (2011)). These data suggest that PI3Kδ inhibition holds promise as an effective therapy for the treatment of autoimmune diseases. Furthermore, a consideration of the potential adverse effects of inhibiting the other isoforms point to δ selectivity as the preferred profile.

Thus, inhibition of PI3K activity can be useful for the treatment of allergic disorders and/or autoimmune and/or inflammatory diseases including, but not limited to: systemic lupus erythematosus (SLE), lupus nephritis, rheumatoid arthritis, multiple vasculitides, idiopathic thrombocytopenic purpura (ITP), myasthenia gravis, allergic rhinitis, multiple sclerosis (MS), transplant rejection, membranous nephritis, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

In addition, PI3K has been reported to play a role in controlling B-cell survival in certain B-cell cancers. For example, PI3K has been shown to be important for the survival of non-Hodgkins lymphoma (NHL) and chronic lymphocytic leukemia (CLL) cells. The PI3Kd inhibitor idelalisib has been approved for the treatment of these diseases in the United States. Thus inhibition of PI3K activity can be useful for the treatment of B-cell lymphoma and leukemia, including CLL and NHL.

Furthermore, inactivation of PI3Kδ has been reported to break regulatory T cell mediated immune tolerance to cancer, increasing the immune response leading to tumor regression in animal models (Ali, K. et al., *Nature*, 510:407-411 (2014)). Inhibition of PI3Kd can therefore be useful in the treatment of tumors, particularly those types where there is evidence of inadequate immune response, including but not limited to bladder, breast, colorectal, esophageal, gastric, head and neck, liver, lung, melanoma, ovarian, pancreatic, and prostate cancers, renal cell carcinoma, leukemia and lymphoma. In the treatment of these cancers it is envisaged that the PI3Kd inhibitor may be combined with other treatments that also stimulate immune responses to tumors, including but not limited to anti-CTLA4, anti-PD-1, and anti-PD-L1 antibodies.

In view of the numerous conditions that are contemplated to benefit by treatment involving modulation of protein kinases, it is immediately apparent that new compounds capable of modulating protein kinases such as PI3K and methods of using these compounds should provide substantial therapeutic benefits to a wide variety of patients.

U.S. Pat. No. 8,084,620 and WO 2011/159857 disclose tricyclic carboxamide compounds useful as kinase inhibitors.

There still remains a need for compounds useful as PI3K inhibitors.

Applicants have found potent compounds that have activity as PI3K inhibitors. These compounds are provided to be useful as pharmaceuticals with desirable stability, bioavailability, therapeutic index, and toxicity values that are important to their drugability.

SUMMARY OF THE INVENTION

The present invention provides bicyclic heteroaryl amine compounds, which are useful as inhibitors of PI3K and the treatment of proliferative diseases, allergic diseases, autoimmune diseases and inflammatory diseases, including prodrugs thereof.

The present invention also provides pharmaceutical compositions comprising at least one compound of Formula (I) and a pharmaceutically acceptable carrier.

The present invention also provides a method of inhibiting PI3K activity comprising administering to a mammal in need thereof at least one compound of Formula (I).

The present invention also provides a method for treating allergic disorders and/or autoimmune and/or inflammatory diseases, comprising administering to a mammal in need thereof at least one compound of Formula (I).

The present invention also provides a method for treating proliferative diseases, such as cancer, comprising administering to a mammal in need thereof at least one compound of Formula (I).

The present invention also provides a method of treating a disease or disorder associated with PI3K activity, the method comprising administering to a mammal in need thereof, at least one compound of Formula (I).

The present invention also provides processes and intermediates for making the compounds of Formula (I).

The present invention also provides a compound of Formula (I) for use in therapy.

The present invention also provides the use of the compounds of Formula (I) for the manufacture of a medicament for the treatment or prophylaxis of PI3K related conditions, such as proliferative diseases, allergic diseases, autoimmune diseases and inflammatory diseases.

The present invention also provides the use of the compounds of Formula (I) for the manufacture of a medicament for treatment of cancer.

The compounds of Formula (I) and compositions comprising the compounds of Formula (I) may be used in treating, preventing, or curing various PI3K related conditions. Pharmaceutical compositions comprising these compounds are useful in treating, preventing, or slowing the progression of diseases or disorders in a variety of therapeutic areas, such as proliferative diseases, allergic diseases, autoimmune diseases and inflammatory diseases.

These and other features of the invention will be set forth in expanded form as the disclosure continues.

DETAILED DESCRIPTION

The first aspect of the present invention provides at least one compound of Formula (I):

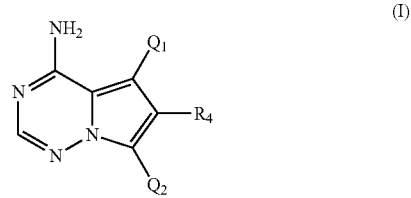

(I)

or a salt thereof; wherein:

$Q_1$ is:
(i) Cl, Br, I, —CN, —CH$_3$, or —CF$_3$; or
(ii) pyrazolyl, triazolyl, or pyridinyl, each substituted with $R_1$;

$R_1$ is $C_{1-3}$ alkyl, $C_{1-3}$ fluoroalkyl, $C_{3-6}$ cycloalkyl, —NHC(O)($C_{1-3}$ alkyl), or tetrahydropyranyl;

$Q_2$ is morpholinyl, piperidinyl, pyridinyl, indazolyl, isoquinolinyl, or benzo[d]imidazolyl, each substituted with $R_2$ and $R_3$;

$R_2$ is H, F, Cl, Br, $C_{1-3}$ alkyl, $C_{1-3}$ fluoroalkyl, —C(O)(pyrrolidinyl), —C(O)NR$_a$R$_a$, —CH$_2$C(O)NR$_a$R$_a$, —C(O)NR$_a$(C$_{4-6}$ cycloalkyl), —C(O)NR$_a$(phenyl), $C_{1-3}$ hydroxy-fluoroalkyl, —CH$_2$(C$_{3-6}$ cycloalkyl), —CH$_2$(C$_{3-6}$ fluorocycloalkyl), =O, R$_x$, or —CH$_2$R$_x$;

$R_x$ is isoxazolyl, pyrrolidinonyl, tetrahydropyranyl, thiopyran 1,1-dioxide, morpholinyl, morpholinonyl, thiomorpholine 1,1-dioxide, pyridinonyl, phenyl, piperazinyl, piperazinonyl, or piperidinyl, each substituted with zero to 5 substituents independently selected from $C_{1-3}$ alkyl, —C(O)NR$_a$R$_a$, —C(O)(C$_{1-3}$ alkyl), —C(O)(C$_{1-3}$ hydroxyalkyl), —C(O)(C$_{3-6}$ cycloalkyl), —C(O)CH$_2$O(C$_{1-3}$ alkyl), —NHC(O)(C$_{1-3}$ alkyl), —S(O)$_2$(C$_{1-3}$ alkyl), and oxetanyl;

$R_3$ is H, F, or —CH$_3$;
$R_4$ is H or F; and
each $R_a$ is independently H or $C_{1-3}$ alkyl.

The second aspect of the present invention provides at least one compound of Formula (I):

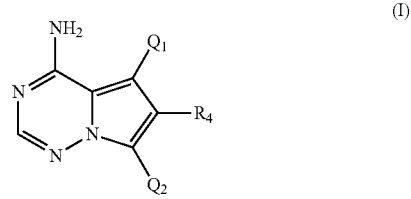

(I)

or a salt thereof; wherein:

$Q_1$ is:
(i) Cl, Br, I, —CN, —CH$_3$, or —CF$_3$; or
(ii) pyrazolyl, triazolyl, or pyridinyl, each substituted with $R_1$;

R₁ is $C_{1-3}$ alkyl, $C_{1-3}$ fluoroalkyl, $C_{3-6}$ cycloalkyl, —NHC(O)($C_{1-3}$ alkyl), or tetrahydropyranyl;

Q₂ is pyridinyl, indazolyl, isoquinolinyl, or benzo[d]imidazolyl, each substituted with R₂ and R₃;

R₂ is H, F, Cl, Br, $C_{1-3}$ alkyl, $C_{1-3}$ fluoroalkyl, —CH₂C(O)NR$_a$R$_a$, $C_{1-3}$ hydroxy-fluoroalkyl, —CH₂($C_{3-6}$ cycloalkyl), —CH₂($C_{3-6}$ fluorocycloalkyl), =O, R$_x$, or —CH₂R$_x$;

R$_x$ is isoxazolyl, pyrrolidinonyl, tetrahydropyranyl, thiopyran 1,1-dioxide, morpholinyl, thiomorpholine 1,1-dioxide, pyridinonyl, phenyl, piperazinyl, piperazinonyl, or piperidinyl, each substituted with zero to 5 substituents independently selected from $C_{1-3}$ alkyl, —C(O)NR$_a$R$_a$, —C(O)($C_{1-3}$ alkyl), —C(O)($C_{1-3}$ hydroxyalkyl), —C(O)($C_{3-6}$ cycloalkyl), —C(O)CH₂O($C_{1-3}$ alkyl), —NHC(O)($C_{1-3}$ alkyl), —S(O)₂($C_{1-3}$ alkyl), and oxetanyl;

R₃ is H, F, or —CH₃;
R₄ is H; and
each R$_a$ is independently H or —CH₃.

One embodiment provides at least one compound of Formula (I) or a salt thereof, wherein:

Q₁ is:
(i) Cl, Br, I, or —CN; or
(ii) pyrazolyl, triazolyl, or pyridinyl, each substituted with R₁;

R₁ is —CH₃, —CH(CH₃)₂, —CH₂CF₃, —CH(CH₃)CF₃, cyclopropyl, cyclohexyl, —NHC(O)CH₃, or tetrahydropyranyl;

Q₂ is pyridinyl, indazolyl, isoquinolinyl, or benzo[d]imidazolyl, each substituted with R₂ and R₃;

R₂ is H, Br, —CH₃, —CH(CH₃)₂, —CH₂CH₂F, —CH₂C(O)N(CH₃)₂, —CH₂CH(OH)CH₂F, —CH₂(cyclopropyl), —CH₂(difluorocyclopropyl), —CH₂(methyl isoxazolyl), —CH₂(pyrrolidinonyl), =O, tetrahydropyranyl, dimethyl tetrahydropyranyl, thiopyran 1,1-dioxide, morpholinyl, thiomorpholine 1,1-dioxide, methyl pyridinonyl, phenyl substituted with —C(O)NH₂, NHC(O)CH₃, or —S(O)₂CH₃; piperazinyl or piperazinonyl, each substituted with zero to 5 substituents independently selected from —CH₃, —C(O)CH₃, —C(O)(cyclopropyl), and oxetanyl; or piperidinyl or piperidinonyl, each substituted with —CH₃, —C(O)CH₃, —C(O)CH₂OH, or —C(O)CH₂OCH₃;

R₃ is H, F, or —CH₃; and
R₄ is H.

One embodiment provides at least one compound of Formula (I) or a salt thereof, wherein Q₁ is pyrazolyl, triazolyl, or pyridinyl, each substituted with R₁; and R₁, R₄, and Q₂ are defined in the first aspect or the second aspect. Included in this embodiment are compounds having the structures of Formula (Ia), Formula (Ib), Formula (Ic), and Formula (Id):

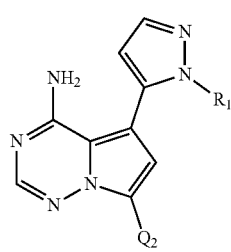

(Ia)

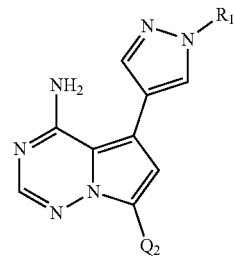

(Ib)

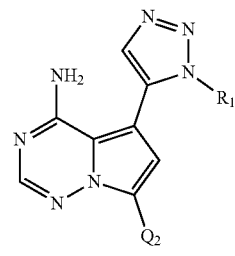

(Ic)

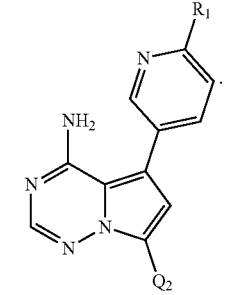

(Id)

One embodiment provides at least one compound of Formula (I) or a salt thereof, wherein Q₁ is pyrazolyl or triazolyl, each substituted with R₁; and R₁, R₄, and Q₂ are defined in the first aspect or the second aspect. Included in this embodiment are the compounds Formula (Ia), Formula (Ib), and Formula (Ic).

One embodiment provides at least one compound of Formula (I) or a salt thereof, wherein Q₁ is pyrazolyl substituted with R₁; and R₁, R₄, and Q₂ are defined in the first aspect or the second aspect. Included in this embodiment are compounds having the structures of Formula (Ia) and Formula (Ib).

One embodiment provides at least one compound of Formula (I) or a salt thereof, wherein Q₁ is triazolyl; and R₁, R₄, and Q₂ are defined in the first aspect or the second aspect. Included in this embodiment are compounds having the structure of Formula (Ic).

One embodiment provides at least one compound of Formula (I) or a salt thereof, wherein Q₁ is pyridinyl substituted with R₁; and R₁, R₄, and Q₂ are defined in the first aspect or the second aspect. Included in this embodiment are compounds having the structure of Formula (Id).

One embodiment provides at least one compound of Formula (I) or a salt thereof, wherein Q₁ is (i) Cl, Br, I, —CN, or —CF₃; or (ii) pyrazolyl or triazolyl, each substituted with R₁; and R₁, R₄, and Q₂ are defined in the first aspect or the second aspect. One embodiment provides at least one compound of Formula (I) or a salt thereof, wherein Q₁ is Cl, Br, I, —CN, —CH₃, or —CF₃; and R₄ and Q₂ are defined in the first aspect or the second aspect.

One embodiment provides at least one compound of Formula (I) or a salt thereof, wherein $Q_1$ is Cl, Br, I, —CN, or —CF$_3$; and $R_4$ and $Q_2$ are defined in the first aspect or the second aspect.

One embodiment provides at least one compound of Formula (I) or a salt thereof, wherein $Q_2$ is pyridinyl substituted with $R_2$ and $R_3$; and $R_2$, $R_3$, $R_4$, and $Q_1$ are defined in the first aspect or the second aspect. Included in this embodiment are compounds having the structures of Formula (IIa) and Formula (IIb):

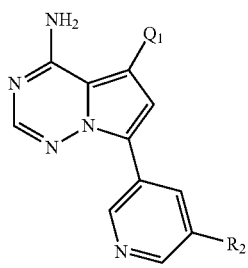

(IIa)

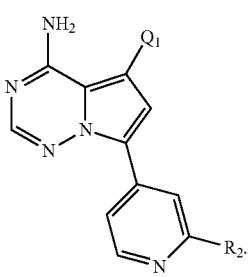

(IIb)

One embodiment provides at least one compound of Formula (I) or a salt thereof, wherein $Q_2$ is indazolyl substituted with $R_2$ and $R_3$; and $R_2$, $R_3$, $R_4$, and $Q_1$ are defined in the first aspect or the second aspect. Included in this embodiment are compounds having the structures of Formula (IIc) and Formula (IId):

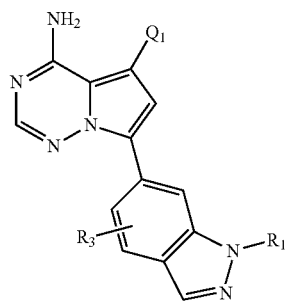

(IIc)

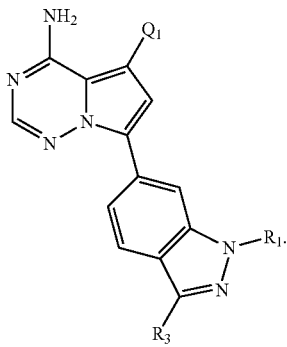

(IId)

One embodiment provides at least one compound of Formula (I) or a salt thereof, wherein $Q_2$ is isoquinolinyl substituted with $R_2$ and $R_3$; and $R_2$, $R_3$, $R_4$, and $Q_1$ are defined in the first aspect or the second aspect. Included in this embodiment are compounds having the structures of Formula (IIe) and Formula (IIf):

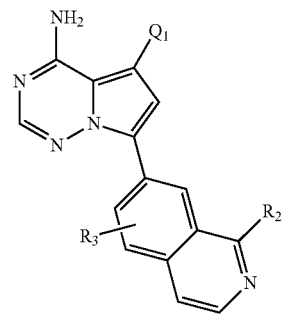

(IIe)

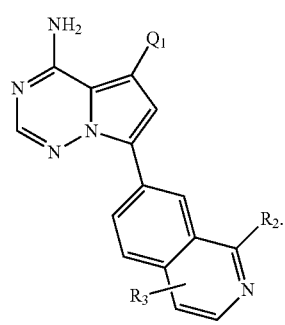

(IIf)

One embodiment provides at least one compound of Formula (I) or a salt thereof, wherein $Q_2$ is benzo[d]imidazolyl substituted with $R_2$ and $R_3$; and $R_2$, $R_3$, $R_4$, and $Q_1$ are defined in the first aspect or the second aspect. Included in this embodiment are compounds having the structures of Formula (IIg) and Formula (IIh):

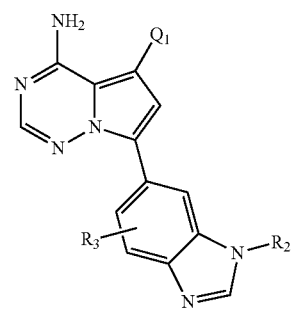
(IIg)
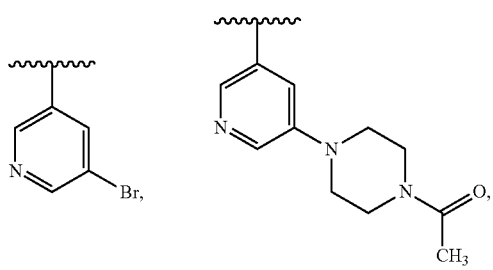
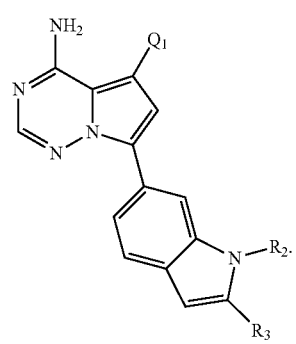
(IIh)
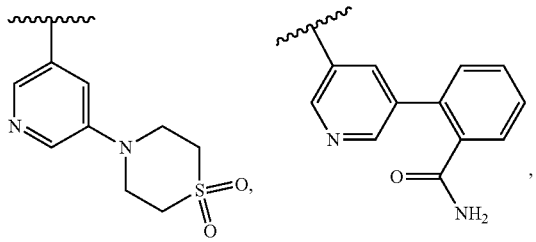
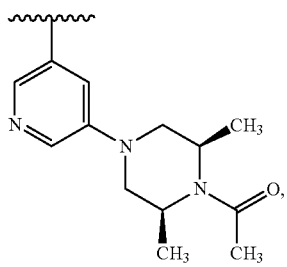
One embodiment provides at least one compound of Formula (I) or a salt thereof, wherein $Q_2$ is:
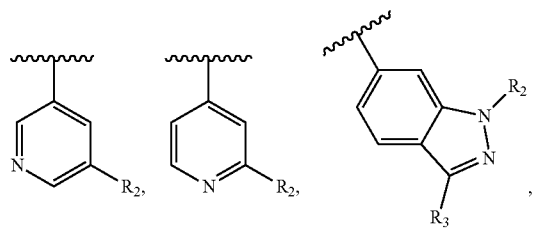
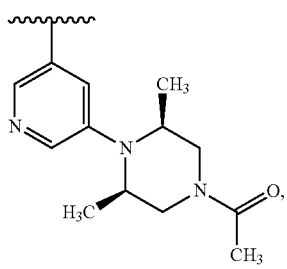
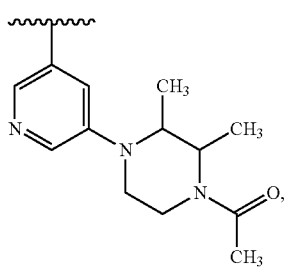
and $Q_1$, $R_2$, $R_3$, and $R_4$ are defined in the first aspect or the second aspect.
One embodiment provides at least one compound of Formula (I) or a salt thereof, wherein $Q_2$ is:
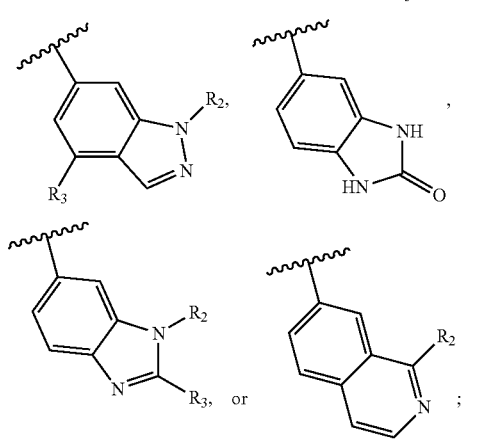
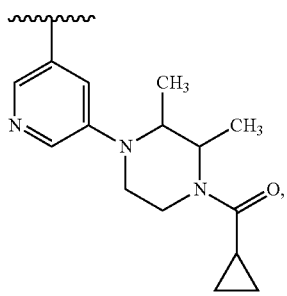

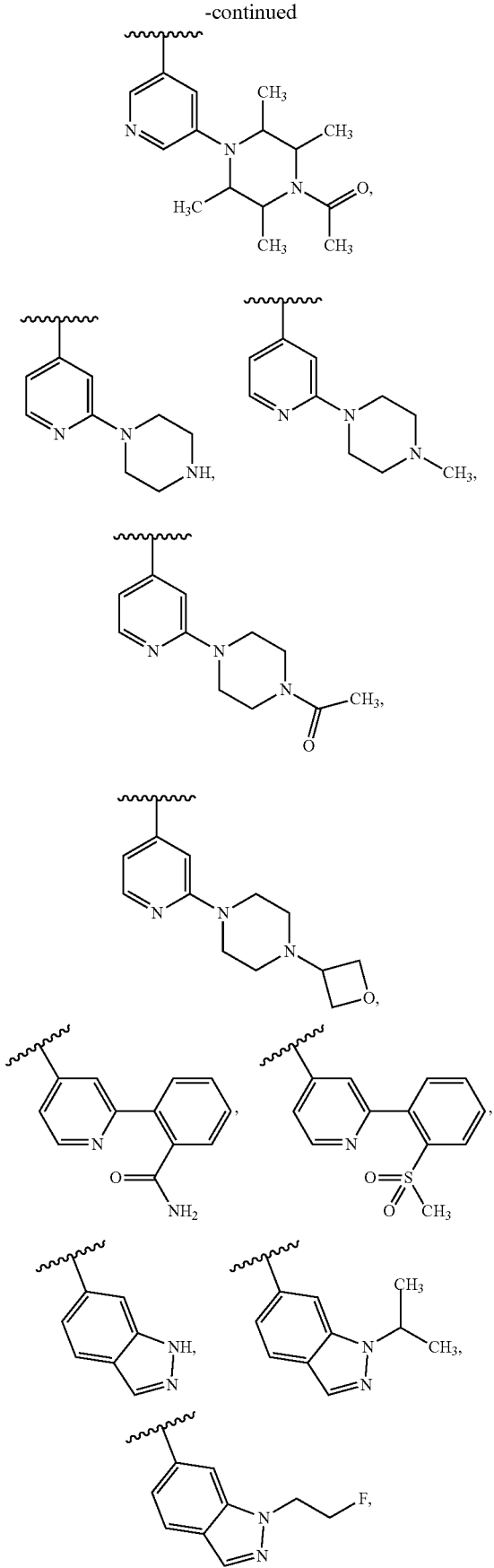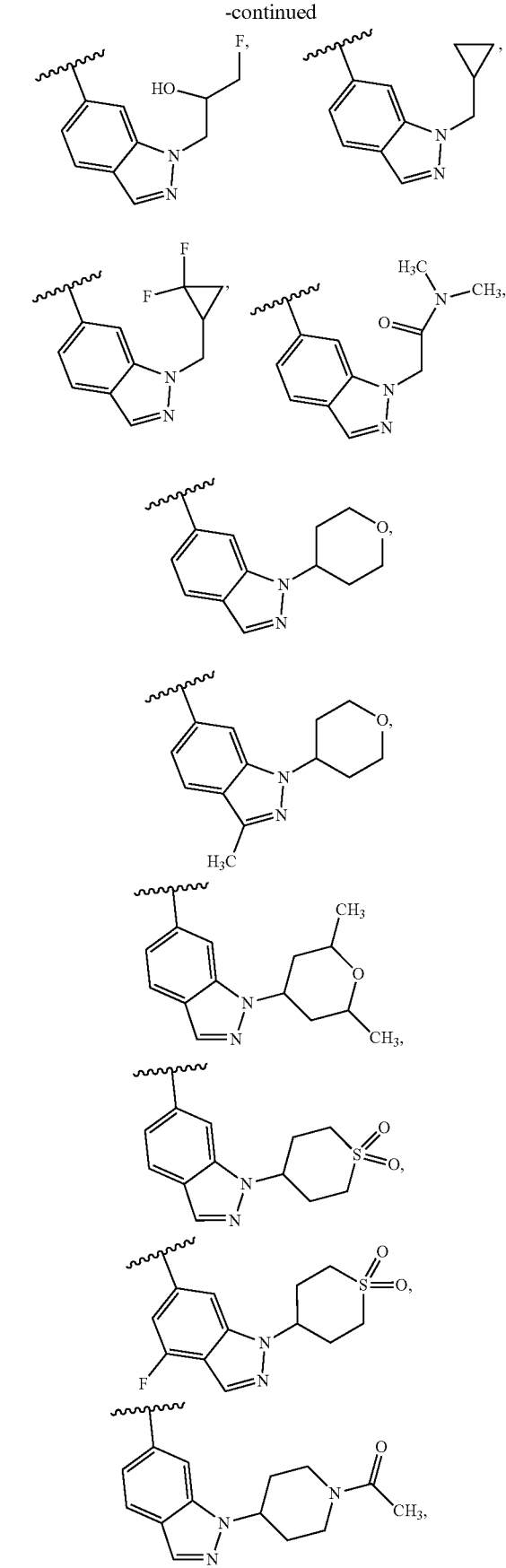

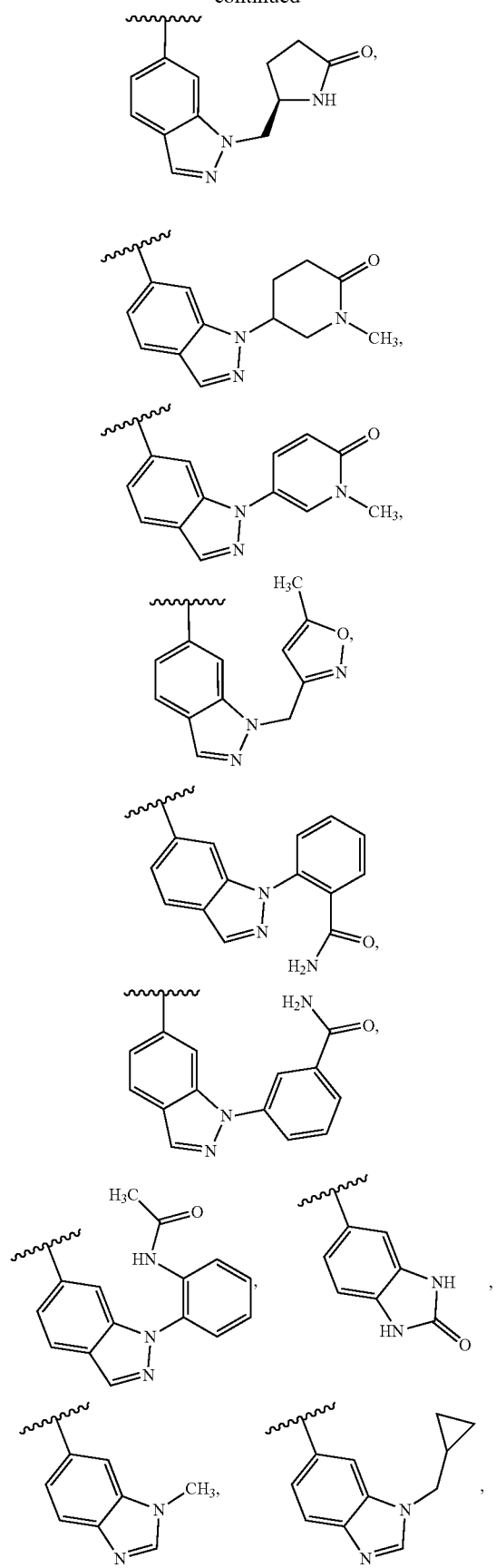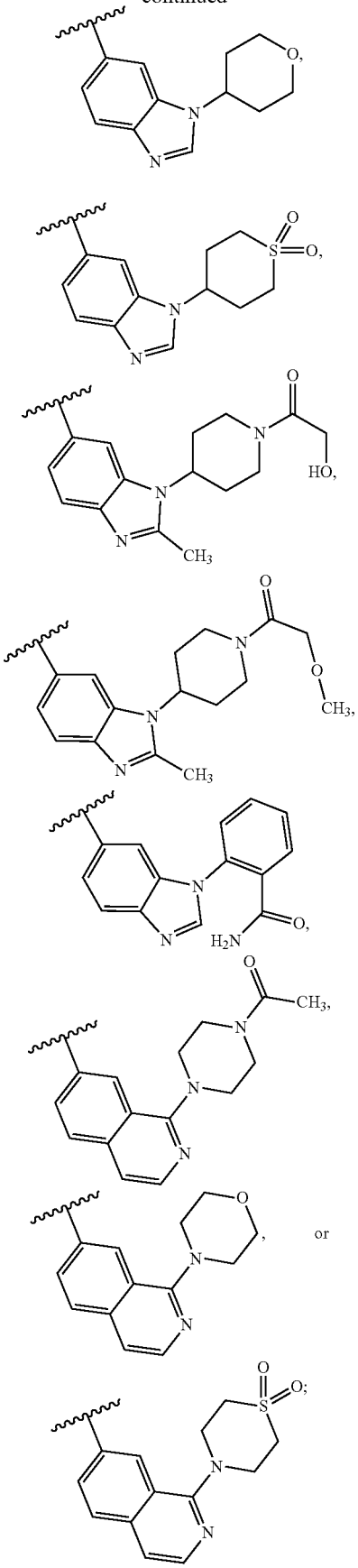

and $Q_1$ and $R_4$ are defined in the first aspect or the second aspect.

One embodiment provides at least one compound of Formula (I) or a salt thereof, wherein:

$Q_1$ is pyrazolyl, triazolyl, or pyridinyl, each substituted with $R_1$;

$R_1$ is —$CH_3$, —$CH(CH_3)_2$, —$CH_2CF_3$, —$CH(CH_3)CF_3$, cyclopropyl, cyclohexyl, —NHC(O)$CH_3$, or tetrahydropyranyl;

$Q_2$ is pyridinyl, indazolyl, isoquinolinyl, or benzo[d]imidazolyl, each substituted with $R_2$ and $R_3$;

$R_2$ is H, Br, —$CH_3$, —$CH(CH_3)_2$, —$CH_2CH_2F$, —$CH_2C(O)N(CH_3)_2$, —$CH_2CH(OH)CH_2F$, —$CH_2$(cyclopropyl), —$CH_2$(difluorocyclopropyl), —$CH_2$(methyl isoxazolyl), —$CH_2$(pyrrolidinonyl), =O, tetrahydropyranyl, dimethyl tetrahydropyranyl, thiopyran 1,1-dioxide, morpholinyl, thiomorpholine 1,1-dioxide, methyl pyridinonyl, phenyl substituted with —C(O)$NH_2$, NHC(O)$CH_3$, or —S(O)$_2CH_3$; piperazinyl or piperazinonyl, each substituted with zero to 5 substituents independently selected from —$CH_3$, —C(O)$CH_3$, —C(O)(cyclopropyl), and oxetanyl; or piperidinyl or piperidinonyl, each substituted with —$CH_3$, —C(O)$CH_3$, —C(O)$CH_2OH$, or —C(O)$CH_2OCH_3$;

$R_3$ is H, F, or —$CH_3$; and
$R_4$ is H.

One embodiment provides at least one compound of Formula (I) or a salt thereof, wherein $Q_1$ is Cl, Br, I, or —CN; and $Q_2$ indazole substituted with tetrahydropyranyl. Included in this embodiment are the compounds having the structure:

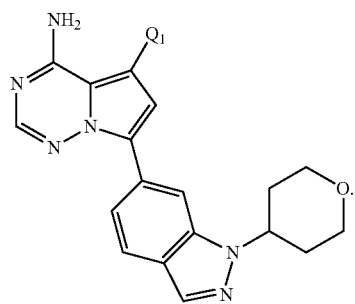

One embodiment provides at least one compound of Formula (I) or a salt thereof, wherein said compound is selected from 1-(4-(5-(4-amino-5-(1-(tetrahydro-2H-pyran-4-yl)-1H-pyrazol-5-yl)pyrrolo[2,1-f][1,2,4]triazin-7-yl)pyridin-3-yl)piperazin-1-yl)ethanone, TFA (1); 5-(4-amino-5-(1-cyclohexyl-1H-pyrazol-5-yl)pyrrolo[2,1-f][1,2,4]triazin-7-yl)-1H-benzo[d]imidazol-2(3H)-one (2); 5-(1-cyclohexyl-1H-pyrazol-5-yl)-7-(1-methyl-1H-benzo[d]imidazol-6-yl)pyrrolo[2,1-f][1,2,4]triazin-4-amine (3); 1-(4-(5-(4-amino-5-(1-(tetrahydro-2H-pyran-4-yl)-1H-1,2,3-triazol-5-yl)pyrrolo[2,1-f][1,2,4]triazin-7-yl)pyridin-3-yl)piperazin-1-yl)ethanone, TFA (4); 1-(4-(5-(4-amino-5-(1-isopropyl-1H-1,2,3-triazol-5-yl)pyrrolo[2,1-f][1,2,4]triazin-7-yl)pyridin-3-yl)piperazin-1-yl)ethanone, TFA (5); 4-(5-(4-amino-5-(1-(tetrahydro-2H-pyran-4-yl)-1H-pyrazol-5-yl)pyrrolo[2,1-f][1,2,4]triazin-7-yl)pyridin-3-yl)thiomorpholine 1,1-dioxide (6); 4-(5-(4-amino-5-(1-(tetrahydro-2H-pyran-4-yl)-1H-1,2,3-triazol-5-yl)pyrrolo[2,1-f][1,2,4]triazin-7-yl)pyridin-3-yl)thiomorpholine 1,1-dioxide (7); 4-(5-(4-amino-5-(1-isopropyl-1H-1,2,3-triazol-5-yl)pyrrolo[2,1-f][1,2,4]triazin-7-yl)pyridin-3-yl)thiomorpholine 1,1-dioxide (8); 1-((cis)-4-(5-(4-amino-5-(1-(tetrahydro-2H-pyran-4-yl)-1H-pyrazol-5-yl)pyrrolo[2,1-f][1,2,4]triazin-7-yl)pyridin-3-yl)-2,6-dimethylpiperazin-1-yl)ethanone (9); 1-((cis)-4-(5-(4-amino-5-(1-(tetrahydro-2H-pyran-4-yl)-1H-1,2,3-triazol-5-yl)pyrrolo[2,1-f][1,2,4]triazin-7-yl)pyridin-3-yl)-2,6-dimethylpiperazin-1-yl)ethanone (10); 1-((cis)-4-(5-(4-amino-5-(1-(tetrahydro-2H-pyran-4-yl)-1H-pyrazol-5-yl)pyrrolo[2,1-f][1,2,4]triazin-7-yl)pyridin-3-yl)-3,5-dimethylpiperazin-1-yl)ethanone (11); 1-((cis)-4-(5-(4-amino-5-(1-(tetrahydro-2H-pyran-4-yl)-1H-1,2,3-triazol-5-yl)pyrrolo[2,1-f][1,2,4]triazin-7-yl)pyridin-3-yl)-3,5-dimethylpiperazin-1-yl)ethanone (12); 1-((cis)-4-(5-(4-amino-5-(1-isopropyl-1H-1,2,3-triazol-5-yl)pyrrolo[2,1-f][1,2,4]triazin-7-yl)pyridin-3-yl)-3,5-dimethylpiperazin-1-yl)ethanone (13); 1-(4-(5-(4-amino-5-(1-(tetrahydro-2H-pyran-4-yl)-1H-pyrazol-5-yl)pyrrolo[2,1-f][1,2,4]triazin-7-yl)pyridin-3-yl)-2,3,5,6-tetramethylpiperazin-1-yl)ethanone (14); 1-(4-(5-(4-amino-5-(1-(tetrahydro-2H-pyran-4-yl)-1H-1,2,3-triazol-5-yl)pyrrolo[2,1-f][1,2,4]triazin-7-yl)pyridin-3-yl)-2,3,5,6-tetramethylpiperazin-1-yl)ethanone (15); 7-(1-(tetrahydro-2H-pyran-4-yl)-1H-indazol-6-yl)-5-(1-(tetrahydro-2H-pyran-4-yl)-1H-pyrazol-5-yl)pyrrolo[2,1-f][1,2,4]triazin-4-amine (16); 7-(1-(2-fluoroethyl)-1H-indazol-6-yl)-5-(1-(tetrahydro-2H-pyran-4-yl)-1H-pyrazol-5-yl)pyrrolo[2,1-f][1,2,4]triazin-4-amine (17); 5-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)-1-methylpyridin-2(1H)-one (18); 5-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)-1-methylpiperidin-2-one (19); 1-(4-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)piperidin-1-yl)ethanone (20); 1-(4-(6-(4-amino-5-(1-(tetrahydro-2H-pyran-4-yl)-1H-1,2,3-triazol-5-yl)pyrrolo[2,1-f][1,2,4]triazin-7-yl)-1H-indazol-1-yl)piperidin-1-yl)ethanone (21); 1-(4-(6-(4-amino-5-(1-(tetrahydro-2H-pyran-4-yl)-1H-pyrazol-5-yl)pyrrolo[2,1-f][1,2,4]triazin-7-yl)-2-methyl-1H-benzo[d]imidazol-1-yl)piperidin-1-yl)-2-hydroxyethanone (22); 1-(4-(6-(4-amino-5-(1-(tetrahydro-2H-pyran-4-yl)-1H-pyrazol-5-yl)pyrrolo[2,1-f][1,2,4]triazin-7-yl)-2-methyl-1H-benzo[d]imidazol-1-yl)piperidin-1-yl)-2-methoxyethanone (23); 5-(1-(tetrahydro-2H-pyran-4-yl)-1H-1,2,3-triazol-5-yl)-7-(1-(tetrahydro-2H-pyran-4-yl)-1H-indazol-6-yl)pyrrolo[2,1-f][1,2,4]triazin-4-amine (24); 5-(1-isopropyl-1H-1,2,3-triazol-5-yl)-7-(1-(tetrahydro-2H-pyran-4-yl)-1H-indazol-6-yl)pyrrolo[2,1-f][1,2,4]triazin-4-amine (25); 5-(1-cyclohexyl-1H-1,2,3-triazol-5-yl)-7-(1-(tetrahydro-2H-pyran-4-yl)-1H-indazol-6-yl)pyrrolo[2,1-f][1,2,4]triazin-4-amine (26); 7-(1-(2,6-dimethyltetrahydro-2H-pyran-4-yl)-1H-indazol-6-yl)-5-(1-(tetrahydro-2H-pyran-4-yl)-1H-pyrazol-5-yl)pyrrolo[2,1-f][1,2,4]triazin-4-amine (27); 7-(3-methyl-1-(tetrahydro-2H-pyran-4-yl)-1H-indazol-6-yl)-5-(1-(tetrahydro-2H-pyran-4-yl)-1H-pyrazol-5-yl)pyrrolo[2,1-f][1,2,4]triazin-4-amine (28); 7-(3-methyl-1-(tetrahydro-2H-pyran-4-yl)-1H-indazol-6-yl)-5-(1-(tetrahydro-2H-pyran-4-yl)-1H-1,2,3-triazol-5-yl)pyrrolo[2,1-f][1,2,4]triazin-4-amine (29); 7-(1-(tetrahydro-2H-pyran-4-yl)-1H-benzo[d]imidazol-6-yl)-5-(1-(tetrahydro-2H-pyran-4-yl)-1H-pyrazol-5-yl)pyrrolo[2,1-f][1,2,4]triazin-4-amine (30); 5-(1-(tetrahydro-2H-pyran-4-yl)-1H-1,2,3-triazol-5-yl)-7-(1-(tetrahydro-2H-pyran-4-yl)-1H-benzo[d]imidazol-6-yl)pyrrolo[2,1-f][1,2,4]triazin-4-amine (31); 5-(1-cyclohexyl-1H-1,2,3-triazol-5-yl)-7-(1-(tetrahydro-2H-pyran-4-yl)-1H-benzo[d]imidazol-6-yl)pyrrolo[2,1-f][1,2,4]triazin-4-amine (32); 4-(6-(4-amino-5-(1-(tetrahydro-2H-pyran-4-yl)-1H-pyrazol-5-yl)pyrrolo[2,1-f][1,2,4]

triazin-7-yl)-1H-indazol-1-yl)tetrahydro-2H-thiopyran 1,1-dioxide (33); 4-(6-(4-amino-5-(1-(2,2,2-trifluoroethyl)-1H-pyrazol-5-yl)pyrrolo[2,1-f][1,2,4]triazin-7-yl)-1H-indazol-1-yl)tetrahydro-2H-thiopyran 1,1-dioxide (34); 4-(6-(4-amino-5-(1-cyclohexyl-1H-1,2,3-triazol-5-yl)pyrrolo[2,1-f][1,2,4]triazin-7-yl)-1H-indazol-1-yl)tetrahydro-2H-thiopyran 1,1-dioxide (35); 4-(6-(4-amino-5-(1-(tetrahydro-2H-pyran-4-yl)-1H-1,2,3-triazol-5-yl)pyrrolo[2,1-f][1,2,4]triazin-7-yl)-4-fluoro-1H-indazol-1-yl)tetrahydro-2H-thiopyran 1,1-dioxide (36); 4-(6-(4-amino-5-(1-(tetrahydro-2H-pyran-4-yl)-1H-pyrazol-5-yl)pyrrolo[2,1-f][1,2,4]triazin-7-yl)-4-fluoro-1H-indazol-1-yl)tetrahydro-2H-thiopyran 1,1-dioxide (37); 4-(6-(4-amino-5-(1-cyclopropyl-1H-pyrazol-5-yl)pyrrolo[2,1-f][1,2,4]triazin-7-yl)-4-fluoro-1H-indazol-1-yl)tetrahydro-2H-thiopyran 1,1-dioxide (38); 4-(6-(4-amino-5-(1-(tetrahydro-2H-pyran-4-yl)-1H-pyrazol-5-yl)pyrrolo[2,1-f][1,2,4]triazin-7-yl)-1H-benzo[d]imidazol-1-yl)tetrahydro-2H-thiopyran 1,1-dioxide (39); 4-(6-(4-amino-5-(1-(tetrahydro-2H-pyran-4-yl)-1H-1,2,3-triazol-5-yl)pyrrolo[2,1-f][1,2,4]triazin-7-yl)-1H-benzo[d]imidazol-1-yl)tetrahydro-2H-thiopyran 1,1-dioxide (40); 4-(6-(4-amino-5-(1-(2,2,2-trifluoroethyl)-1H-pyrazol-5-yl)pyrrolo[2,1-f][1,2,4]triazin-7-yl)-1H-benzo[d]imidazol-1-yl)tetrahydro-2H-thiopyran 1,1-dioxide (41); 7-(1-isopropyl-1H-indazol-6-yl)-5-(1-(tetrahydro-2H-pyran-4-yl)-1H-pyrazol-5-yl)pyrrolo[2,1-f][1,2,4]triazin-4-amine (42); 7-(1-(cyclopropylmethyl)-1H-indazol-6-yl)-5-(1-(tetrahydro-2H-pyran-4-yl)-1H-1,2,3-triazol-5-yl)pyrrolo[2,1-f][1,2,4]triazin-4-amine (43); 7-(1-(cyclopropylmethyl)-1H-indazol-6-yl)-5-(1-(tetrahydro-2H-pyran-4-yl)-1H-pyrazol-5-yl)pyrrolo[2,1-f][1,2,4]triazin-4-amine (44); 7-(1-(cyclopropylmethyl)-1H-benzo[d]imidazol-6-yl)-5-(1-(tetrahydro-2H-pyran-4-yl)-1H-1,2,3-triazol-5-yl)pyrrolo[2,1-f][1,2,4]triazin-4-amine (45); 7-(1-(cyclopropylmethyl)-1H-benzo[d]imidazol-6-yl)-5-(1-(tetrahydro-2H-pyran-4-yl)-1H-pyrazol-5-yl)pyrrolo[2,1-f][1,2,4]triazin-4-amine (46); 7-(1-((2,2-difluorocyclopropyl)methyl)-1H-indazol-6-yl)-5-(1-(tetrahydro-2H-pyran-4-yl)-1H-1,2,3-triazol-5-yl)pyrrolo[2,1-f][1,2,4]triazin-4-amine (47); 7-(1-((2,2-difluorocyclopropyl) methyl)-1H-indazol-6-yl)-5-(1-(tetrahydro-2H-pyran-4-yl)-1H-pyrazol-5-yl)pyrrolo[2,1-f][1,2,4]triazin-4-amine (48); 1-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)-3-fluoropropan-2-ol (49); 1-(6-(4-amino-5-(1-(tetrahydro-2H-pyran-4-yl)-1H-1,2,3-triazol-5-yl)pyrrolo[2,1-f][1,2,4]triazin-7-yl)-1H-indazol-1-yl)-3-fluoropropan-2-ol (50); 2-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)-N,N-dimethylacetamide (51); (R)-5-((6-(4-amino-5-(1-(tetrahydro-2H-pyran-4-yl)-1H-pyrazol-5-yl)pyrrolo[2,1-f][1,2,4]triazin-7-yl)-1H-indazol-1-yl)methyl)pyrrolidin-2-one (52); 7-(1-((5-methylisoxazol-3-yl)methyl)-1H-indazol-6-yl)-5-(1-(tetrahydro-2H-pyran-4-yl)-1H-pyrazol-5-yl)pyrrolo[2,1-f][1,2,4]triazin-4-amine (54); 2-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl) benzamide (55); N-(2-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)phenyl)acetamide (56); 3-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)benzamide (57); 1-(4-(7-(4-amino-5-(1-(tetrahydro-2H-pyran-4-yl)-1H-1,2,3-triazol-5-yl)pyrrolo[2,1-f][1,2,4]triazin-7-yl)isoquinolin-1-yl)piperazin-1-yl)ethanone (58); 7-(1-morpholinoisoquinolin-7-yl)-5-(1-(tetrahydro-2H-pyran-4-yl)-1H-1,2,3-triazol-5-yl)pyrrolo[2,1-f][1,2,4]triazin-4-amine (59); 4-(7-(4-amino-5-(1-isopropyl-1H-1,2,3-triazol-5-yl)pyrrolo[2,1-f][1,2,4]triazin-7-yl)isoquinolin-1-yl)thiomorpholine 1,1-dioxide (60); 4-(7-(4-amino-5-(1-(tetrahydro-2H-pyran-4-yl)-1H-1,2,3-triazol-5-yl)pyrrolo[2,1-f][1,2,4]triazin-7-yl) isoquinolin-1-yl)thiomorpholine 1,1-dioxide (61); 7-(2-(piperazin-1-yl)pyridin-4-yl)-5-(1-(tetrahydro-2H-pyran-4-yl)-1H-pyrazol-5-yl)pyrrolo[2,1-f][1,2,4]triazin-4-amine (62); 7-(2-(4-(oxetan-3-yl)piperazin-1-yl)pyridin-4-yl)-5-(1-(tetrahydro-2H-pyran-4-yl)-1H-pyrazol-5-yl)pyrrolo[2,1-f][1,2,4]triazin-4-amine (63); 7-(2-(4-methylpiperazin-1-yl)pyridin-4-yl)-5-(1-(tetrahydro-2H-pyran-4-yl)-1H-pyrazol-5-yl)pyrrolo[2,1-f][1,2,4]triazin-4-amine (64); 1-(4-(4-(4-amino-5-(1-(tetrahydro-2H-pyran-4-yl)-1H-pyrazol-5-yl)pyrrolo[2,1-f][1,2,4]triazin-7-yl)pyridin-2-yl)piperazin-1-yl)ethanone (65); 2-(4-(4-amino-5-(1-(tetrahydro-2H-pyran-4-yl)-1H-pyrazol-5-yl)pyrrolo[2,1-f][1,2,4]triazin-7-yl)pyridin-2-yl)benzamide (66); 2-(5-(4-amino-5-(1-(tetrahydro-2H-pyran-4-yl)-1H-pyrazol-5-yl)pyrrolo[2,1-f][1,2,4]triazin-7-yl)pyridin-3-yl)benzamide (67); 7-(2-(2-(methylsulfonyl)phenyl)pyridin-4-yl)-5-(1-(tetrahydro-2H-pyran-4-yl)-1H-pyrazol-5-yl)pyrrolo[2,1-f][1,2,4]triazin-4-amine (68); 7-[1-(oxan-4-yl)-1H-indazol-6-yl]-5-[1-(propan-2-yl)-1H-pyrazol-4-yl]pyrrolo[2,1-f][1,2,4]triazin-4-amine (69); 4-(6-{amino-5-[1-(propan-2-yl)-1H-pyrazol-4-yl]pyrrolo[2,1-f][1,2,4]triazin-7-yl}-1H-indazol-1-yl)-1$\lambda^6$-thiane-1,1-dione (70); 5-(1-methyl-1H-pyrazol-4-yl)-7-[1-(oxan-4-yl)-1H-indazol-6-yl]pyrrolo[2,1-f][1,2,4]triazin-4-amine (71); 7-(1H-indazol-6-yl)-5-[1-(oxan-4-yl)-1H-pyrazol-5-yl]pyrrolo[2,1-f][1,2,4]triazin-4-amine (72); 4-{6-[4-amino-5-(1-methyl-1H-pyrazol-4-yl)pyrrolo[2,1-f][1,2,4]triazin-7-yl]-1H-indazol-1-yl}-1$\lambda^6$-thiane-1,1-dione (74); N-(5-{4-amino-7-[1-(oxan-4-yl)-1H-indazol-6-yl]pyrrolo[2,1-f][1,2,4]triazin-5-yl}pyridin-2-yl) acetamide (78); N-(5-{4-amino-7-[1-(1,1-dioxo-1$\lambda^6$-thian-4-yl)-1H-indazol-6-yl]pyrrolo[2,1-f][1,2,4]triazin-5-yl}pyridin-2-yl)acetamide (79); 2-(6-(4-amino-5-(1-(tetrahydro-2H-pyran-4-yl)-1H-pyrazol-5-yl)pyrrolo[2,1-f][1,2,4]triazin-7-yl)-1H-benzo[d]imidazol-1-yl)benzamide (80); 2-(6-(4-amino-5-(1-(tetrahydro-2H-pyran-4-yl)-1H-1,2,3-triazol-5-yl)pyrrolo[2,1-f][1,2,4]triazin-7-yl)-1H-benzo[d]imidazol-1-yl)benzamide (81); 7-(5-bromopyridin-3-yl)-5-[1-(oxan-4-yl)-1H-pyrazol-5-yl]pyrrolo[2,1-f][1,2,4]triazin-4-amine (82); 4-acetyl-1-(5-(4-amino-5-chloropyrrolo[2,1-f][1,2,4]triazin-7-yl)pyridin-3-yl)-3,3-dimethylpiperazin-2-one (83); 4-acetyl-1-(5-(4-amino-5-(1-(tetrahydro-2H-pyran-4-yl)-1H-pyrazol-5-yl)pyrrolo[2,1-f][1,2,4]triazin-7-yl)pyridin-3-yl)-3,3-dimethylpiperazin-2-one (84); (R)-4-acetyl-1-(4-(4-amino-5-(1-(1,1,1-trifluoropropan-2-yl)-1H-pyrazol-5-yl)pyrrolo[2,1-f][1,2,4]triazin-7-yl)pyridin-2-yl)-3,3-dimethylpiperazin-2-one (85); 1-(5-(4-amino-5-chloropyrrolo[2,1-f][1,2,4]triazin-7-yl)pyridin-3-yl)-4-(cyclopropanecarbonyl)-3,3-dimethylpiperazin-2-one (86); 1-(5-(4-amino-5-(1-(2,2,2-trifluoroethyl)-1H-pyrazol-5-yl)pyrrolo[2,1-f][1,2,4]triazin-7-yl)pyridin-3-yl)-4-(cyclopropanecarbonyl)-3,3-dimethylpiperazin-2-one (87); 4-acetyl-1-(5-(4-amino-5-(trifluoromethyl)pyrrolo[2,1-f][1,2,4]triazin-7-yl)pyridin-3-yl)-3,3-dimethylpiperazin-2-one (88); 1-(5-(4-amino-5-(1-(tetrahydro-2H-pyran-4-yl)-1H-pyrazol-5-yl)pyrrolo[2,1-f][1,2,4]triazin-7-yl)pyridin-3-yl)-4-(cyclopropanecarbonyl)-3,3-dimethylpiperazin-2-one (89); (R)-1-(4-(4-amino-5-(1-(1,1,1-trifluoropropan-2-yl)-1H-pyrazol-5-yl)pyrrolo[2,1-f][1,2,4]triazin-7-yl)pyridin-2-yl)-4-(cyclopropanecarbonyl)-3,3-dimethylpiperazin-2-one (90); (S)-4-acetyl-1-(5-(4-amino-5-chloropyrrolo[2,1-f][1,2,4]triazin-7-yl)pyridin-3-yl)-3,3,6-trimethylpiperazin-2-one (91); (S)-4-acetyl-1-(5-(4-amino-5-(trifluoromethyl) pyrrolo[2,1-f][1,2,4]triazin-7-yl)pyridin-3-yl)-3,3,6-trimethylpiperazin-2-one (92); (S)-4-acetyl-1-(4-(4-amino-5-(trifluoromethyl)pyrrolo[2,1-f][1,2,4]triazin-7-yl)pyridin-2-yl)-3,3,6-trimethylpiperazin-2-one (93); (S)-4-acetyl-1-(4-(4-amino-5-(1-methyl-1H-pyrazol-4-yl)pyrrolo[2,1-f][1,2,4]triazin-7-yl)pyridin-2-yl)-3,3,6-trimethylpiperazin-2-one (94); (R)-4-(5-(4-amino-5-chloropyrrolo[2,1-f][1,2,4]triazin-7-yl)-2-methylpyridin-3-yl)-2,2,6-trimethylmorpholin-3-one (95); (S)-4-acetyl-1-(4-(4-amino-5-(1-(2,2,2-trifluoroethyl)-1H-pyrazol-5-yl)pyrrolo[2,1-f][1,2,4]triazin-7-yl)pyridin-2-yl)-3,3,6-trimethylpiperazin-2-one (96); (R)-4-(5-(4-amino-5-(1-(2,2,2-trifluoroethyl)-1H-pyrazol-5-yl)pyrrolo[2,1-f][1,2,4]triazin-7-yl)-2-methylpyridin-3-yl)-2,2,5-trimethylmorpholin-3-one (97); (S)-4-acetyl-1-(4-(4-amino-5-chloropyrrolo[2,1-f][1,2,4]triazin-7-yl)pyridin-2-yl)-3,3,6-trimethylpiperazin-2-one (98); (S)-4-(5-(4-amino-5-(trifluoromethyl)pyrrolo[2,1-f][1,2,4]triazin-7-yl)-2-methylpyridin-3-yl)-2,2,5-trimethylmorpholin-3-one (99); (R)-4-(5-(4-amino-5-chloro-6-fluoropyrrolo[2,1-f][1,2,4]triazin-7-yl)-2-methylpyridin-3-yl)-2,2,5-trimethylmorpholin-3-one (100); (R)-4-(5-(4-amino-5-(trifluoromethyl)pyrrolo[2,1-f][1,2,4]triazin-7-yl)-2-methylpyridin-3-yl)-2,2,5-trimethylmorpholin-3-one (101); (S)-4-acetyl-1-(5-(4-amino-5-(1-methyl-1H-pyrazol-4-yl)pyrrolo[2,1-f][1,2,4]triazin-7-yl)pyridin-3-yl)-3,3,6-trimethylpiperazin-2-one (102); (S)-4-(5-(4-amino-5-(trifluoromethyl)pyrrolo[2,1-f][1,2,4]triazin-7-yl)-2-methylpyridin-3-yl)-2,2,6-trimethylmorpholin-3-one (103); ((S)-4-acetyl-1-(5-(4-amino-5-(1-(2,2,2-trifluoroethyl)-1H-pyrazol-5-yl)pyrrolo[2,1-f][1,2,4]triazin-7-yl)pyridin-3-yl)-3,3,6-trimethylpiperazin-2-one (104); (S)-4-(5-(4-amino-5-(1-(2,2,2-trifluoroethyl)-1H-pyrazol-5-yl)pyrrolo[2,1-f][1,2,4]triazin-7-yl)-2-methylpyridin-3-yl)-2,2,5-trimethylmorpholin-3-one (105); (S)-4-acetyl-1-(6-(4-amino-5-chloropyrrolo[2,1-f][1,2,4]triazin-7-yl)pyridin-2-yl)-3,3,6-trimethylpiperazin-2-one (106); (S)-4-(5-(4-amino-5-(1-(2,2,2-trifluoroethyl)-1H-pyrazol-5-yl)pyrrolo[2,1-f][1,2,4]triazin-7-yl)-2-methylpyridin-3-yl)-2,2,6-trimethylmorpholin-3-one (107); (S)-4-acetyl-1-(6-(4-amino-5-(1-(2,2,2-trifluoroethyl)-1H-pyrazol-5-yl)pyrrolo[2,1-f][1,2,4]triazin-7-yl)pyridin-2-yl)-3,3,6-trimethylpiperazin-2-one (108); (S)-7-(6-(4-acetyl-3,3,6-trimethyl-2-oxopiperazin-1-yl)pyridin-2-yl)-4-aminopyrrolo[2,1-f][1,2,4]triazine-5-carbonitrile (109); (S)-4-acetyl-1-(6-(4-amino-5-(1-methyl-1H-pyrazol-4-yl)pyrrolo[2,1-f][1,2,4]triazin-7-yl)pyridin-2-yl)-3,3,6-trimethylpiperazin-2-one (110); (S)-4-acetyl-1-(6-(4-amino-5-(trifluoromethyl)pyrrolo[2,1-f][1,2,4]triazin-7-yl)pyridin-2-yl)-3,3,6-trimethylpiperazin-2-one (111); (S)-4-(4-(4-amino-5-(1-(2,2,2-trifluoroethyl)-1H-pyrazol-5-yl)pyrrolo[2,1-f][1,2,4]triazin-7-yl)pyridin-2-yl)-2,2,5-trimethylmorpholin-3-one (112); (4-(4-amino-5-(trifluoromethyl)pyrrolo[2,1-f][1,2,4]triazin-7-yl)morpholin-2-yl)(pyrrolidin-1-yl)methanone (113); 4-(4-amino-5-(trifluoromethyl)pyrrolo[2,1-f][1,2,4]triazin-7-yl)-N-isopropylmorpholine-2-carboxamide (114); 4-(4-amino-5-(trifluoromethyl)pyrrolo[2,1-f][1,2,4]triazin-7-yl)-N-cyclohexylmorpholine-2-carboxamide (115); 1-(4-amino-5-(trifluoromethyl)pyrrolo[2,1-f][1,2,4]triazin-7-yl)-N-cyclopentylpiperidine-3-carboxamide (116); 1-(4-amino-5-(trifluoromethyl)pyrrolo[2,1-f][1,2,4]triazin-7-yl)-N,N-dimethylpiperidine-3-carboxamide (117); 1-(4-amino-5-(trifluoromethyl)pyrrolo[2,1-f][1,2,4]triazin-7-yl)-N-phenylpiperidine-3-carboxamide (118); and 1-(4-amino-5-(trifluoromethyl)pyrrolo[2,1-f][1,2,4]triazin-7-yl)-N-isopropylpiperidine-3-carboxamide (119).

One embodiment provides at least one compound of Formula (I) or a salt thereof, wherein $Q_1$ is Cl, Br, I, —CN, or —$CF_3$; and $Q_2$ and $R_4$ are defined in the first aspect or the second aspect. Included in this embodiment are compounds in which $Q_2$ is indazole substituted with $R_2$ and $R_3$. Also included are compounds in which $Q_2$ is indazole substituted with tetrahydropyranyl.

One embodiment provides at least one compound of Formula (I) or a salt thereof, wherein $Q_2$ is morpholinyl or piperidinyl, each substituted with $R_2$ and $R_3$; and $Q_1$, $R_2$, $R_3$, and $R_4$ are defined in the first aspect. Included in this embodiment are compounds in which $Q_1$ is —$CF_3$; $R_2$ is —C(O)(pyrrolidinyl), —C(O)NHCH(CH$_3$)$_2$, —C(O)NH(cyclohexyl), —C(O)NH(cyclopentyl), —C(O)N(CH$_3$)$_2$, —C(O)NH(phenyl), or —C(O)NHCH(CH$_3$)$_2$; and $R_3$ is H.

One embodiment provides at least one compound of Formula (I) or a salt thereof, wherein said compound is selected from 4-amino-7-[1-(oxan-4-yl)-1H-indazol-6-yl]pyrrolo[2,1-f][1,2,4]triazine-5-carbonitrile (73); 5-iodo-7-[1-(oxan-4-yl)-1H-indazol-6-yl]pyrrolo[2,1-f][1,2,4]triazin-4-amine (75); 5-chloro-7-[1-(oxan-4-yl)-1H-indazol-6-yl]pyrrolo[2,1-f][1,2,4]triazin-4-amine (76); 5-bromo-7-[1-(oxan-4-yl)-1H-indazol-6-yl]pyrrolo[2,1-f][1,2,4]triazin-4-amine (77); 4-acetyl-1-(5-(4-amino-5-chloropyrrolo[2,1-f][1,2,4]triazin-7-yl)pyridin-3-yl)-3,3-dimethylpiperazin-2-one (83); 1-(5-(4-amino-5-chloropyrrolo[2,1-f][1,2,4]triazin-7-yl)pyridin-3-yl)-4-(cyclopropanecarbonyl)-3,3-dimethylpiperazin-2-one (86); 4-acetyl-1-(5-(4-amino-5-(trifluoromethyl)pyrrolo[2,1-f][1,2,4]triazin-7-yl)pyridin-3-yl)-3,3-dimethylpiperazin-2-one (88); (S)-4-acetyl-1-(5-(4-amino-5-chloropyrrolo[2,1-f][1,2,4]triazin-7-yl)pyridin-3-yl)-3,3,6-trimethylpiperazin-2-one (91); (S)-4-acetyl-1-(5-(4-amino-5-(trifluoromethyl)pyrrolo[2,1-f][1,2,4]triazin-7-yl)pyridin-3-yl)-3,3,6-trimethylpiperazin-2-one (92); (S)-4-acetyl-1-(4-(4-amino-5-(trifluoromethyl)pyrrolo[2,1-f][1,2,4]triazin-7-yl)pyridin-2-yl)-3,3,6-trimethylpiperazin-2-one (93); (R)-4-(5-(4-amino-5-chloropyrrolo[2,1-f][1,2,4]triazin-7-yl)-2-methylpyridin-3-yl)-2,2,6-trimethylmorpholin-3-one (95); (S)-4-acetyl-1-(4-(4-amino-5-chloropyrrolo[2,1-f][1,2,4]triazin-7-yl)pyridin-2-yl)-3,3,6-trimethylpiperazin-2-one (98); (S)-4-(5-(4-amino-5-(trifluoromethyl)pyrrolo[2,1-f][1,2,4]triazin-7-yl)-2-methylpyridin-3-yl)-2,2,5-trimethylmorpholin-3-one (99); (R)-4-(5-(4-amino-5-chloro-6-fluoropyrrolo[2,1-f][1,2,4]triazin-7-yl)-2-methylpyridin-3-yl)-2,2,5-trimethylmorpholin-3-one (100); (R)-4-(5-(4-amino-5-(trifluoromethyl)pyrrolo[2,1-f][1,2,4]triazin-7-yl)-2-methylpyridin-3-yl)-2,2,5-trimethylmorpholin-3-one (101); (S)-4-(5-(4-amino-5-(trifluoromethyl)pyrrolo[2,1-f][1,2,4]triazin-7-yl)-2-methylpyridin-3-yl)-2,2,6-trimethylmorpholin-3-one (103); (S)-4-acetyl-1-(6-(4-amino-5-chloropyrrolo[2,1-f][1,2,4]triazin-7-yl)pyridin-2-yl)-3,3,6-trimethylpiperazin-2-one (106); (S)-7-(6-(4-acetyl-3,3,6-trimethyl-2-oxopiperazin-1-yl)pyridin-2-yl)-4-aminopyrrolo[2,1-f][1,2,4]triazine-5-carbonitrile (109); (S)-4-acetyl-1-(6-(4-amino-5-(trifluoromethyl)pyrrolo[2,1-f][1,2,4]triazin-7-yl)pyridin-2-yl)-3,3,6-trimethylpiperazin-2-one (111); (4-(4-amino-5-(trifluoromethyl)pyrrolo[2,1-f][1,2,4]triazin-7-yl)morpholin-2-yl)(pyrrolidin-1-yl)methanone (113); 4-(4-amino-5-(trifluoromethyl)pyrrolo[2,1-f][1,2,4]triazin-7-yl)-N-isopropylmorpholine-2-carboxamide (114); 4-(4-amino-5-(trifluoromethyl)pyrrolo[2,1-f][1,2,4]triazin-7-yl)-N-cyclohexylmorpholine-2-carboxamide (115); 1-(4-amino-5-(trifluoromethyl)pyrrolo[2,1-f][1,2,4]triazin-7-yl)-N-cyclopentylpiperidine-3-carboxamide (116); 1-(4-amino-5-(trifluoromethyl)pyrrolo[2,1-f][1,2,4]triazin-7-yl)-N,N-dimethylpiperidine-3-carboxamide (117); 1-(4-amino-5-(trifluoromethyl)pyrrolo[2,1-f][1,2,4]triazin-7-yl)-N-phenylpiperidine-3-carboxamide (118); and 1-(4-amino-5-(trifluoromethyl)pyrrolo[2,1-f][1,2,4]triazin-7-yl)-N-isopropylpiperidine-3-carboxamide (119).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "$C_{1-4}$fluoroalkyl" is intended to include C1, C2, C3, and C4 alkyl groups substituted with one or more fluorine atoms. Representative examples of fluoroalkyl groups include, but are not limited to, —$CF_3$ and —$CH_2CF_3$.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$ hydroxyalkyl.

The term "hydroxy-fluoroalkyl" includes both branched and straight-chain saturated alkyl groups substituted with one or more hydroxyl groups and one or more fluorine atoms. Representative examples of hydroxy-fluoroalkyl groups include, but are not limited to, —$CF_2OH$ and —$CF_2CH_2OH$.

The term "cyano" refers to the group —CN.

The term "oxo" refers to the group =O.

The term "cycloalkyl", as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "fluorocycloalkyl" refers to a cycloalkyl group in which one or more hydrogen atoms are replaced by fluoro group(s).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) Wermuth, C. G. et al., *The Practice of Medicinal Chemistry*, Chapter 31, Academic Press (1996);
b) Bundgaard, H. ed., *Design of Prodrugs*, Elsevier (1985);
c) Bundgaard, H., Chapter 5, "Design and Application of Prodrugs", *A Textbook of Drug Design and Development*, pp. 113-191, Krogsgaard-Larsen, P. et al., eds., Harwood Academic Publishers (1991); and
d) Testa, B. et al., *Hydrolysis in Drug and Prodrug Metabolism*, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to PI3K, or effective to treat or prevent autoimmune and/or inflammatory disease states, such as multiple sclerosis and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Utility

The compounds of the invention modulate kinase activity, including the modulation of PI3K.

Accordingly, compounds of Formula (I) have utility in treating conditions associated with the modulation of kinase activity, and particularly the selective inhibition of PI3K activity. Such conditions include B-cell mediated diseases in which cytokine levels are modulated as a consequence of intracellular signaling.

As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

In view of their activity as selective inhibitors of PI3K, compounds of Formula (I) are useful in treating cytokine-associated conditions including, but not limited to, inflammatory diseases such as Crohn's and ulcerative colitis, asthma, graft versus host disease, chronic obstructive pulmonary disease; autoimmune diseases such as Graves' disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovascularization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, Kawasaki disease, chronic inflammatory demyelinating polyneuropathy (CIDP), dermatomyositis, uveitis, anti-factor-VIII disease, ankylosing spondylitis, myasthenia gravis, Goodpasture's disease, antiphospholipid syndrome, ANCA-associated vasculitis, dermatomyositis/polymyositis, cerebral malaria, chronic pulmonary inflammatory disease, silicosis, pulmonary sarcoidosis, bone resorption disease, allograft rejections, fever and myalgias due to infection, cachexia secondary to infection, myeloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovascularization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's and ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In addition, the PI3K inhibitors of the present invention inhibit the expression of inducible pro-inflammatory proteins such as prostaglandin endoperoxide synthase-2 (PGHS-2), also referred to as cyclooxygenase-2 (COX-2). Accordingly, additional PI3K-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "PI3K-associated condition" or "PI3K-associated disease or disorder" are used herein, each is intended to encompass all of the conditions identified above as if repeated at length, as well as any other condition that is affected by PI3K kinase activity.

"Therapeutically effective amount" is intended to include an amount of a compound of the present invention that is effective when administered alone or in combination to inhibit PI3K.

One embodiment provides methods for treating such PI3K kinase-associated conditions, comprising administering to a subject in need thereof at least one compound of Formula (I). A therapeutically-effective amount for treating such conditions may be administered. The methods of the present embodiment may be employed to treat PI3K kinase-associated conditions such as treatment of allergic disorders and/or autoimmune and/or inflammatory diseases including, but not limited to, SLE, rheumatoid arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

The methods of treating PI3K kinase-associated conditions may comprise administering at least one compound of Formula (I) alone or in combination with each other and/or other suitable therapeutic agents useful in treating such conditions. Therapeutically-effective amounts of at least one compound of Formula (I) and other suitable therapeutic agents for treating such conditions may be administered. Accordingly, "therapeutically effective amount" is also intended to include an amount of the combination of compounds claimed that is effective to treat PI3K kinase-associated conditions. The combination of compounds is preferably a synergistic combination. Synergy, as described, for example, by Chou et al., *Adv. Enzyme Regal.*, 22:27-55 (1984), occurs when the effect (in this case, inhibition of PI3K) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-PI3K effect, or some other beneficial effect of the combination compared with the individual components.

Exemplary of such other therapeutic agents include corticosteroids, rolipram, calphostin, cytokine-suppressive anti-inflammatory drugs (CSAIDs), 4-substituted imidazo[1,2-a]quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating PI3K kinase-associated conditions, including IL-1, IL-6, IL-8, IFN' and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Another embodiment provides the compounds of Formula (I) for use in therapy. In the present embodiment, the use in therapy may include the administration of a therapeutically-effective amount of a compound of Formula (I).

The present invention also provides the use of the compounds of Formula (I) for the manufacture of a medicament for the treatment or prophylaxis of an allergic disorder and/or autoimmune and/or inflammatory disease. In the present embodiment, the use for the manufacture of a medicament may include the administration of a therapeutically-effective amount of a compound of Formula (I) for the treatment of prophylaxis of an allergic disorder and/or autoimmune and/or inflammatory disease.

The present invention also provides the use of the compounds of Formula (I) for the manufacture of a medicament for treatment of cancer. The present embodiment may include the use for the manufacture of a medicament includes the administration of a therapeutically-effective amount of a compound of Formula (I) for the treatment of prophylaxis of an allergic disorder and/or autoimmune and/or inflammatory disease.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

The compounds of Formula (I) may be administered by any means suitable for the condition to be treated, which may depend on the need for site-specific treatment or quantity of drug to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; buccally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of PI3K enzyme levels.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

Examples of compounds of Formula (I) as specified in the "Examples" section below, have been tested in one or more of the assays described below.

In one embodiment, the compounds of Formula (I) inhibit PI3K enzymes with $IC_{50}$ values of 70 nM or less, for example, from 0.001 to 70 nM, as measured by the ADP-Glo Format PI3K assays. Preferably, the compounds of Formula (I) inhibit PI3K enzymes with $IC_{50}$ values of 20 nM and less, for example, from 0.001 to 20 nM. Other preferred compounds inhibit PI3K enzymes with $IC_{50}$ values of 10.0 nM and less, for example, from 0.001 to 10.0 nM.

In one embodiment, the compounds of Formula (I) have improved potency in the whole blood BCR-stimulated CD69 expression assay with $IC_{50}$ values of 5 mM or less, for example, from 0.1 to 5 mM. More preferably, the compounds of Formula (I) have potency in the whole blood BCR-stimulated CD69 expression assay with $IC_{50}$ values of 1 mM or less, for example, from 0.1 to 1 mM; and with $IC_{50}$ values of 500 nM or less, for example, from 0.1 to 500 nM.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples and intermediates section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Abbreviations

Ac acetyl
ACN acetonitrile
AcOH acetic acid
aq. aqueous
anhyd. anhydrous
Bn benzyl
Bu butyl
Boc tert-butoxycarbonyl
° C. degrees Centigrade
Cbz carbobenzyloxy
Conc. concentration
d day(s)
DCM dichloromethane
DIPEA diisopropylethylamine
DMF dimethylformamide
DMSO dimethylsulfoxide
dppf 1,1'-bis(diphenylphosphino)ferrocene
DTT dithiothreitol
EGTA ethylene glycol tetraacetic acid
$Et_3N$ triethyl amine
% ee percent enantiomeric excess
(+/−) or (±) racemic
eq. or Eq. or equiv. equivalent(s)
EtOAc ethyl acetate
Et ethyl
Ex example
H hydrogen
Hex hexanes
h or hr hour(s)
i iso
IPA isopropanol
Hz hertz
HPLC high pressure liquid chromatography
RP-HPLC reverse-phase high pressure liquid chromatography
LC liquid chromatography
LCMS or LC/MS liquid chromatograph mass spectrometry
mCPBA meta-chloroperbenzoic acid
MHz megahertz
Me methyl
MeOH methanol
min. minute(s)
$M^+$ $(M+H)^+$
$M^{+1}$ $(M+H)+$
MS mass spectrometry
m/z mass to charge ratio
N Normal
NBS N-bromosuccinimide
NCS N-chlorosuccinimide
NIS N-iodosuccinimide
NMR nuclear magnetic resonance
Pd/C palladium on carbon
$PdCl_2(dppf)$ 1,1-bis(diphenylphosphino)ferrocene]dichloropalladium(II)
$Pd(PPh_3)_4$ tetrakis(triphenylphosphine)palladium
Ph phenyl
Pr propyl
ppm parts per million
PSI or psi pounds per square inch
quant. quantitative
Ret Time or Rt retention time
sat. or sat'd. saturated
sec second(s)
SFC super critical fluid
SM or sm starting material
t tert
TBAI tetrabutyl ammonium iodide
TFA trifluoroacetic acid
THF tetrahydrofuran
TLC thin layer chromatography
TMS trimethylsilane
TMS-I or TMSI iodotrimethylsilane
t triplet
m multiplet
s singlet
d doublet
br. s. broad singlet
dd doublet of doublets
tt triplet of triplets
ddd doublet of doublet of doublets
q quartet
quin. quintet
UV ultraviolet
W/V or w/v weight to volume The compounds of Formula (I) may be prepared by the processes described herein in the following reaction schemes. Examples of suitable reagents and procedures for conducting these reactions appear hereinafter and in the working examples included therein. Protection and deprotection in the schemes herein may be carried out by procedures generally known in the art (See, for example, Greene, T. W. et al., *Protecting Groups in Organic Synthesis*, Third Edition, Wiley (1999)).

Compounds of Formula (I) can be prepared using methods shown in Scheme 1. Compounds 1 (for preparation see WO 2011/123493, Example 1F) can be converted to the corresponding acetylene compound 2 by reacting with ethynlsilane and base, such as n-butyl lithium. 1,5-Pyrazoles 3 can be prepared as the major isomer by reacting compounds 2 with hydrazines 4 with heating. The regio-isomeric 1,3 pyrazoles 5 can be obtained as a secondary product. Alternatively in Scheme 2, compound 1 is treated with dimethylamine to give the intermediate 6, which forms cleanly the pyrazoles 3 when reacted with hydrazines 4.

Scheme 1

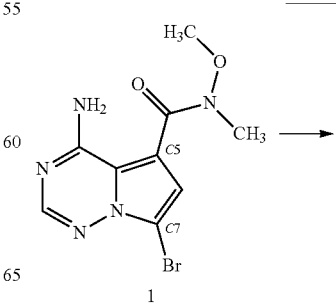

1

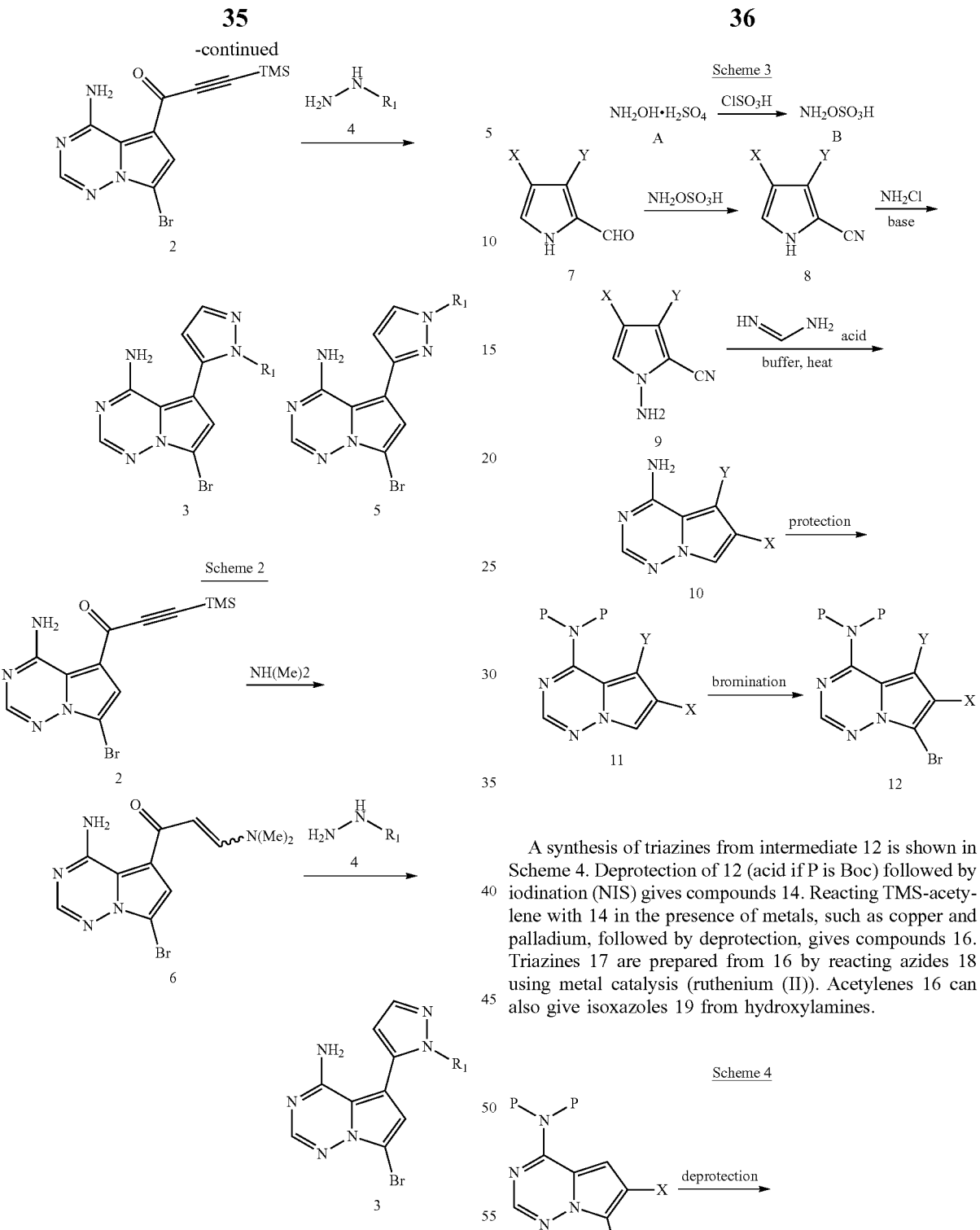

A synthesis of intermediate 12 for the preparation of compounds of Formula (I) is shown in Scheme 3. Compounds 7 can be transformed to nitriles 8 using aminooxysulfonic acid (B) Aminopyrroles 9 can be prepared from 8 using chloramine, then transformed to the pyrrolotriazines 10 with formimidamide. The amino group in 10 can be protected, such as P being the Boc group, to give compounds 11. Bromination, with NBS for example, can give the bromos 12. In Scheme 3, X and Y can both be hydrogen, fluoro or one of X and Y are independently fluoro.

A synthesis of triazines from intermediate 12 is shown in Scheme 4. Deprotection of 12 (acid if P is Boc) followed by iodination (NIS) gives compounds 14. Reacting TMS-acetylene with 14 in the presence of metals, such as copper and palladium, followed by deprotection, gives compounds 16. Triazines 17 are prepared from 16 by reacting azides 18 using metal catalysis (ruthenium (II)). Acetylenes 16 can also give isoxazoles 19 from hydroxylamines.

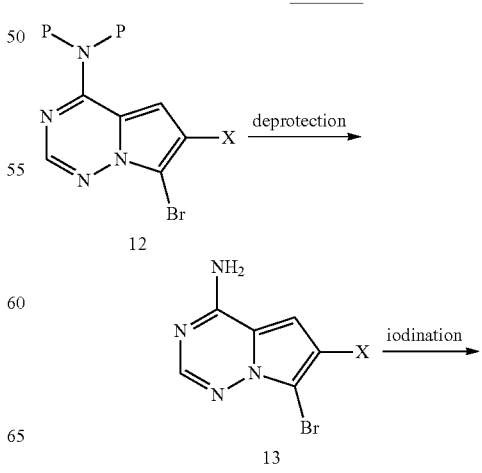

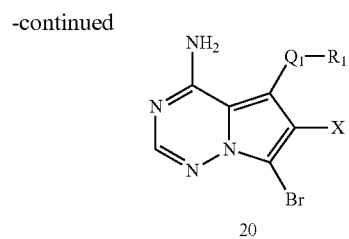

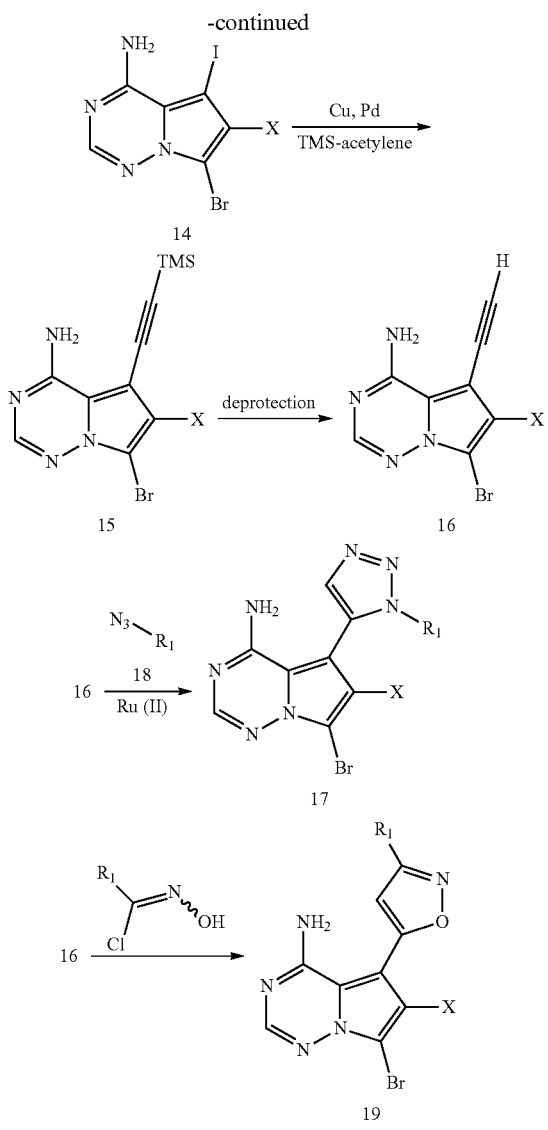

Intermediates 14 can be used to react with boronic esters or acids of optimally substituted heteroaryls as shown in Scheme 5. Under metal assisted coupling conditions, such as palladium assisted Suzuki reactions, bromo intermediates 20 are formed from 14 using boronic esters or acids QB, selectively reacting at the C5 iodo. The reagents QB are either commercially available or prepared via methods known in the art (see, for example, Ishiyama, T. et al., *Tetrahedron*, 57:9813 (2001), and references cited therein).

Scheme 5

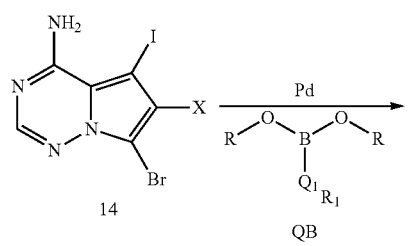

Analogs with a C-7 bromo (such as 3, 5, 17, and 19), represented by compounds 20, can be further transformed to compounds of Formula I by Scheme 6. This conversion may be achieved by using a suitable base such as potassium carbonate, cesium carbonate or tripotassium phosphate, and a suitable catalyst such as tetrakis(triphenylphosphine) palladium, 1,1'-bis(diphenylphosphino)ferrocene palladium(II) chloride, or 1,1'-bis(di-tert-butylphosphino)ferrocene palladium(II) chloride, in a suitable solvent such as dioxane or tetrahydrofuran, optionally with a suitable cosolvent such as water. Such coupling reactions are commonly known as Suzuki-Miyaura coupling reactions, and are well known in the chemical literature (see, for example, Heravi, M. M. et al., *Tetrahedron*, 68:9145 (2012), and references cited therein).

Reacting compounds 20 with heteroaryl boronic esters or acids 21 will give C7 heteroaryl linked analogs 22 of Formula 1. The reagents 21 are either commercially available or prepared using methods well known in the chemical literature (see, for example, Ishiyama, T. et al., *Tetrahedron*, 57:9813 (2001), and references cited therein). One method called General Procedure 1 involves taking an appropriate halo (optimally bromo) analog 23 and forming the boronic ester intermediate 21 using palladium catalysis followed by a second palladium assisted coupling in the same reaction vessel with 20 to give compounds 22. This transformation can also be done step-wise by isolating 21.

Scheme 6

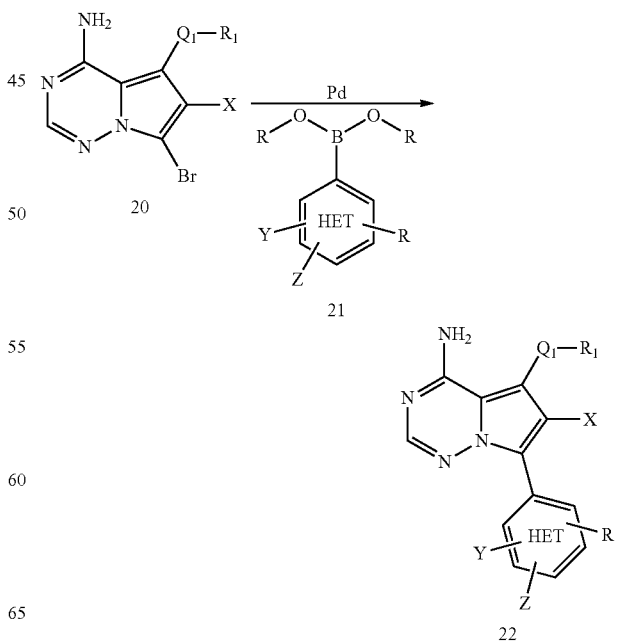

Scheme 8

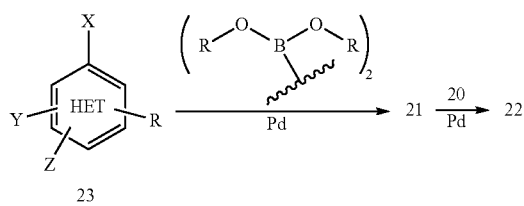

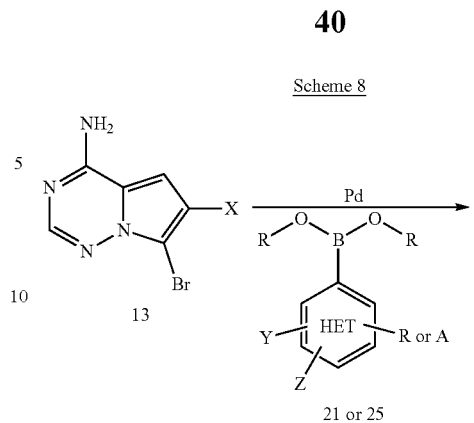

Alternatively, coupling of compounds 20 will provide compounds 24 that can be further transformed to new compounds of Formula I (Scheme 7). Standard coupling with compounds 25 with a group A that can be further modified gives 24. The group A can be halogens, such as bromo, that can be used in Suzuki couplings with boronic esters or acids or in Buchwald couplings with amines. The group A can also be a carboxylic acid for use in standard amide coupling reactions. Boronic esters can also be used as Group A, allowing Suzuki couplings with desired halogen intermediates. Benzylic amines can also be group A, allowing standard functionalization of amines (reductive aminations, Buchwald couplings, as well as amide, urea or carbamate formations).

Scheme 7

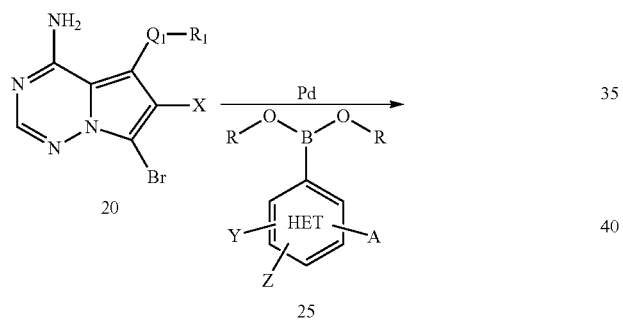

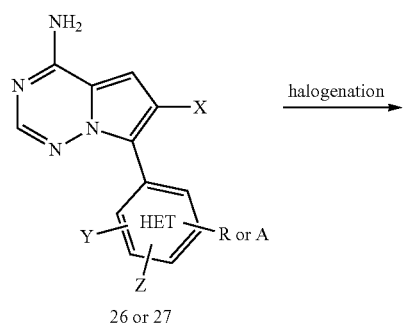

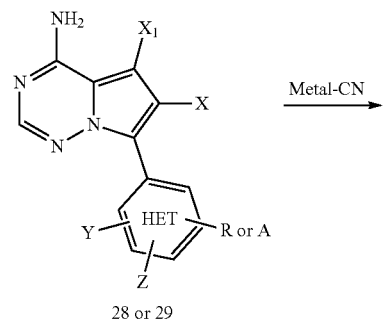

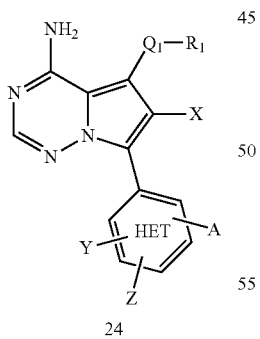

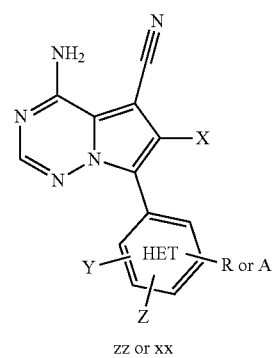

Bromos 13 can be coupled with heteroaryl boronic esters or acids 21 or 25 to give compounds 26 or 27 as shown in Scheme 8. Halogenation under standard procedures would give final compounds 28 or 29 of Formula I where X1 is chloro, bromo or iodo. Compounds 28 or 29, optimally with X1 as iodo, can be further transformed to nitriles with a cyanide nucleophile, such as copper cyanide, to give xx and zz.

Alternatively, intermediate 16 can be treated with TMS-azide and base (cesium carbonate) in air to give directly the bromo nitrile intermediate xyx, as shown in Scheme 9. Intermediates xyx can be transformed as described and shown in Schemes 10 and 11 to give compounds xyx2 or xyx3.

Scheme 9

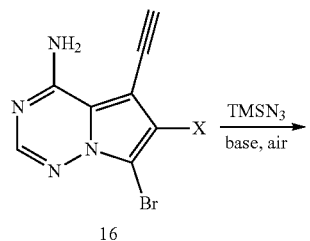
16

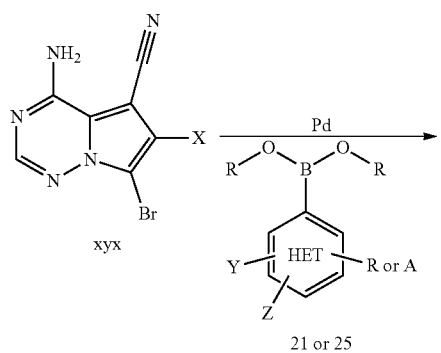
xyx

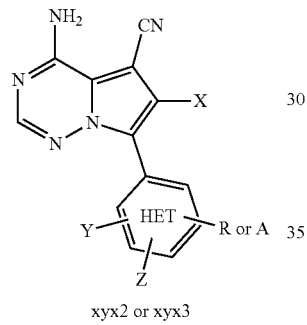
xyx2 or xyx3

-continued

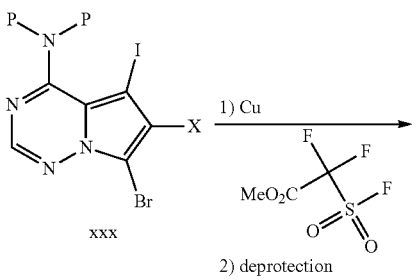
xxx

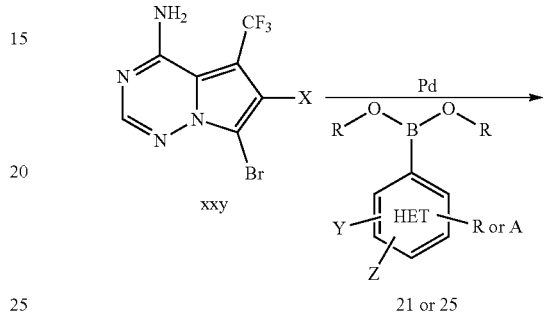
xxy

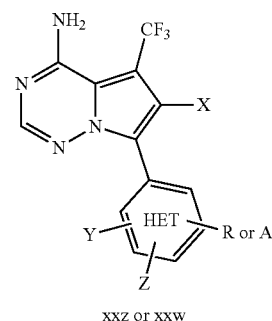
xxz or xxw

Compounds of Formula I where $Q_1$ is a trifluoromethyl group can be prepared as shown in Scheme 10. The protected (optimally para-methoxybenzyl) amine 12 can be iodinated under standard conditions (NIS) to give xxx. Treatment of xxx with Cu(I)I and methyl 2,2-difluoro-2-(fluorosulfonyl)acetate with heating gives intermediate xxy after deprotection. Intermediates xxy can be transformed as described and shown in Schemes X and X1 to give compounds xxz or xxw. Alternatively, compounds 28 or 29 can be protected followed by reacting with copper iodide and methyl 2,2-difluoro-2-(fluorosulfonyl)acetate to give after deprotection xxz or xxw.

Alternately, compounds 28 or 29, optimally X1 is iodo or bromo, can be reacted with boronic esters or acids of optimally substituted heteroaryls QB to give compounds 22 or 24, as shown in Scheme 11. Some heteroaryls QC can be coupled directly with palladium to compounds 28 or 29 without requiring boronic ester or acid intermediates to give 22 or 24.

Scheme 10

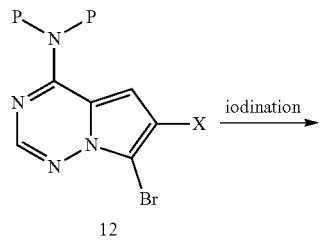
12

Scheme 11

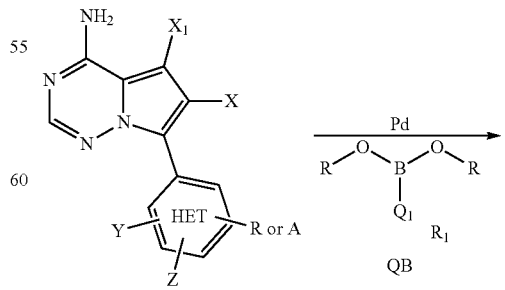
28 or 29

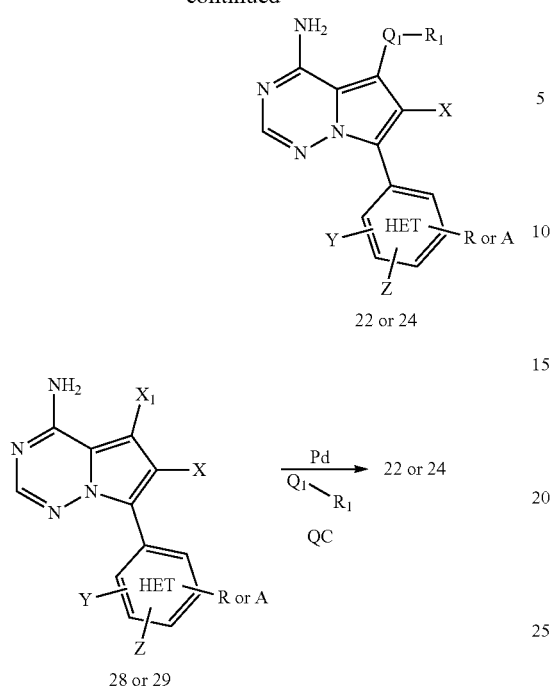

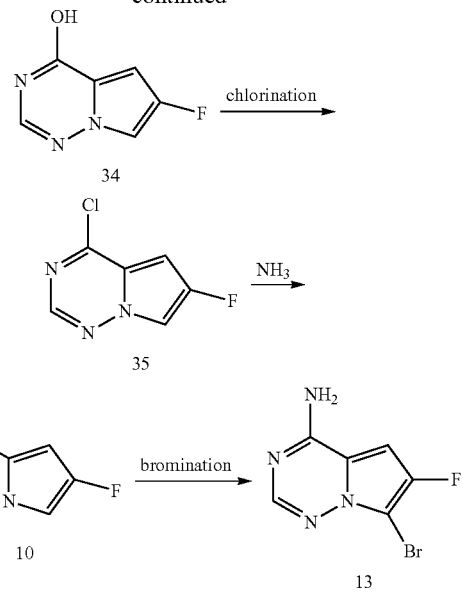

Alternatively, intermediate 12 where X is fluoro can be prepared as shown in Scheme 12. Compounds 30 can be deprotected and oxidized (MnO$_2$) to pyrrole 32. Aminopyrroles 33 can be prepared from 32 using chloramine, then transformed to the pyrrolotriazines 34 with formamide. Compound 34 can be chlorinate (POCl$_3$) followed by treatment with ammonia to give intermediate 10 (X=F). Bromination as in Scheme 3 can give directly compound 13. Alternatively, the amine can be protected before bromination.

Scheme 13 describes a general procedure to synthesize key intermediates leading to imidazoles of Figure I. Compound 36 (for preparation see WO 2011/123493, Example 1) can be treated with base to give the acids 37, followed by reduction to the aldehydes 38. Enamine formation with optimally substituted amines followed by reacting with gives imidazoles 40. Intermediates 40 can be further transformed as in Schemes X or XI using compounds 21 or 25.

Scheme 12

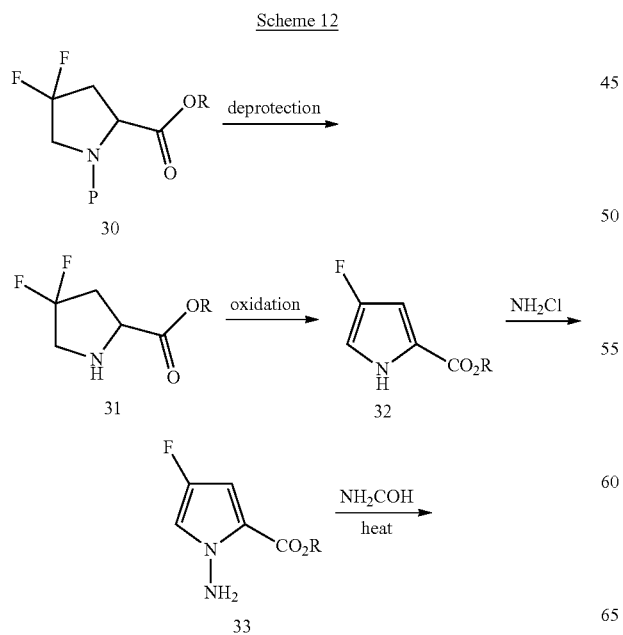

Scheme 13

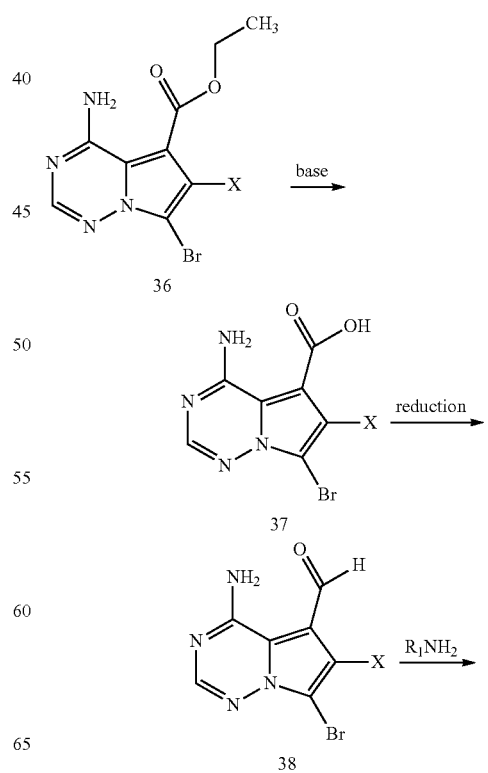

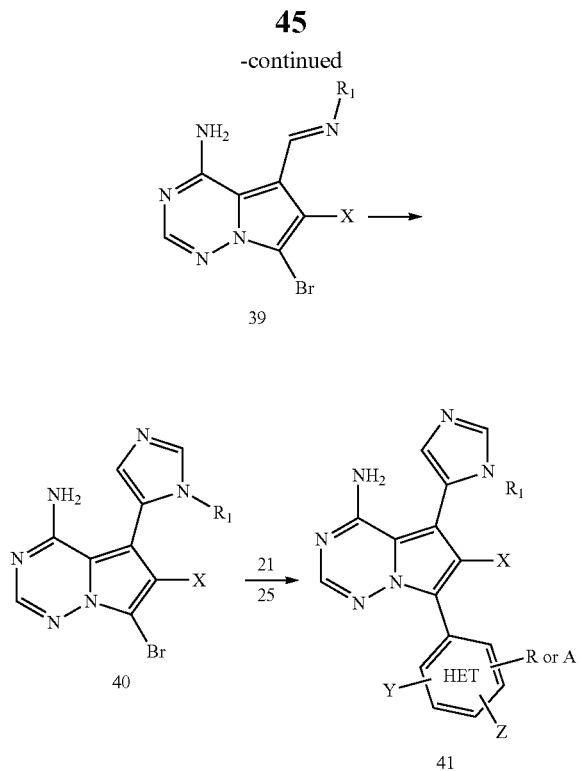

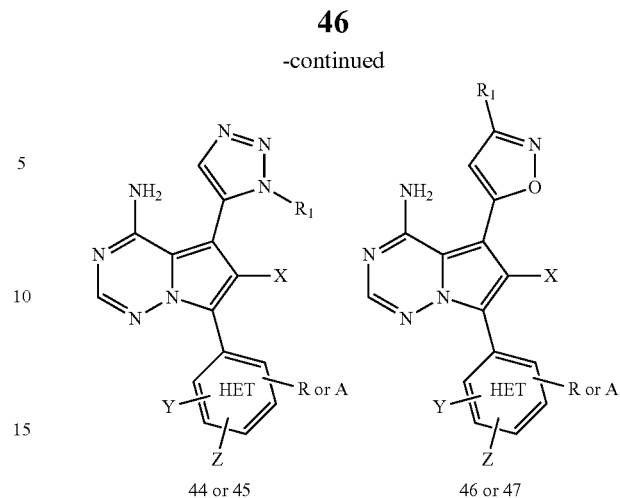

Analogs with X=CH in Formula I are prepared as in Scheme 15. The known ester C1 is brominated then reacted with a protected amine (dimethoxy benzyl amine) to give C2. Deprotection to the aniline followed by hydrolysis of the ester in C3 gives acid C4. Activation, shown as a Weinreb amide C5, followed by treatment with ethynlsilane and base (as described in Scheme 1) gives the acetylene intermediate C6. Intermediate C6 can be further transformed as described for Intermediate 2 in Schemes 1 and 2, giving 1,5-pyrazoles C7. Pyrazoles C7 can be transformed further into final compounds as described in the Schemes above.

Alternatively, triazines 44 or 45 and isooxazoles 46 or 47 can be prepared as shown in Scheme 14 from intermediates 28 or 29 by similar methods described for Scheme 4.

Scheme 14

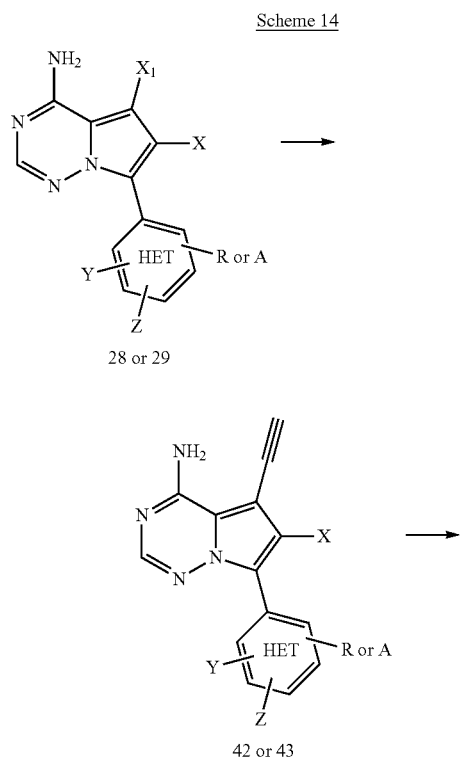

Scheme 15

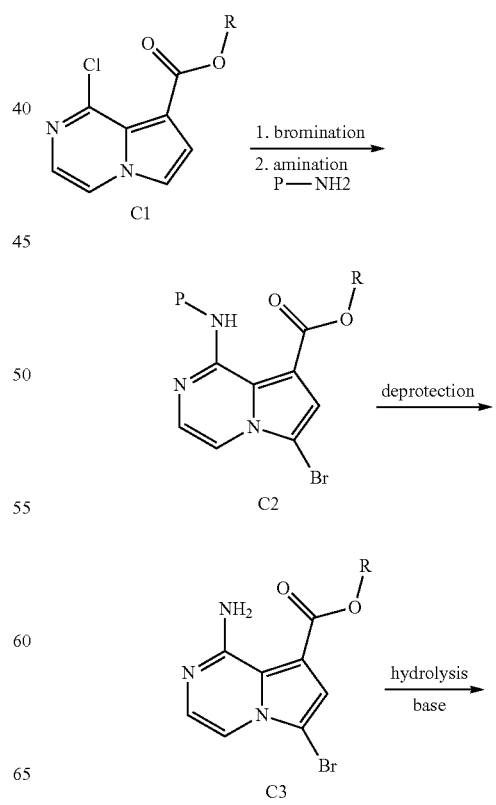

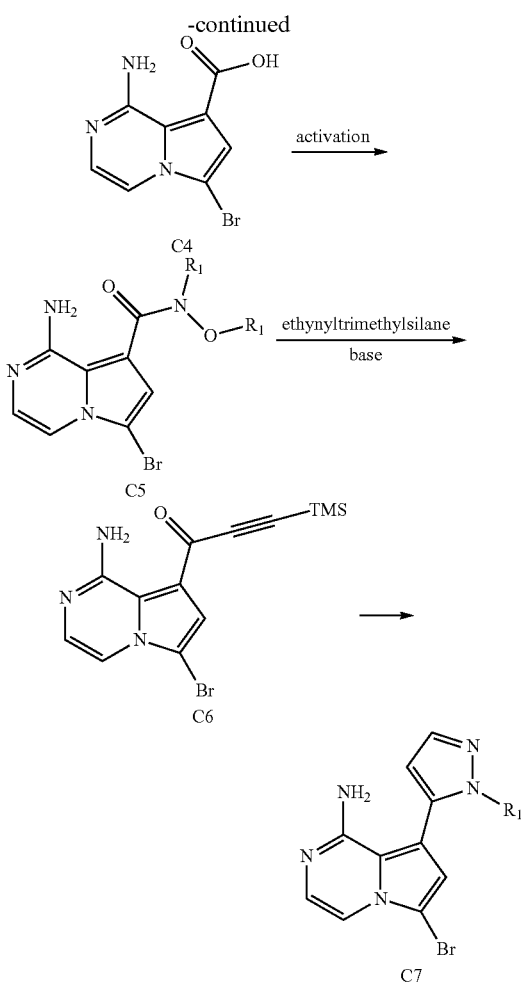

Preparative HPLC Conditions:

Method A: Column: Luna 5μ C18 30×100 mm; Flow rate=40 mL/min; Solvent A=10% MeOH—90% H₂O—0.1% TFA; Solvent B=90% MeOH—10% H₂O—0.1% TFA, Start % B=30, Final % B=100, linear gradient time=10 min; Products detected at 220 nm wavelength.

Method B: Column: Waters XBridge C18, 19×250 mm, 5-μm particles; Mobile Phase A: 5:95 acetonitrile:water with 10 mM ammonium acetate; Mobile Phase B: 95:5 acetonitrile:water with 10 mM ammonium acetate; Flow: 20 mL/min. Products detected by mass spectrometry. Fractions containing the desired product were combined and dried via centrifugal evaporation.

Method C: Column: Waters XBridge C18, 19×250 mm, 5-μm particles; Mobile Phase A: 5:95 acetonitrile:water with 0.05% TFA; Mobile Phase B: 95:5 acetonitrile:water with 0.05% TFA; 5-100% B over 25 minutes, then 5-minute hold at 100% B; Flow: 20 mL/min. Products detected by mass spectrometry. Fractions containing the desired product were combined and dried via centrifugal evaporation.

Method D: Column: SunFire 5μ C18 19×150 mm; Mobile Phase A: 90% H₂O—10% ACN—0.1% TFA; Mobile Phase B: 10% H₂O—90% ACN—0.1% TFA; Gradient: 0-100% B over 10 min then 4 minute hold at 100% B. Amount of Mobile Phases A and B were adjusted appropriately for the isolate of each title compound. Flow: 20 mL/min. Products detected by UV. Fractions containing the desired product were combined and dried via under reduced pressure and then partitioned between 1.5 M aqueous KH₂PO₄ and either DCM or ethyl acetate to remove residual TFA. The organic portion was dried over either MgSO₄ or Na₂SO₄ and the solvents were removed in vacuo providing title compound.

Analytical LCMS Conditions:

Method A: Column: PHENOMENEX® Luna 5μ C18 30×4.6 mm; Linear gradient of 0-100% Solvent B over 2 min, then 0.5 min hold at 100% B; Flow rate: 4 mL/min; Solvent A: 10% MeOH—90% H₂O—0.1% TFA; Solvent B: 90% MeOH—10% H₂O—0.1% TFA; Products detected at 220 nm wavelength w/positive or negative ionization mode.

Method B: Column: BEH C18 2.1×50 mm 1.7μ; Linear gradient of 0-100% Solvent B over 2 min, then 0.5 min hold at 100% B; Flow rate: 1 mL/min; Solvent A: 100% water w/0.05% TFA; Solvent B: 100% acetonitrile w/0.05% TFA; Products detected at 220 nm wavelength w/positive ionization mode.

Method C: Column: XBridge (150×4.6 mm), 3.5 μm SC/840; Flow rate: 1 mL/min; Solvent A: 10 mM NH₄HCO₃ in water pH=9.5 adjusted using dil. ammonia; Solvent B: MeOH; Products detected by positive or negative ionization.

Method D: Column-Ascentis Waters SunFire C18 2.1×50 mm 5 u; Mobile Phase A: 10% MeOH—90% H₂O—0.1% TFA; Mobile Phase B: 90% MeOH—10% H₂O—0.1% TFA; Gradient Time=4 min; Flow: 1 mL/min.; Oven Temp.=40° C.; Products detected at 220 nm wavelength w/positive ionization mode.

Method E: Column: SunFire C18, (150×4.6 mm), 3.5 μm, SC/862; Linear gradient of 0-100% Solvent B over 12 min, then 3 min hold at 100% B; Flow rate: 1 mL/min; Buffer: 0.5% TFA, in water with pH adjusted to 2.5 using dilute ammonia; Solvent A: Buffer: acetonitrile (95:5); Solvent B: acetonitrile; Products detected at 220 nm.

Method F: Column: Waters Acquity UPLC BEH C18, 2.1×50 mm, 1.7-μm particles; Linear gradient of 0-100% Solvent B over 3 min, with 0.75 min hold at 100% B; Flow rate: 1.1 mL/min; Solvent A: 5:95 acetonitrile:water with 0.05% TFA; Solvent B: 95:5 acetonitrile:water with 0.05% TFA; Temperature: 50° C.; Products detected at 220 nm, positive ionization mode.

Method G: Column: XBridge Phenyl (4.6×150 mm); Linear gradient of 0-100% Solvent B over 12 min, then 3 min hold at 100% B; Flow rate: 1 mL/min; Solvent A: 5% acetonitrile—95% H₂O—0.05% TFA; Solvent B: 95% acetonitrile—5% H₂O—0.05% TFA; Products detected at 220 nm.

Method H: Column: Waters Acquity BEH C18 2.1×50 mm 1.7 μm; Linear gradient of 0-100% Solvent B over 3 min, then 0.75 min hold at 100% B; Flow rate: 1.11 mL/min; Solvent A: 5:95 acetonitrile:water with 10 mM ammonium acetate; Solvent B: 95:5 acetonitrile:water with 10 mM ammonium acetate; Temperature=50° C.; Products detected at 220 nm wavelength w/positive ionization mode.

Method I: Column: Waters Acquity BEH C18 2.1×50 mm 1.7 μm; Linear gradient of 0-100% Solvent B over 3 min, then 0.75 min hold at 100% B; Flow rate: 1.11 mL/min; Solvent A: 5:95 acetonitrile:water with 0.05% TFA; Solvent B: 95:5 acetonitrile:water with 0.05% TFA; Temperature=50° C.; Products detected at 220 nm wavelength w/positive ionization mode.

Method J: Column: PHENOMENEX®, 2.5μ, 2.0×30 mm; Mobile phase: 10-90% aq CH₃OH/0.1% TFA; Gradient=4.0 min. linear with 1.0 min. hold; Flow rate: 1 ml/min detected at 220 nm or 254 nm detection wavelength.

Method K: Column: Waters XBridge C18 4.6×50 mm 5μ; Linear gradient of 0-100% Solvent B over 4.0 min; Flow rate: 4 mL/min; Solvent A: 5:95 acetonitrile:H₂O with 0.05% TFA; Solvent B: 5:95 H$_2$O: acetonitrile with 0.05% TFA; Products detected at 220 nm wavelength w/positive ionization mode.

Method L (Shimadzu HPLC): Column: Waters Acquity BEH C18 2.0×50 mm, 1.7μ; Linear gradient of 0-100% Solvent B over 1.5 min; Flow rate: 1 mL/min; Solvent A: 90:10 Water: acetonitrile with 0.1% TFA; Solvent B: 90:10 acetonitrile: Water with 0.1% TFA; Products detected at 220 wavelength w/positive ionization mode.

Method M: (Waters HPLC); Column: Waters Acquity BEH C18 2.1×50 mm, 1.7μ; Linear gradient of 2-98% Solvent B over 1.0 min, hold at 98% B for 0.5 min; Flow rate: 0.8 mL/min; Solvent A: H$_2$O with 0.05% TFA; Solvent B: Acetonitrile with 0.05% TFA; Products detected at 220 nm wavelength w/positive ionization mode.

Method N: Column: Waters XBridge C18 4.6×50 mm 5μ; Linear gradient of 0-100% Solvent B over 4.0 min; Flow rate: 4 mL/min; Solvent A: 5:95 ACN:H$_2$O with 10 mM NH$_4$OAc; Solvent B: 5:95 H$_2$O:ACN with 10 mM NH$_4$OAc; Products detected at 220 nm wavelength w/positive ionization mode.

Method P: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Intermediate N1

7-Bromo-5-(1-(tetrahydro-2H-pyran-4-yl)-1H-pyrazol-5-yl)pyrrolo[2,1-f][1,2,4]triazin-4-amine

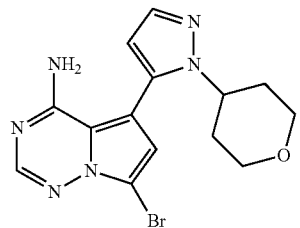

(N1)

Intermediate N1-A: 1-(4-Amino-7-bromopyrrolo[2,1-f][1,2,4]triazin-5-yl)-3-(trimethylsilyl)prop-2-yn-1-one

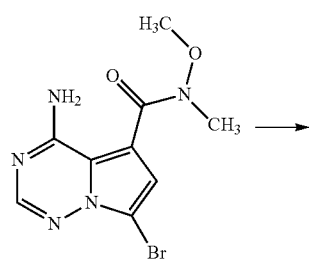

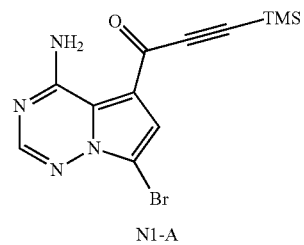

N1-A

To a solution of ethynyltrimethylsilane (0.83 mL, 5.9 mmol) in THF (15 mL) at −78° C. was added n-butyllithium (2.27 mL, 5.68 mmol) dropwise. After stirring for 5 min at −78° C., 4-amino-7-bromo-N-methoxy-N-methylpyrrolo[2,1-f][1,2,4]triazine-5-carboxamide (0.59 g, 1.96 mmol, for preparation see WO 2011/123493) as a solution in THF (3 mL). After 30 min, AcOH (0.3 mL) was added to give a bright yellow solution. The mixture was partitioned between ethyl acetate (20 mL) and water (10 mL). The organic layer was washed with brine, dried over sodium sulfate and concentrated to afford Intermediate N1-A (0.66 g) as a yellow solid. The material was used without further purification.

Intermediate N1

Intermediate N1-A (3.2 g, 9.49 mmol) was suspended in ethanol (123 mL) and (tetrahydro-2H-pyran-4-yl)hydrazine, HCl salt (2.90 g, 18.98 mmol) was added. The suspension was stirred vigorously for 2 min and triethylamine (6.61 ml, 47.4 mmol) was added. The mixture was refluxed for 18 h, cooled to room temperature and water (50 mL) was added. The mixture was concentrated to 50 mL and the solid formed was filtered, dried in vacuo providing 7-bromo-5-(1-(tetrahydro-2H-pyran-4-yl)-1H-pyrazol-5-yl)pyrrolo[2,1-f][1,2,4]triazin-4-amine (N1) (3.24 g, 94% yield) as a white solid. $^1$H NMR (400 MHz, DMSO-d$_6$) δ 8.06 (s, 1H), 7.65 (d, J=1.5 Hz, 1H), 7.04 (s, 1H), 6.42 (d, J=1.8 Hz, 1H), 4.33-4.23 (m, 1H), 3.87 (dd, J=11.2, 3.5 Hz, 2H), 3.37-3.31 (m, 2H), 2.06 (qd, J=12.2, 4.7 Hz, 2H), 1.84-1.68 (m, 2H). LC/MS: Rt=0.69 min; [M+1]$^+$=363, 365 (Method M).

Intermediate N-2

7-Bromo-5-(1-cyclohexyl-1H-pyrazol-5-yl)pyrrolo[2,1-f][1,2,4]triazin-4-amine

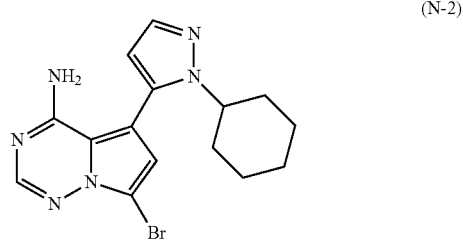 [SMILES: Nc1ncnn2c(Br)cc(-c3ccnn3C3CCCCC3)c12]

(N-2)

1-(4-Amino-7-bromopyrrolo[2,1-f][1,2,4]triazin-5-yl)-3-(trimethylsilyl)prop-2-yn-1-one (0.95 g, 6.7 mmol) was suspended in ethanol (24 mL) and cyclohexylhydrazine, HCl (1.01 g, 18.98 mmol) was added followed by triethylamine (1.5 mL, 10.7 mmol). The mixture was heated at 90° C. for 2 h, cooled to room temperature and added EtOAc (50) mL and washed with water, brine, dried over $Na_2SO_4$, filtered and concentrated. The solid obtained was purified by silica gel chromatography eluting with a gradient of 0-10% methanol in DCM to obtain the desire product (0.86 g) as a white solid. m/z 361, 363.

The following Intermediates were prepared using the procedure described for the synthesis of Intermediates N1 and N2 using an appropriate hydrazine reagent.

Intermediate R1-A: 7-Bromo-5-iodopyrrolo[2,1-f][1,2,4]triazin-4-amine

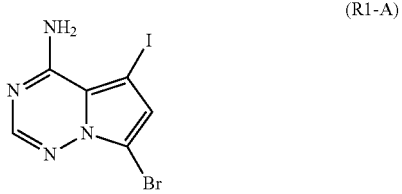 [SMILES: Nc1ncnn2c(Br)cc(I)c12]

(R1-A)

To a solution of 7-bromopyrrolo[2,1-f][1,2,4]triazin-4-amine (4 g, 18.78 mmol) in anhydrous DMF (200 mL) was added NIS (4.65 g, 20.65 mmol) and the mixture was stirred in the dark at room temperature for 10 h. The precipitate formed was filtered and washed with DCM (3×), and dried to provide white solid, 7-bromo-5-iodopyrrolo[2,1-f][1,2,4]

TABLE 1

| Intermediate | R | Name | LC/MS [M + 1] Method |
|---|---|---|---|
| N3 | cyclohexyl | 7-bromo-5-(1-cyclohexyl-1H-pyrazol-5-yl)pyrrolo[1,2-f][1,2,4]triazin-4-amine | 361.0, 363.0 (Method M) |
| N4 | cyclopropyl | 17-bromo-5-(1-cyclopropyl-1H-pyrazol-5-yl)pyrrolo[2,1-f][1,2,4]triazin-4-amine | 319.0, 321.0 (Method M) |
| N5 | $CH_2CF_3$ | 7-bromo-5-(1-(2,2,2-trifluoroethyl)-1H-pyrazol-5-yl)pyrrolo[2,1-f][1,2,4]triazin-4-amine | 361.0, 363.0 (Method M) |

Intermediate R1

7-Bromo-5-(1-(tetrahydro-2H-pyran-4-yl)-1H-1,2,3-triazol-5-yl)pyrrolo[2,1-f][1,2,4]triazin-4-amine triazin-4-amine (5 g, 79% yield). LC-MS m/z (M+H)$^+$=339.95. $^1$H NMR (500 MHz, DMSO-$d_6$) δ 7.10 (S, 1H), 7.98 (s, 1H).

Intermediate R1-B: 7-Bromo-5-((trimethylsilyl)ethynyl)pyrrolo[2,1-f][1,2,4]triazin-4-amine

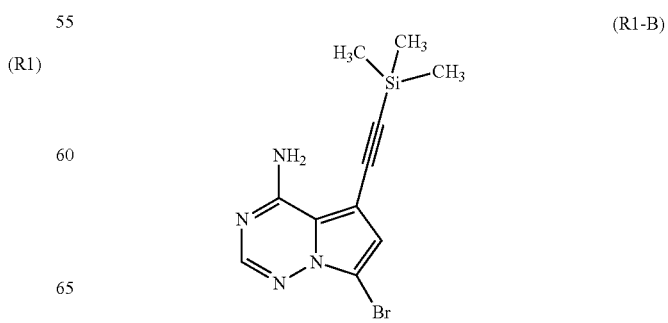

7-Bromo-5-iodopyrrolo[2,1-f][1,2,4]triazin-4-amine (2.4 g, 7.08 mmol) was suspended in anhydrous DMF (40 mL), and then triethylamine (3 mL, 21.24 mmol), copper(I) iodide (0.3 g, 1.56 mmol), bis(triphenylphosphine)palladium(II) chloride (0.5 g, 0.71 mmol) were added. Nitrogen gas was bubbled through the mixture for a 3 min and ethynyltrimethylsilane (1 mL, 7.1 mmol) was added. After stirring for 1 h, the reaction mixture was poured into ice water (200 mL) and the precipitate which formed was filtered. The solid was dissolved in ether (150 mL), washed with water (100 mL) followed by brine (100 mL). The crude solid was then suspended in MeOH (50 mL), stirred for an hour and then filtered and dried in vacuo to provide 7-bromo-5-((trimethylsilyl)ethynyl)pyrrolo[2,1-f][1,2,4]triazin-4-amine (90% yield). LC-MS m/z (M+H)$^+$=309.10. $^1$H NMR (500 MHz, DMSO-d$_6$) δ 2.50 (s, 9H), 7.05 (S, 1H), 8.03 (s, 1H).

Intermediate R1-C: 7-Bromo-5-ethynylpyrrolo[2,1-f][1,2,4]triazin-4-amine

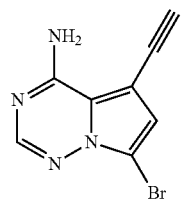

(R1-C)

To a suspension of 7-bromo-5-((trimethylsilyl)ethynyl)pyrrolo[2,1-f][1,2,4]triazin-4-amine (7.3 g, 23.61 mmol) in MeOH (100 mL) was added K$_2$CO$_3$ (16.31 g, 118 mmol) and the reaction mixture was stirred for 2 h at room temperature. Suspension was filtered, washed with water and DCM. The light yellow solid was dried in vacuo. The combined filtrate was concentrated and the solid was washed with DCM to provide more of yellow solid which was combined with the previous solid to provide 7-bromo-5-ethynylpyrrolo[2,1-f][1,2,4]triazin-4-amine (5.3 g, 95% yield). LCMS (M+H)$^+$=237.05. $^1$H NMR (500 MHz, DMSO-d$_6$) δ 4.48 (s, 1H), 7.05 (S, 1H), 8.01 (s, 1H).

Intermediate R1:

To a solution of 7-bromo-5-ethynylpyrrolo[2,1-f][1,2,4]triazin-4-amine (200 mg, 0.844 mmol) in toluene (8 mL) was added 4-azidotetrahydro-2H-pyran (215 mg, 1.7 mmol) and then chloro(pentamethylcyclopentadienyl)ruthenium(II) tetramer (27 mg, 0.025 mmol). Nitrogen was bubbled through the mixture for 1 min, and the mixture was heated in a sealed tube at 100° C. for 50 min in a microwave instrument. The mixture was cooled, diluted with hexane (8 mL) and the precipitate formed was filtered, washed with hexane, and MeOH and dried in vacuo to provide 7-bromo-5-(1-(tetrahydro-2H-pyran-4-yl)-1H-1,2,3-triazol-5-yl)pyrrolo[2,1-f][1,2,4]triazin-4-amine (250 mg, 81% yield). LC/MS (M+H)$^+$=364.1. $^1$H NMR (500 MHz, DMSO-d$_6$) δ 1.95 (m, 2H), 2.14 (m, 2H), 3.40 (m, 2H), 3.92 (m, 2H), 4.51 (m, 1H), 7.08 (S, 1H), 7.83 (S, 1H), 8.10 (s, 1H).

The following Intermediates were prepared according to the general synthesis procedure for Intermediate R1 using appropriate azides in the last step.

TABLE 2

| Intermediate | Q$_1$ | Name |
|---|---|---|
| R2 | 1-isopropyl-1H-1,2,3-triazol-5-yl | 7-bromo-5-(1-isopropyl-1H-1,2,3-triazol-5-yl)pyrrolo[2,1-f][1,2,4]triazin-4-amine |
| R3 | 1-cyclohexyl-1H-1,2,3-triazol-5-yl | 7-bromo-5-(1-cyclohexyl-1H-1,2,3-triazol-5-yl)pyrrolo[2,1-f][1,2,4]triazin-4-amine |

Intermediate RX

7-Bromo-5-(1-methyl-1H-pyrazol-4-yl)pyrrolo[1,2-f][1,2,4]triazin-4-amine

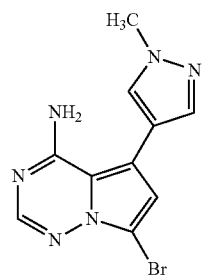

(RX)

TABLE 3

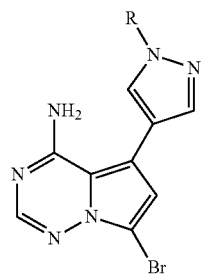

| Intermediate | R | Name | LCMS M + H |
|---|---|---|---|
| RXC | —CH(CH$_3$)$_2$ | 7-bromo-5-(1-isopropyl-1H-pyrazol-4-yl)pyrrolo[1,2-f][1,2,4]triazin-4-amine | 321 and 323 |

TABLE 4

| Intermediate | Structure | Name | LCMS M + H |
|---|---|---|---|
| RXK | 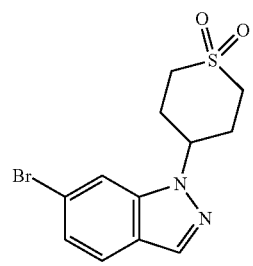 | N-(5-(4-amino-7-bromopyrrolo[1,2-f][1,2,4]triazin-5-yl)pyridin-2-yl)acetamide | 347 and 349 |

A mixture of 7-bromo-5-iodopyrrolo[2,1-f][1,2,4]triazin-4-amine (462 mg, 1.2 mmol) (Intermediate R1-A), 1-methyl-4-(4,4,5,5-tetramethyl-1,3,2-dioxaborolan-2-yl)-1H-pyrazole (250 mg, 1.200 mmol), sodium carbonate (2.400 mL, 4.80 mmol), water (0.5 mL) and DMF (1.5 mL) was placed in a capped microwave pressure reaction vial. The mixture was sparged with nitrogen via hypodermic needles for 5 min and then heated at 90° C. for 5 min. A solution of 1,1'-bis(diphenylphosphino)ferrocene-palladium (II) dichloride dichloromethane complex (196 mg, 0.240 mmol) in DMF (0.2 mL) was added and the mixture stirred at 90° C. for 10 min. Flash chromatography using a 24 g Isco silica gel cartridge eluted with EtOAc/hexanes gave 7-bromo-5-(1-methyl-1H-pyrazol-4-yl)pyrrolo[2,1-f][1,2,4]triazin-4-amine (205 mg, 0.699 mmol, 58% yield) as a light yellow solid. Mass spectrum m/z 293 (M+H)$^+$. $^1$H NMR (400 MHz, DMSO-d$_6$) δ 7.96 (s, 1H), 7.88 (s, 1H), 7.58 (d, J=0.9 Hz, 1H), 6.80 (s, 1H), 3.89 (s, 3H).

The Intermediates in Tables JATR1 and JATR2 were prepared by chemistry exemplified in RX from Intermediate R1-A and available boronic esters or boronic acids. Alternatively, the boronic esters can be prepared by methods known in the art.

Intermediate R14

4-(6-Bromo-1H-indazol-1-yl)tetrahydro-2H-thiopyran 1,1-dioxide (R14)

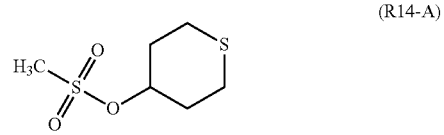

Intermediate R14-A: Tetrahydro-2H-thiopyran-4-yl methanesulfonate (R14-A)

A mixture of tetrahydro-2H-thiopyran-4-ol (1.65 g, 13.96 mmol), methanesulfonyl chloride (2.176 ml, 27.9 mmol), Et₃N (5.84 ml, 41.9 mmol) in CH₂Cl₂ (60 ml) and was stirred at room temperature overnight. The reaction mixture was poured into ice-water and the aqueous phase was extracted with EtOAc (3×10 mL). The combined organic phase was washed with brine (10 mL), and dried over Na₂SO₄, and concentrated to yield colorless oil, tetrahydro-2H-thiopyran-4-yl methanesulfonate (2.15 g, 78% yield). $^1$H NMR (500 MHz, CDCl₃) δ 2.13 (s, 2H), 2.24 (m, 2H), 2.61 (m, 2H), 2.86 (m, 2H), 3.70 (s, 3H), 4.81 (m, 1H).

Intermediate R14-B: 6-Bromo-1-(tetrahydro-2H-thiopyran-4-yl)-1H-indazole

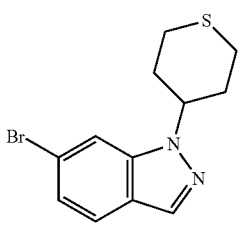

(R14-B)

To a solution of 6-bromo-1H-indazole (200 mg, 1.015 mmol) in DMF (6 mL) were added tetrahydro-2H-thiopyran-4-yl methanesulfonate (398 mg, 2.0 mmol) and K₂CO₃ (351 mg, 2.54 mmol) and the reaction mixture was heated at 100° C. for 18 h. LC/MS indicated the presence of two isomers. The reaction complex was filtered and washed with EtOAc (20 mL). The filtrate was diluted with water (20 mL) and the organic layer was separated, dried over Na₂SO₄ and concentrated. The residue was purified by Isco silica gel column chromatography (12 g column, 0-100% 0-100% EtOAc/hexane solvent, 20 min gradient) to provide 6-bromo-1-(tetrahydro-2H-thiopyran-4-yl)-1H-indazole (70 mg, 0.236 mmol, 23.20% yield) and 6-bromo-2-(tetrahydro-2H-thiopyran-4-yl)-2H-indazole (34 mg, 0.114 mmol, 11.27% yield). Both: LCMS (M+H)⁺=297.1, 299.1 (1:1 ratio).

Intermediate R14

To a solution of 6-bromo-1-(tetrahydro-2H-thiopyran-4-yl)-1H-indazole (70 mg, 0.236 mmol) in DCM (4 mL) was added mCPBA (81 mg, 0.471 mmol) at 0° C. The reaction mixture was stirred for 1 h, saturated NaHCO₃ (10 mL) was added and the mixture was extracted with DCM (3×10 mL). The combined organic layers were washed with sodium metabisulfite, brine (10 mL), dried over MgSO₄, and concentrated. It was purified by Isco silica gel column (12 g column, 0-100% 0-100% EtOAc/hexane solvent, 20 min grad) to afford 4-(6-bromo-1H-indazol-1-yl)tetrahydro-2H-thiopyran 1,1-dioxide (62 mg, 0.188 mmol, 80% yield). LC/MS (M+H)⁺=329.05, 331.1 (1:1 ratio).

Intermediate R15

6-Bromo-1-(tetrahydro-2H-pyran-4-yl)-1H-indazole

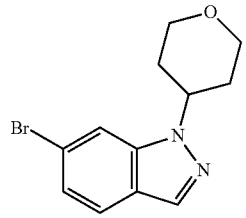

(R15)

To a solution of 6-bromo-1H-indazole (200 mg, 1.015 mmol) in DMF (10 mL) was added tetrahydro-2H-pyran-4-yl methanesulfonate (274 mg, 1.523 mmol), TBAI (37.5 mg, 0.102 mmol) and K₂CO₃ (351 mg, 2.54 mmol). The reaction mixture was heated at 120° C. for 14 h. The mixture was cooled to room temperature, diluted with EtOAc (20 mL), and washed with H₂O (20 mL). The orange organic layer was washed with brine, dried over with MgSO₄, then concentrated to give crude product, which was purified by flash chromatography on silica gel eluting with 0-100% EtOAc/hexane (12 g column, 16 min gradient) to afford two regioisomers. 6-Bromo-1-(tetrahydro-2H-pyran-4-yl)-1H-indazole (114 mg, 40% yield). LCMS (M+H)⁺=281.15. $^1$H NMR (500 MHz, CDCl₃) δ 2.27 (m, 4H), 3.62 (m, 2H), 4.19 (m, 2H), 4.66 (m, 1H), 7.19 (dd, 1H), 7.56 (dd, 1H), 7.91 (s, 1H), 7.98 (s, 1H).

Intermediate R16

6-Bromo-1-(cyclopropylmethyl)-1H-indazole

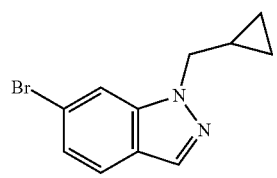

(R16)

To a solution of 6-bromo-1H-indazole (150 mg, 0.761 mmol) in acetonitrile (10 mL), (bromomethyl)cyclopropane (0.219 ml, 2.284 mmol), potassium carbonate (316 mg, 2.284 mmol) and tetrabutylammonium iodide (22.50 mg, 0.061 mmol) were added. The mixture was heated and stirred at 80° C. for 10 h, then cooled to room temperature, diluted with EtOAc (20 mL), and washed with H₂O (20 mL). The orange organic layer was washed with brine, dried over with MgSO₄, then concentrated to give crude product, which was purified by flash chromatography on silica gel eluting with 0-100% EtOAc/hexane (12 g column, 16 min gradient). Two isomers were separated to provide 6-bromo-1-(cyclopropylmethyl)-1H-indazole (84.5 mg, 0.336 mmol, 44.2% yield): LCMS (M+H)⁺=344.15, 346.10 (1:1 ratio). $^1$H NMR (500 MHz, MeOD) δ 0.43 (m, 2H), 0.57 (m, 2H), 1.32 (m, 1H), 2.30 (d, 2H), 7.28 (dd, 1H), 7.69 (d, 1H), 7.87 (s, 1H), 8.02 (s, 1H), and 6-bromo-2-(cyclopropylmethyl)-2H-indazole (63 mg, 0.251 mmol, 33.0% yield).

The Intermediates in Table 5 were prepared according to the general synthesis processes for Intermediates R14, R15 and R16, utilizing appropriate starting materials.

TABLE 5

| Intermediate | Structure | Name |
|---|---|---|
| R17 | 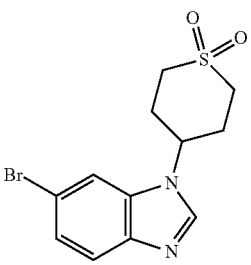 | 4-(6-bromo-1H-benzo[d]imidazol-1-yl)tetrahydro-2H-thiopyran 1,1-dioxide |
| R18 | 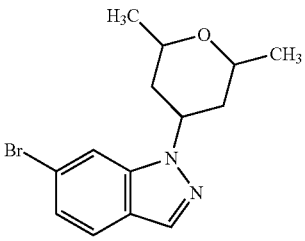 | 6-bromo-1-(2,6-dimethyltetrahydro-2H-pyran-4-yl)-1H-indazole |
| R19 | 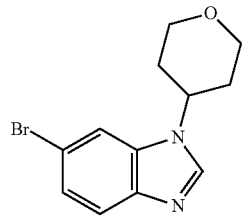 | 6-bromo-1-(tetrahydro-2H-pyran-4-yl)-1H-benzo[d]imidazole |
| R21 | 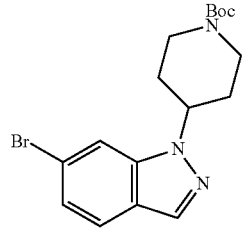 | tert-butyl 4-(6-bromo-1H-indazol-1-yl)piperidine-1-carboxylate |
| R23 | 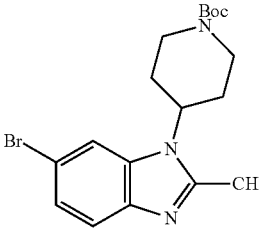 | tert-butyl 4-(6-bromo-2-methyl-1H-benzo[d]imidazol-1-yl)piperidine-1-carboxylate |
| R24 | 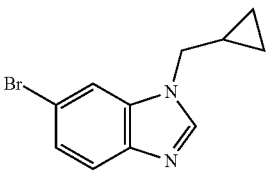 | 6-bromo-1-(cyclopropylmethyl)-1H-benzo[d]imidazole |

TABLE 5-continued

| Intermediate | Structure | Name |
|---|---|---|
| R25 | 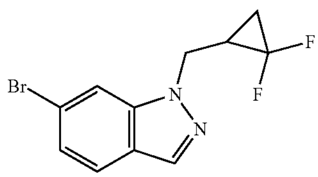 | 6-bromo-1-((2,2-difluorocyclopropyl)methyl)-1H-indazole |
| R26 | 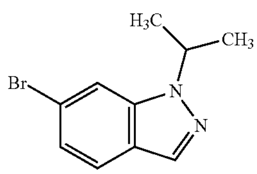 | 6-bromo-1-isopropyl-1H-indazole |
| R27 | 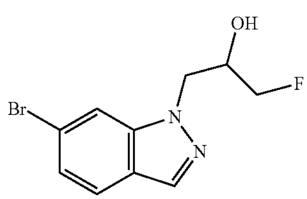 | 1-(6-bromo-1H-indazol-1-yl)-3-fluoropropan-2-ol |

Intermediate R31

4-(5-Bromopyridin-3-yl)thiomorpholine 1,1-dioxide

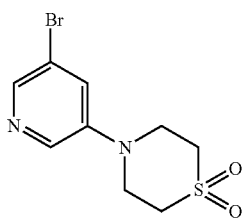

(R31)

To a 20 mL microwave reactor vial was added thiomorpholine 1,1-dioxide (200 mg, 1.47 mmol), 3,5-dibromopyridine (701 mg, 2.96 mmol), $Cs_2CO_3$ (1.2 g, 3.7 mmol) and toluene (5 mL). The vessel was purged and degassed with N2, then 2,2'-bis(diphenylphosphino)-1,1'-binaphthalene (138 mg, 0.222 mmol) and palladium(II) acetate (66.4 mg, 0.296 mmol) were added and degassing with N2 was repeated. The reaction vessel was capped and the mixture was stirred at 110° C. overnight. The reaction mixture was cooled, filtered and washed with MeOH and the filtrate was concentrated. The residue was purified by preparative LC method C to provide 4-(5-bromopyridin-3-yl) thiomorpholine 1,1-dioxide (154 mg, 35.8%). LC/MS $(M+H)^+=291.05$, 293.05 (1:1 ratio).

The Intermediates in Table 6 were prepared according to the general synthesis procedures for the Intermediates described above, using the appropriate starting material.

TABLE 6

| Intermediate | Structure | Name |
|---|---|---|
| R32 | 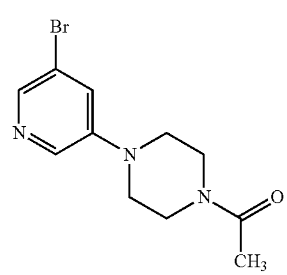 | 1-(4-(5-bromopyridin-3-yl)piperazin-1-yl)ethanone |

TABLE 6-continued

| Intermediate | Structure | Name |
|---|---|---|
| R33 | 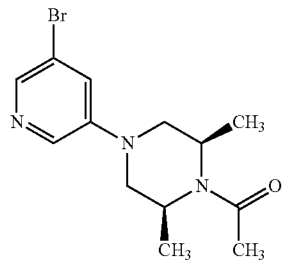 | 1-((cis)-4-(5-bromopyridin-3-yl)-2,6-dimethylpiperazin-1-yl)ethanone |
| R34 | 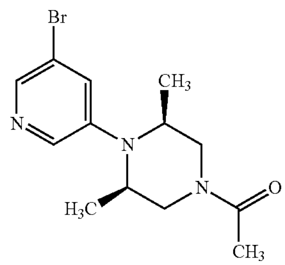 | 1-((cis)-4-(5-bromopyridin-3-yl)-3,5-dimethylpiperazin-1-yl)ethanone |
| R35 | 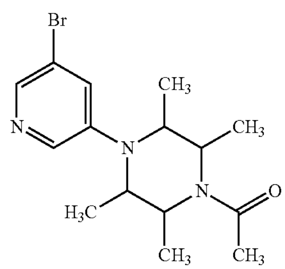 | 1-(4-(5-bromopyridin-3-yl)-2,3,5,6-tetramethylpiperazin-1-yl)ethanone |

Intermediate M3

4-Amino-7-bromopyrrolo[1,2-f][1,2,4]triazine-5-carbonitrile

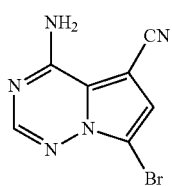

(M3)

4-Amino-7-bromopyrrolo[2,1-f][1,2,4]triazine-5-carbonitrile was prepared by nitrogenation of 7-bromo-5-ethynylpyrrolo[2,1-f][1,2,4]triazin-4-amine using the method described in Angew. Chem. Int. Ed., 52:6677-6680 (2013).

A mixture of 7-bromo-5-ethynylpyrrolo[2,1-f][1,2,4]triazin-4-amine (470 mg, 1.98 mmol) (intermediate R1-C), azidotrimethylsilane (457 mg, 3.97 mmol), silver carbonate (54.7 mg, 0.198 mmol) and DMSO (10 mL) was placed in a pressure reaction vial, the vial flushed with nitrogen and the mixture stirred at 100° C. for 15 h. The mixture was cooled to room temperature, and diluted with water (100 mL) under vigorous stirring. The mixture was filtered to collect the product which was washed with water and ether and sucked dry to give crude 4-amino-7-bromopyrrolo[2,1-f][1,2,4]triazine-5-carbonitrile (400 mg). This product was used in subsequent preparations without further purification. $^1$H NMR (400 MHz, DMSO-$d_6$) δ 8.19 (s, 1H), 7.50 (s, 1H).

An alternate preparation of M3:

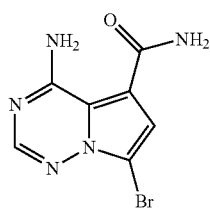

(M3-A)

M3-A: 4-Amino-7-bromopyrrolo[2,1-f][1,2,4]triazine-5-carboxamide

A suspension of ethyl 4-amino-7-bromopyrrolo[2,1-f][1,2,4]triazine-5-carboxylate (5.3 g, 18.59 mmol), THF (40 mL), MeOH (20 mL) and lithium hydroxide monohydrate (4.68 g, 112 mmol) dissolved in water (20 mL) was stirred at room temperature for 15 h and 50° C. for 1 h. The mixture was cooled to room temperature made acidic (pH=2) by dropwise addition of conc. HCl, diluted with water (200 mL) and the white precipitate collected by filtration. The product was washed with water and sucked dry and then dried further by rotovaping a suspension of the solid in 20% MeOH/toluene (2×100 mL).

The product from above was treated with DMF (40 mL) and DIPEA (19.48 mL, 112 mmol) and stirred for 5 min until most of the solid had dissolved. 1-Hydroxy-7-azabenzotriazole (3.80 g, 27.9 mmol) and 1-(3-dimethylaminopropyl)-3-ethylcarbodiimide hydrochloride (5.35 g, 27.9 mmol) were added to the mixture, the resulting yellow mixture was stirred for 5 min and then treated with ammonium chloride (3.98 g, 74.4 mmol) and stirred at room temperature for 16 h. The mixture was diluted with water (20 mL), stirred for 5 min and filtered to collect the precipitate. The collected solid was washed with saturated $NaHCO_3$ (100 mL) and water (200 mL), sucked dry and the dried further in vacuo to give 4-amino-7-bromopyrrolo[2,1-f][1,2,4]triazine-5-carboxamide as a white solid (4.5 g, 95%). LC-MS: m/z=255.8, $(M+H)^+$. $^1$H NMR (400 MHz, DMSO-$d_6$) δ 10.41 (br. s., 1H), 8.24 (br. s., 1H), 8.11 (br. s., 1H), 8.01 (s, 1H), 7.67 (br. s., 1H), 7.48 (s, 1H). LC-MS: m/z=255.8, $(M+H)^+$.

Intermediate M3

4-Amino-7-bromopyrrolo[2,1-f][1,2,4]triazine-5-carboxamide (1.0 g, 3.91 mmol) was placed in a 20 mL BIOTAGE® pressure reaction vial, treated with phosphorus oxychloride (7.28 ml, 78 mmol), the vial capped and heated for 20 h in a 120° C. heating block. The resulting brown mixture was cooled to room temperature and poured slowly in 2 M NaOH (75 mL) cooled to 0° C. keeping the temperature below 35° C. The resulting was stirred for 10 min and then made basic to pH 7.5 with 5 M NaOH. The mixture was filtered to collect the yellow solid which was washed with water, sucked dry and dried in vacuo. The filtrate was kept at room temperature overnight after which time more of the product predicated. The second crop was collected, washed with water, dried and combined with the first crop to give 4-amino-7-bromopyrrolo[2,1-f][1,2,4]triazine-5-carbonitrile (0.68 g, 73% yield). LC-MS: m/z=237.8, $(M+H)^+$. $^1$H NMR (400 MHz, DMSO-$d_6$) δ 8.19 (s, 1H), 7.50 (s, 2H); $^{13}$C NMR (125 MHz, DMSO-$d_6$) δ 154.4; 150.3; 119.2; 114.7; 102.5; 84.1.

Intermediate M4

7-Bromo-5-chloropyrrolo[1,2-f][1,2,4]triazin-4-amine

(M4)

To a solution of 7-bromopyrrolo[2,1-f][1,2,4]triazin-4-amine (0.48 g, 2.253 mmol) in DMF (11.27 ml) was added NCS (0.361 g, 2.70 mmol) and the reaction mixture was stirred at room temperature for 2 days and was monitored by LCMS. The reaction mixture was partitioned between 1.5M $K_2HPO_4$ and EtOAc. The organic phase was washed with 10% LiCl, brine, dried by $Na_2SO_4$, filtered, and concentrated to afford a white solid as the crude product. The crude product was then purified by ISCO column (24 g, 30-50-75% of EtOAc in hexane). The desired product was obtained as a white solid (0.48 g) in 86% yield. Mass spectrum m/z 246.8, 248.8, 250.8 $(M+H)^+$. $^1$H NMR (400 MHz, DMSO-$d_6$) δ 8.17 (d, J=8.4 Hz, 1H), 7.93 (s, 1H), 7.21-7.00 (m, 1H), 6.98 (s, 1H).

Example 1

1-(4-(5-(4-Amino-5-(1-(tetrahydro-2H-pyran-4-yl)-1H-pyrazol-5-yl)pyrrolo[2,1-f][1,2,4]triazin-7-yl)pyridin-3-yl)piperazin-1-yl)ethanone, TFA

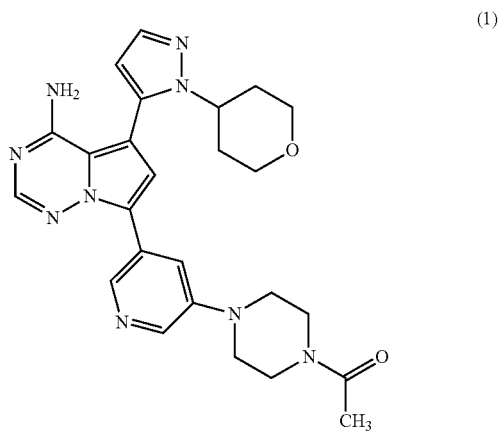 [SMILES: CC(=O)N1CCN(c2cncc(-c3cc(-c4ccnn4C4CCOCC4)c4c(N)ncnn34)c2)CC1]

(1)

In a microwave vial 1-(4-(5-bromopyridin-3-yl)piperazin-1-yl)ethanone, TFA salt (Intermediate R32) (70 mg, 0.176 mmol) was combined with 4,4,4',4',5,5,5',5'-octamethyl-2,2'-bi(1,3,2-dioxaborolane) (44.6 mg, 0.176 mmol), potassium acetate (62.7 mg, 0.639 mmol), $PdCl_2(dppf)$-$CH_2Cl_2$ adduct (19.58 mg, 0.024 mmol) and dioxane (5 mL). Argon was bubbled through the mixture while sonicating to degas. The vial was sealed and the reaction mixture was reacted in a microwave for 30 min at 120° C. to give the boronic ester intermediate. To the reaction mixture was added water (0.5 mL), 7-bromo-5-(1-(tetrahydro-2H-pyran-4-yl)-1H-pyrazol-5-yl)pyrrolo[2,1-f][1,2,4]triazin-4-amine (Intermediate N1) (58.0 mg, 0.160 mmol), sodium carbonate (0.240 mL, 0.240 mmol, 1 M aqueous solution) and additional $PdCl_2(dppf)$-$CH_2Cl_2$ adduct (19.58 mg, 0.024 mmol). The mixture was reacted in the microwave at 120° C. for 40 min to give the desired final product as the major product. The mixture was diluted with 5 mL of water, extracted with EtOAc (10 mL×2), the organic layers were concentrated and the residue purified by preparative HPLC (using Method B twice: first run with a 19×200 mm column) to provide 1-(4-(5-(4-amino-5-(1-(tetrahydro-2H-pyran-4-yl)-1H-pyrazol-5-yl) pyrrolo[2,1-f][1,2,4]triazin-7-yl)pyridin-3-yl) piperazin-1-yl) ethanone, TFA (17 mg, 15% yield). LC/MS $(M+H)^+$=489.10. $^1$H NMR (400 MHz, MeOD) δ 1.87 (m, 2H), 2.32 (m, 4H), 3.37 (s, 2H), 3.59 (m, 2H), 3.62 (m, 4H), 3.82 (m, 4H), 4.02 (m, 1H), 4.41 (m, 1H), 6.53 (d, 1H), 7.56 (s, 1H), 7.74 (d, 1H), 8.13 (s, 1H), 8.40 (d, 1H), 8.71 (m, 1H), 9.08 (s, 1H).

The Examples in Table 7 were prepared from Intermediate N3 following the general procedure for the synthesis of Example 1. In some examples $K_3PO_4$ was used in place of $K_2CO_3$. LCMS Method B was used for detection of product formation.

TABLE 7

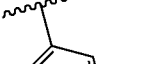

| Ex. No. | Q₂ | Name | LCMS (M + H)⁺ |
|---|---|---|---|
| 2 |  | 5-(4-amino-5-(1-cyclohexyl-1H-pyrazol-5-yl) pyrrolo[2,1-f][1,2,4]triazin-7-yl)-1H-benzo[d]imidazol-2(3H)-one | 415.3 |
| 3 | 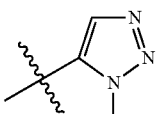 | 5-(1-cyclohexyl-1H-pyrazol-5-yl)-7-(1-methyl-1H-benzo[d]imidazol-6-yl)pyrrolo[2,1-f][1,2,4]triazin-4-amine | 413.3 |

The Examples in Table 8 were synthesized according to the general synthetic procedure described for the synthesis of Example 1, using appropriate commercial materials and Intermediates R30 to R45.

TABLE 8

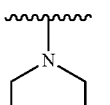

| Ex. No. | Q₁ | R₂ | Name | [M + H]⁺ | HPLC R$_t$ (min) [Method] |
|---|---|---|---|---|---|
| 4 | | | 1-(4-(5-(4-amino-5-(1-(tetrahydro-2H-pyran-4-yl)-1H-1,2,3-triazol-5-yl)pyrrolo[2,1-f][1,2,4]triazin-7-yl)pyridin-3-yl)piperazin-1-yl)ethanone, TFA | 489.10 | 0.92 [I] |

TABLE 8-continued

| Ex. No. | Q₁ | R₂ | Name | [M + H]⁺ | HPLC R$_t$ (min) [Method] |
|---|---|---|---|---|---|
| 5 | 1-isopropyl-1,2,3-triazol-5-yl | 4-acetylpiperazin-1-yl | 1-(4-(5-(4-amino-5-(1-isopropyl-1H-1,2,3-triazol-5-yl)pyrrolo[2,1-f][1,2,4]triazin-7-yl)pyridin-3-yl)piperazin-1-yl)ethanone, TFA | 447.20 | 0.74 [I] |
| 6 | 1-(tetrahydro-2H-pyran-4-yl)-1H-pyrazol-5-yl | thiomorpholine 1,1-dioxide | 4-(5-(4-amino-5-(1-(tetrahydro-2H-pyran-4-yl)-1H-pyrazol-5-yl)pyrrolo[2,1-f][1,2,4]triazin-7-yl)pyridin-3-yl)thiomorpholine 1,1-dioxide | 495.20 | 0.68 [I] |
| 7 | 1-(tetrahydro-2H-pyran-4-yl)-1H-1,2,3-triazol-5-yl | thiomorpholine 1,1-dioxide | 4-(5-(4-amino-5-(1-(tetrahydro-2H-pyran-4-yl)-1H-1,2,3-triazol-5-yl)pyrrolo[2,1-f][1,2,4]triazin-7-yl)pyridin-3-yl)thiomorpholine 1,1-dioxide | 496.10 | 0.65 [I] |
| 8 | 1-isopropyl-1,2,3-triazol-5-yl | thiomorpholine 1,1-dioxide | 4-(5-(4-amino-5-(1-isopropyl-1H-1,2,3-triazol-5-yl)pyrrolo[2,1-f][1,2,4]triazin-7-yl)pyridin-3-yl)thiomorpholine 1,1-dioxide | 454.10 | 0.72 [I] |
| 9 | 1-(tetrahydro-2H-pyran-4-yl)-1H-pyrazol-5-yl | cis-4-acetyl-2,6-dimethylpiperazin-1-yl | 1-((cis)-4-(5-(4-amino-5-(1-(tetrahydro-2H-pyran-4-yl)-1H-pyrazol-5-yl)pyrrolo[2,1-f][1,2,4]triazin-7-yl)pyridin-3-yl)-2,6-dimethylpiperazin-1-yl)ethanone | 516.30 | 0.82 [I] |
| 10 | 1-(tetrahydro-2H-pyran-4-yl)-1H-1,2,3-triazol-5-yl | cis-4-acetyl-2,6-dimethylpiperazin-1-yl | 1-((cis)-4-(5-(4-amino-5-(1-(tetrahydro-2H-pyran-4-yl)-1H-1,2,3-triazol-5-yl)pyrrolo[2,1-f][1,2,4]triazin-7-yl)pyridin-3-yl)-2,6-dimethylpiperazin-1-yl)ethanone | 517.20 | 0.80 [I] |

TABLE 8-continued

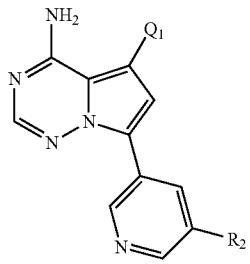

| Ex. No. | Q₁ | R₂ | Name | [M + H]⁺ | HPLC R$_t$ (min) [Method] |
|---|---|---|---|---|---|
| 11 | 5-pyrazolyl with tetrahydro-2H-pyran-4-yl | cis-3,5-dimethyl-4-acetylpiperazinyl | 1-((cis)-4-(5-(4-amino-5-(1-(tetrahydro-2H-pyran-4-yl)-1H-pyrazol-5-yl)pyrrolo[2,1-f][1,2,4]triazin-7-yl)pyridin-3-yl)-3,5-dimethylpiperazin-1-yl)ethanone | 516.20 | 0.86 [I] |
| 12 | 1,2,3-triazol-5-yl with tetrahydro-2H-pyran-4-yl | cis-3,5-dimethyl-4-acetylpiperazinyl | 1-((cis)-4-(5-(4-amino-5-(1-(tetrahydro-2H-pyran-4-yl)-1H-1,2,3-triazol-5-yl)pyrrolo[2,1-f][1,2,4]triazin-7-yl)pyridin-3-yl)-3,5-dimethylpiperazin-1-yl)ethanone | 517.20 | 0.78 [I] |
| 13 | 1-isopropyl-1,2,3-triazol-5-yl | cis-3,5-dimethyl-4-acetylpiperazinyl | 1-((cis)-4-(5-(4-amino-5-(1-isopropyl-1H-1,2,3-triazol-5-yl)pyrrolo[2,1-f][1,2,4]triazin-7-yl)pyridin-3-yl)-3,5-dimethylpiperazin-1-yl)ethanone | 475.15 | 0.968 [I] |
| 14 | 5-pyrazolyl with tetrahydro-2H-pyran-4-yl | 2,3,5,6-tetramethyl-4-acetylpiperazinyl | 1-(4-(5-(4-amino-5-(1-(tetrahydro-2H-pyran-4-yl)-1H-pyrazol-5-yl)pyrrolo[2,1-f][1,2,4]triazin-7-yl)pyridin-3-yl)-2,3,5,6-tetramethylpiperazin-1-yl)ethanone | 544.30 | 0.95 [I] |
| 15 | 1,2,3-triazol-5-yl with tetrahydro-2H-pyran-4-yl | 2,3,5,6-tetramethyl-4-acetylpiperazinyl | 1-(4-(5-(4-amino-5-(1-(tetrahydro-2H-pyran-4-yl)-1H-1,2,3-triazol-5-yl)pyrrolo[2,1-f][1,2,4]triazin-7-yl)pyridin-3-yl)-2,3,5,6-tetramethylpiperazin-1-yl)ethanone | 545.30 | 0.87 [I] |

Example 16

7-(1-(Tetrahydro-2H-pyran-4-yl)-1H-indazol-6-yl)-5-(1-(tetrahydro-2H-pyran-4-yl)-1H-pyrazol-5-yl) pyrrolo[2,1-f][1,2,4]triazin-4-amine

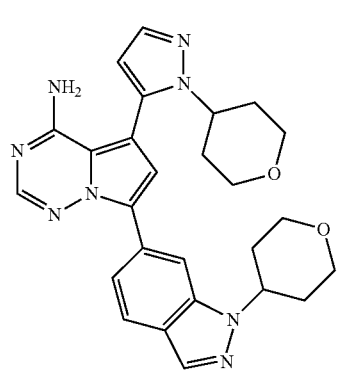

(16)

To a solution of 6-bromo-1-(tetrahydro-2H-pyran-4-yl)-1H-indazole (50 mg, 0.178 mmol) in dioxane (3 mL) was added 4,4,4',4',5,5,5',5'-octamethyl-2,2'-bi(1,3,2-dioxaborolane) (53.4 mg, 0.210 mmol), potassium acetate (63.5 mg, 0.647 mmol), and PdCl$_2$(dppf)-CH$_2$Cl$_2$ adduct (19.80 mg, 0.024 mmol). The microwave reaction vessel was degassed with N2 as described previously. The sealed reaction vessel was heated at 120° C. in a microwave for 30 min. To the cooled reaction mixture were added, water (1 mL), 7-bromo-5-(1-(tetrahydro-2H-pyran-4-yl)-1H-pyrazol-5-yl)pyrrolo[2,1-f][1,2,4]triazin-4-amine (58.7 mg, 0.162 mmol), sodium carbonate (243 mg, 0.243 mmol) and additional PdCl$_2$(dppf)-CH$_2$Cl$_2$ adduct (19.80 mg, 0.024 mmol). The sealed reaction vessel was degassed and heated at 120° C. in a microwave for 40 min. The reaction complex was filtered, washed with water, and extracted with ethyl acetate (20 mL×3). The organic layers were mixed, dried, concentrated and purified by preparative LCMS (PHENOMENEX® Luna Axia, C18, 5μ, 21.20×100 mm column; gradient elution 0-100% B/A over 18 min (Solvent A=10% MeCN/H$_2$O containing 0.1% TFA, Solvent B=90% MeCN/H$_2$O containing 0.1% TFA), flow rate 20 mL/min, UV detection at 220 nm) to obtain 7-(1-(tetrahydro-2H-pyran-4-yl)-1H-indazol-6-yl)-5-(1-(tetrahydro-2H-pyran-4-yl)-1H-pyrazol-5-yl)pyrrolo[2,1-f][1,2,4]triazin-4-amine (17.40 mg, 22% yield). LCMS (M+H)$^+$=485.30. $^1$H NMR (500 MHz, CDCl$_3$) δ 2.07 (m, 2H), 2.46 (m, 4H), 3.40 (t, 2H), 3.67 (t, 2H), 4.07 (m, 2H), 4.21 (m, 2H), 4.35 (m, 1H), 4.76 (m, 1H), 6.44 (d, 1H), 6.99 (s, 1H), 7.66 (d, 1H), 7.72 (d, 1H), 7.85 (d, 1H), 8.07 (s, 1H), 8.12 (s, 1H), 8.37 (d, 1H). $^{13}$C NMR (500 MHz, CDCl$_3$) δ 32.49, 33.10, 55.16, 55.33, 66.95, 67.29, 106.41, 107.80, 108.65, 113.13, 121.25, 121.41, 123.84, 127.60, 131.54, 132.99, 134.94, 138.84, 139.37, 147.77, 155.60.

Example 17

7-(1-(2-Fluoroethyl)-1H-indazol-6-yl)-5-(1-(tetrahydro-2H-pyran-4-yl)-1H-pyrazol-5-yl) pyrrolo[2,1-f][1,2,4]triazin-4-amine

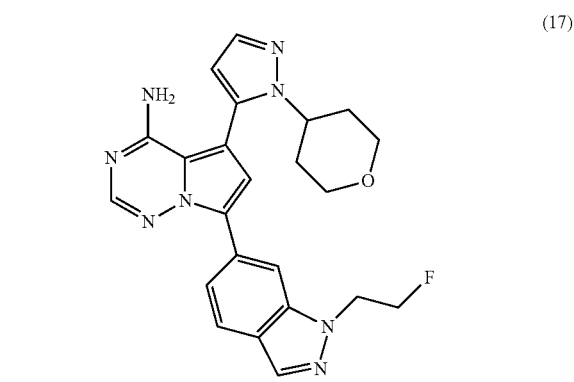 [SMILES: Nc1ncnn2c(-c3ccc4cnn(CCF)c4c3)cc(-c3ccnn3C3CCOCC3)c12]

(17)

Intermediate 17A: 7-(1H-Indazol-6-yl)-5-(1-(tetrahydro-2H-pyran-4-yl)-1H-pyrazol-5-yl) pyrrolo[2,1-f][1,2,4]triazin-4-amine

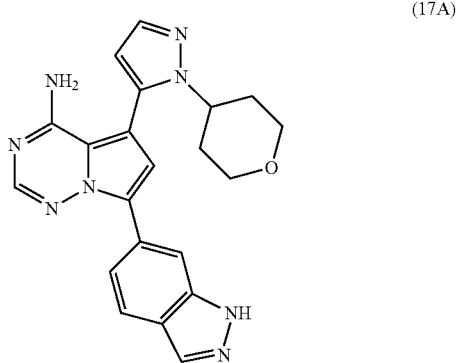 [SMILES: Nc1ncnn2c(-c3ccc4cn[nH]c4c3)cc(-c3ccnn3C3CCOCC3)c12]

(17A)

To a solution of 6-bromo-1H-indazole, TFA (300 mg, 0.964 mmol) in dioxane (10 mL) were added 4,4,4',4',5,5,5',5'-octamethyl-2,2'-bi(1,3,2-dioxaborolane) (289 mg, 1.14 mmol), potassium acetate (344 mg, 3.51 mmol), and PdCl$_2$(dppf)-CH$_2$Cl$_2$ adduct (107 mg, 0.132 mmol). The microwave reaction vessel was degassed with N2 as described previously. The sealed reaction vessel was heated at 120° C. in a microwave for 30 min. To the cooled reaction mixture were added, water (4 mL), 7-bromo-5-(1-(tetrahydro-2H-pyran-4-yl)-1H-pyrazol-5-yl)pyrrolo[2,1-f][1,2,4]triazin-4-amine (318 mg, 0.877 mmol), sodium carbonate (1.3 mL, 1.3 mmol, 1M) and additional PdCl$_2$(dppf)-CH$_2$Cl$_2$ adduct (107 mg, 0.132 mmol). The sealed reaction vessel was degassed and heated at 120° C. in a microwave for 40 min. The reaction complex was filtered, washed with water, and extracted with ethyl acetate (10 mL×3). The organic layers were mixed, dried, concentrated and purified by preparative LCMS (PHENOMENEX® Luna Axia, C18, 5μ, 21.20×100 mm column; gradient elution 0-100% B/A over 18 min (Solvent A=10% MeCN/H$_2$O containing 0.1% TFA, Solvent B=90% MeCN/H$_2$O containing 0.1% TFA), flow rate 20 mL/min, UV detection at 220 nm) to provide 7-(1H-indazol-6-yl)-5-(1-(tetrahydro-2H-pyran-4-yl)-1H-pyrazol-5-yl)pyrrolo[2,1-f][1,2,4]triazin-4-amine (240 mg, 0.599 mmol, 68.4% yield). LCMS (M+H)$^+$=401.30.

Example 17

To a solution of 7-(1H-indazol-6-yl)-5-(1-(tetrahydro-2H-pyran-4-yl)-1H-pyrazol-5-yl)pyrrolo[2,1-f][1,2,4]triazin-4-amine (20 mg, 0.05 mmol) in acetonitrile (2 mL), 1-bromo-2-fluoroethane (19 mg, 0.15 mmol), potassium carbonate (27.6 mg, 0.2 mmol) and tetrabutylammonium iodide (1.4 mg, 0.08 mmol) were added. The mixture was heated and stirred at 90° C. for 10 h. The mixture was cooled to room temperature, diluted with EtOAc (20 mL), and washed with H$_2$O (5 mL). The orange organic layer was washed with brine, dried over MgSO$_4$, and concentrated to give crude product, which was purified by preparative LCMS Method B. Two isomers were separated to obtain desired 7-(1-(2-fluoroethyl)-1H-indazol-6-yl)-5-(1-(tetrahydro-2H-pyran-4-yl)-1H-pyrazol-5-yl)pyrrolo[2,1-f][1,2,4]triazin-4-amine (4.1 mg, 18% yield). LCMS (M+H)$^+$=447.20. $^1$H NMR (500 MHz, DMSO-d$_6$) δ 1.82 (bs, 2H), 2.12 (m, 2H), 3.90 (m, 2H), 4.39 (m, 2H), 4.76 (m, 1H), 4.82 (m, 3H), 4.93 (m, 1H), 6.48 (d, 1H), 7.09 (s, 1H), 7.65 (d, 1H), 7.76 (s, 2H), 7.93 (d, 1H), 8.04 (bs, 1H), 8.13 (s, 1H), 8.21 (s, 1H).

Examples 18 and 19

5-(6-(4-Amino-5-(1-(tetrahydro-2H-pyran-4-yl)-1H-pyrazol-5-yl)pyrrolo[2,1-f][1,2,4]triazin-7-yl)-1H-indazol-1-yl)-1-methylpyridin-2(1H)-one (18), and 5-(6-(4-Amino-5-(1-(tetrahydro-2H-pyran-4-yl)-1H-pyrazol-5-yl)pyrrolo[2,1-f][1,2,4]triazin-7-yl)-1H-indazol-1-yl)-1-methylpiperidin-2-one (19)

(18)

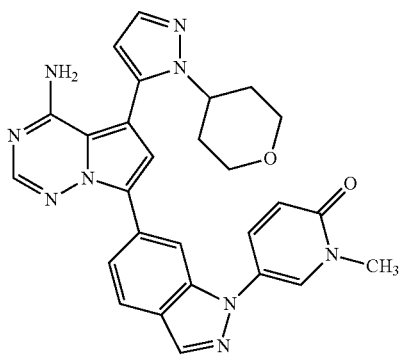

(19)

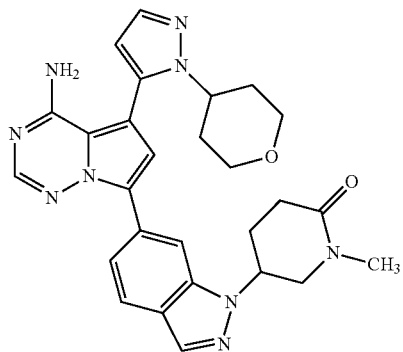

Example 18

7-(1H-Indazol-6-yl)-5-(1-(tetrahydro-2H-pyran-4-yl)-1H-pyrazol-5-yl)pyrrolo[2,1-f][1,2,4]triazin-4-amine (15 mg, 0.037 mmol), 1-methyl-5-(4,4,5,5-tetramethyl-1,3,2-dioxaborolan-2-yl)pyridin-2(1H)-one (17.61 mg, 0.075 mmol), copper (II) acetate (10.21 mg, 0.056 mmol), pyridine (6.06 μl, 0.075 mmol), 400 mg of 3 angstrom sieves (4A) and DCM (5 mL) were combined and stirred lightly for one week. The reaction complex was filtered with CELITE®, washed with water and the filtrate was extracted with ethyl acetate (5 mL×3). The organic layers were combined, dried, and concentrated. The crude residue was purified by preparative LC/MS Method B to obtain 5-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)-1-methylpyridin-2(1H)-one (4.7 mg, 9.26 μmol, 24.72% yield). LC/MS (M+H)$^+$=508.30. $^1$H NMR (500 MHz, DMSO-d$_6$) δ 1.82 (bs, 2H), 2.10 (m, 2H), 3.32 (t, 2H), 3.46 (m, 2H), 3.91 (s, 3H), 4.39 (m, 1H), 6.47 (s, 1H), 6.62 (d, 1H), 7.40 (s, 1H), 7.69 (s, 1H), 7.83 (d, 1H), 7.96 (m, 3H), 8.11 (s, 1H), 8.31 (s, 1H). 8.38 (s, 1H), 8.43 (s, 1H).

Example 19

5-(6-(4-Amino-5-(1-(tetrahydro-2H-pyran-4-yl)-1H-pyrazol-5-yl)pyrrolo[2,1-f][1,2,4]triazin-7-yl)-1H-indazol-1-yl)-1-methylpyridin-2(1H)-one (10 mg, 0.020 mmol) was dissolved in MeOH (10 mL) prior to the addition of Pd/C (2.097 mg, 0.020 mmol). The mixture was placed on the Parr instrument overnight at 43 psi of hydrogen pressure. The Pd was then filtered off and the filtrate was concentrated to afford 5-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)-1-methylpiperidin-2-one (6 mg, 10.79 μmol, 54.8% yield). $^1$H NMR (500 MHz, CDCl$_3$) δ 1.28 (m, 2H), 2.20 (m, 4H), 3.42 (m, 2H), 3.71 (m, 2H), 3.73 (s, 3H), 4.39 (m, 2H), 4.10 (m, 2H), 4.33 (m, 1H), 5.07 (m, 1H), 6.48 (d, 1H), 7.34 (s, 1H), 7.70 (s, 1H), 7.89 (q, 2H), 8.11 (s, 1H), 8.17 (s, 1H), 8.45 (s, 1H).

Following Examples in Table 9 were synthesized according to the general synthesis procedure for Examples 16-19 using appropriate commercial materials and Intermediates R14 to R27.

TABLE 9

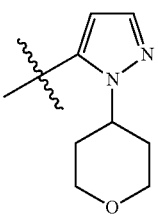

| Ex. No. | Q₁ | Q₂ | Name | [M + H]⁺ | HPLC $R_t$ (min) [Method] |
|---|---|---|---|---|---|
| 20 | 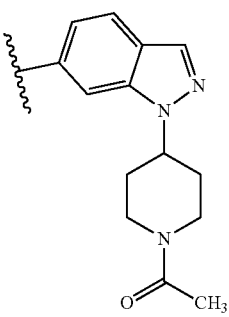 [SMILES: *c1ccc2cnn(C3CCN(C(C)=O)CC3)c2c1] | 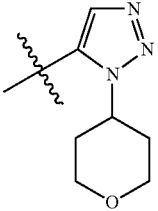 | 1-(4-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)piperidin-1-yl)ethanone | 526.40 | 1.12 [I] |
| 21 | 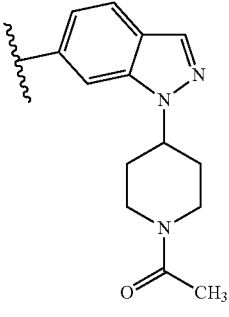 [SMILES: *c1ccc2cnn(C3CCN(C(C)=O)CC3)c2c1] | 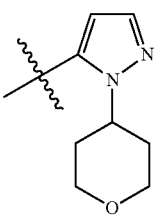 | 1-(4-(6-(4-amino-5-(1-(tetrahydro-2H-pyran-4-yl)-1H-1,2,3-triazol-5-yl)pyrrolo[2,1-f][1,2,4]triazin-7-yl)-1H-indazol-1-yl)piperidin-1-yl)ethanone | 527.30 | 1.07 [I] |
| 22 | 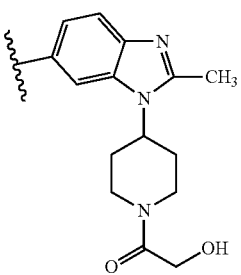 [SMILES: *c1ccc2nc(C)n(C3CCN(C(=O)CO)CC3)c2c1] | 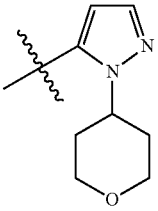 [SMILES: *c1ccnn1C1CCOCC1] | 1-(4-(6-(4-amino-5-(1-(tetrahydro-2H-pyran-4-yl)-1H-pyrazol-5-yl)pyrrolo[2,1-f][1,2,4]triazin-7-yl)-2-methyl-1H-benzo[d]imidazol-1-yl)piperidin-1-yl)-2-hydroxyethanone | 556.30 | 0.69 [I] |
| 23 | 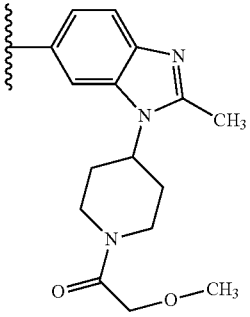 [SMILES: *c1ccc2nc(C)n(C3CCN(C(=O)COC)CC3)c2c1] | | 1-(4-(6-(4-amino-5-(1-(tetrahydro-2H-pyran-4-yl)-1H-pyrazol-5-yl)pyrrolo[2,1-f][1,2,4]triazin-7-yl)-2-methyl-1H-benzo[d]imidazol-1-yl)piperidin-1-yl)-2-methoxyethanone | 570.30 | 0.75 [I] |

TABLE 9-continued

| Ex. No. | Q₁ | Q₂ | Name | [M + H]⁺ | HPLC R_t (min) [Method] |
|---|---|---|---|---|---|
| 24 | 1-(tetrahydro-2H-pyran-4-yl)-1H-1,2,3-triazol-5-yl | 1-(tetrahydro-2H-pyran-4-yl)-1H-indazol-6-yl | 5-(1-(tetrahydro-2H-pyran-4-yl)-1H-1,2,3-triazol-5-yl)-7-(1-(tetrahydro-2H-pyran-4-yl)-1H-indazol-6-yl)pyrrolo[2,1-f][1,2,4]triazin-4-amine | 486.20 | 1.28 [I] |
| 25 | 1-isopropyl-1H-1,2,3-triazol-5-yl | 1-(tetrahydro-2H-pyran-4-yl)-1H-indazol-6-yl | 5-(1-isopropyl-1H-1,2,3-triazol-5-yl)-7-(1-(tetrahydro-2H-pyran-4-yl)-1H-indazol-6-yl)pyrrolo[2,1-f][1,2,4]triazin-4-amine | 444.10 | 1.29 [I] |
| 26 | 1-cyclohexyl-1H-1,2,3-triazol-5-yl | 1-(tetrahydro-2H-pyran-4-yl)-1H-indazol-6-yl | 5-(1-cyclohexyl-1H-1,2,3-triazol-5-yl)-7-(1-(tetrahydro-2H-pyran-4-yl)-1H-indazol-6-yl)pyrrolo[2,1-f][1,2,4]triazin-4-amine | 484.40 | 1.53 [I] |
| 27 | 1-(tetrahydro-2H-pyran-4-yl)-1H-pyrazol-5-yl | 1-(2,6-dimethyltetrahydro-2H-pyran-4-yl)-1H-indazol-6-yl | 7-(1-(2,6-dimethyltetrahydro-2H-pyran-4-yl)-1H-indazol-6-yl)-5-(1-(tetrahydro-2H-pyran-4-yl)-1H-pyrazol-5-yl)pyrrolo[2,1-f][1,2,4]triazin-4-amine | 513.30 | 1.44 [I] |
| 28 | 1-(tetrahydro-2H-pyran-4-yl)-1H-pyrazol-5-yl | 3-methyl-1-(tetrahydro-2H-pyran-4-yl)-1H-indazol-6-yl | 7-(3-methyl-1-(tetrahydro-2H-pyran-4-yl)-1H-indazol-6-yl)-5-(1-(tetrahydro-2H-pyran-4-yl)-1H-pyrazol-5-yl)pyrrolo[2,1-f][1,2,4]triazin-4-amine | 499.20 | 1.31 [I] |

TABLE 9-continued

| Ex. No. | Q₁ | Q₂ | Name | [M + H]⁺ | HPLC R$_t$ (min) [Method] |
|---|---|---|---|---|---|
| 29 | 1-(tetrahydro-2H-pyran-4-yl)-1H-1,2,3-triazol-5-yl | 3-methyl-1-(tetrahydro-2H-pyran-4-yl)-1H-indazol-6-yl | 7-(3-methyl-1-(tetrahydro-2H-pyran-4-yl)-1H-indazol-6-yl)-5-(1-(tetrahydro-2H-pyran-4-yl)-1H-1,2,3-triazol-5-yl)pyrrolo[2,1-f][1,2,4]triazin-4-amine | 500.20 | 1.25 [I] |
| 30 | 1-(tetrahydro-2H-pyran-4-yl)-1H-pyrazol-5-yl | 1-(tetrahydro-2H-pyran-4-yl)-1H-benzo[d]imidazol-6-yl | 7-(1-(tetrahydro-2H-pyran-4-yl)-1H-benzo[d]imidazol-6-yl)-5-(1-(tetrahydro-2H-pyran-4-yl)-1H-pyrazol-5-yl)pyrrolo[2,1-f][1,2,4]triazin-4-amine | 485.20 | 0.92 [I] |
| 31 | 1-(tetrahydro-2H-pyran-4-yl)-1H-1,2,3-triazol-5-yl | 1-(tetrahydro-2H-pyran-4-yl)-1H-benzo[d]imidazol-6-yl | 5-(1-(tetrahydro-2H-pyran-4-yl)-1H-1,2,3-triazol-5-yl)-7-(1-(tetrahydro-2H-pyran-4-yl)-1H-benzo[d]imidazol-6-yl)pyrrolo[2,1-f][1,2,4]triazin-4-amine | 486.20 | 0.69 [I] |
| 32 | 1-cyclohexyl-1H-1,2,3-triazol-5-yl | 1-(tetrahydro-2H-pyran-4-yl)-1H-benzo[d]imidazol-6-yl | 5-(1-cyclohexyl-1H-1,2,3-triazol-5-yl)-7-(1-(tetrahydro-2H-pyran-4-yl)-1H-benzo[d]imidazol-6-yl)pyrrolo[2,1-f][1,2,4]triazin-4-amine | 484.40 | 1.04 [I] |
| 33 | 1-(tetrahydro-2H-pyran-4-yl)-1H-pyrazol-5-yl | 1-(1,1-dioxidotetrahydro-2H-thiopyran-4-yl)-1H-indazol-6-yl | 4-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)tetrahydro-2H-thiopyran 1,1-dioxide | 533.20 | 1.18 [I] |

TABLE 9-continued

| Ex. No. | Q₁ | Q₂ | Name | [M + H]⁺ | HPLC R_t (min) [Method] |
|---|---|---|---|---|---|
| 34 | | | 4-(6-(4-amino-5-(1-(2,2,2-trifluoroethyl)-1H-pyrazol-5-yl)pyrrolo[2,1-f][1,2,4]triazin-7-yl)-1H-indazol-1-yl)tetrahydro-2H-thiopyran 1,1-dioxide | 531.20 | 1.29 [I] |
| 35 | | | 4-(6-(4-amino-5-(1-cyclohexyl-1H-1,2,3-triazol-5-yl)pyrrolo[2,1-f][1,2,4]triazin-7-yl)-1H-indazol-1-yl)tetrahydro-2H-thiopyran 1,1-dioxide | 532.22 | 1.44 [I] |
| 36 | | | 4-(6-(4-amino-5-(1-(tetrahydro-2H-pyran-4-yl)-1H-1,2,3-triazol-5-yl)pyrrolo[2,1-f][1,2,4]triazin-7-yl)-4-fluoro-1H-indazol-1-yl)tetrahydro-2H-thiopyran 1,1-dioxide | 552.3 | 1.3 [I] |
| 37 | | | 4-(6-(4-amino-5-(1-(tetrahydro-2H-pyran-4-yl)-1H-pyrazol-5-yl)pyrrolo[2,1-f][1,2,4]triazin-7-yl)-4-fluoro-1H-indazol-1-yl)tetrahydro-2H-thiopyran 1,1-dioxide | 551.3 | 1.37 [I] |

TABLE 9-continued

| Ex. No. | Q₁ | Q₂ | Name | [M+H]⁺ | HPLC $R_t$ (min) [Method] |
|---|---|---|---|---|---|
| 38 | 1-cyclopropyl-1H-pyrazol-5-yl | 4-fluoro-1-(1,1-dioxidotetrahydro-2H-thiopyran-4-yl)-1H-indazol-6-yl | 4-(6-(4-amino-5-(1-cyclopropyl-1H-pyrazol-5-yl)pyrrolo[2,1-f][1,2,4]triazin-7-yl)-4-fluoro-1H-indazol-1-yl)tetrahydro-2H-thiopyran 1,1-dioxide | 507.3 | 1.39 [I] |
| 39 | 1-(tetrahydro-2H-pyran-4-yl)-1H-pyrazol-5-yl | 1-(1,1-dioxidotetrahydro-2H-thiopyran-4-yl)-1H-benzo[d]imidazol-6-yl | 4-(6-(4-amino-5-(1-(tetrahydro-2H-pyran-4-yl)-1H-pyrazol-5-yl)pyrrolo[2,1-f][1,2,4]triazin-7-yl)-1H-benzo[d]imidazol-1-yl)tetrahydro-2H-thiopyran 1,1-dioxide | 533.30 | 0.75 [I] |
| 40 | 1-(tetrahydro-2H-pyran-4-yl)-1H-1,2,3-triazol-5-yl | 1-(1,1-dioxidotetrahydro-2H-thiopyran-4-yl)-1H-benzo[d]imidazol-6-yl | 4-(6-(4-amino-5-(1-(tetrahydro-2H-pyran-4-yl)-1H-1,2,3-triazol-5-yl)pyrrolo[2,1-f][1,2,4]triazin-7-yl)-1H-benzo[d]imidazol-1-yl)tetrahydro-2H-thiopyran 1,1-dioxide | 534.30 | 0.67 [I] |
| 41 | 1-(2,2,2-trifluoroethyl)-1H-pyrazol-5-yl | 1-(1,1-dioxidotetrahydro-2H-thiopyran-4-yl)-1H-benzo[d]imidazol-6-yl | 4-(6-(4-amino-5-(1-(2,2,2-trifluoroethyl)-1H-pyrazol-5-yl)pyrrolo[2,1-f][1,2,4]triazin-7-yl)-1H-benzo[d]imidazol-1-yl)tetrahydro-2H-thiopyran 1,1-dioxide | 531.20 | 0.83 [I] |

TABLE 9-continued

| Ex. No. | Q₁ | Q₂ | Name | [M + H]⁺ | HPLC R$_t$ (min) [Method] |
|---|---|---|---|---|---|
| 42 | 1-(tetrahydro-2H-pyran-4-yl)-1H-pyrazol-5-yl | 1-isopropyl-1H-indazol-6-yl | 7-(1-isopropyl-1H-indazol-6-yl)-5-(1-(tetrahydro-2H-pyran-4-yl)-1H-pyrazol-5-yl)pyrrolo[2,1-f][1,2,4]triazin-4-amine | 443.10 | 1.41 [I] |
| 43 | 1-(tetrahydro-2H-pyran-4-yl)-1H-1,2,3-triazol-5-yl | 1-(cyclopropylmethyl)-1H-indazol-6-yl | 7-(1-(cyclopropylmethyl)-1H-indazol-6-yl)-5-(1-(tetrahydro-2H-pyran-4-yl)-1H,1,2,3-triazol-5-yl)pyrrolo[2,1-f][1,2,4]triazin-4-amine | 456.10 | 1.32 [I] |
| 44 | 1-(tetrahydro-2H-pyran-4-yl)-1H-pyrazol-5-yl | 1-(cyclopropylmethyl)-1H-indazol-6-yl | 7-(1-(cyclopropylmethyl)-1H-indazol-6-yl)-5-(1-(tetrahydro-2H-pyran-4-yl)-1H-pyrazol-5-yl)pyrrolo[2,1-f][1,2,4]triazin-4-amine | 455.20 | 1.38 [I] |
| 45 | 1-(tetrahydro-2H-pyran-4-yl)-1H-1,2,3-triazol-5-yl | 1-(cyclopropylmethyl)-1H-benzo[d]imidazol-6-yl | 7-(1-(cyclopropylmethyl)-1H-benzo[d]imidazol-6-yl)-5-(1-(tetrahydro-2H-pyran-4-yl)-1H-1,2,3-triazol-5-yl)pyrrolo[2,1-f][1,2,4]triazin-4-amine | 456.20 | 0.79 [I] |
| 46 | 1-(tetrahydro-2H-pyran-4-yl)-1H-pyrazol-5-yl | 1-(cyclopropylmethyl)-1H-benzo[d]imidazol-6-yl | 7-(1-(cyclopropylmethyl)-1H-benzo[d]imidazol-6-yl)-5-(1-(tetrahydro-2H-pyran-4-yl)-1H-pyrazol-5-yl)pyrrolo[2,1-f][1,2,4]triazin-4-amine | 455.10 | 0.87 [I] |
| 47 | 1-(tetrahydro-2H-pyran-4-yl)-1H-1,2,3-triazol-5-yl | 1-((2,2-difluorocyclopropyl)methyl)-1H-indazol-6-yl | 7-(1-((2,2-difluorocyclopropyl)methyl)-1H-indazol-6-yl)-5-(1-(tetrahydro-2H-pyran-4-yl)-1H-1,2,3-triazol-5-yl)pyrrolo[2,1-f][1,2,4]triazin-4-amine | 492.30 | 1.26 [I] |

TABLE 9-continued

| Ex. No. | Q₁ | Q₂ | Name | [M + H]⁺ | HPLC R$_t$ (min) [Method] |
|---|---|---|---|---|---|
| 48 | pyrazol-1-yl with tetrahydropyran-4-yl | indazol-6-yl with ((2,2-difluorocyclopropyl)methyl) | 7-(1-((2,2-difluorocyclopropyl)methyl)-1H-indazol-6-yl)-5-(1-(tetrahydro-2H-pyran-4-yl)-1H-pyrazol-5-yl)pyrrolo[2,1-f][1,2,4]triazin-4-amine | 491.10 | 1.39 [I] |
| 49 | pyrazol-1-yl with tetrahydropyran-4-yl | indazol-6-yl with 2-hydroxy-3-fluoropropyl | 1-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)-3-fluoropropan-2-ol | 477.20 | 1.07 [I] |
| 50 | 1,2,3-triazol-5-yl with tetrahydropyran-4-yl | indazol-6-yl with 2-hydroxy-3-fluoropropyl | 1-(6-(4-amino-5-(1-(tetrahydro-2H-pyran-4-yl)-1H-1,2,3-triazol-5-yl)pyrrolo[2,1-f][1,2,4]triazin-7-yl)-1H-indazol-1-yl)-3-fluoropropan-2-ol | 478.20 | 0.99 [I] |
| 51 | pyrazol-1-yl with tetrahydropyran-4-yl | indazol-6-yl with N,N-dimethylacetamide | 2-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)-N,N-dimethylacetamide | 486.20 | 1.02 [I] |
| 52 | pyrazol-1-yl with tetrahydropyran-4-yl | indazol-6-yl with pyrrolidin-2-one-5-ylmethyl | (R)-5-((6-(4-amino-5-(1-(tetrahydro-2H-pyran-4-yl)-1H-pyrazol-5-yl)pyrrolo[2,1-f][1,2,4]triazin-7-yl)-1H-indazol-1-yl)methyl)pyrrolidin-2-one | 498.30 | 0.99 [I] |
| 54 | pyrazol-1-yl with tetrahydropyran-4-yl | indazol-6-yl with ((5-methylisoxazol-3-yl)methyl) | 7-(1-((5-methylisoxazol-3-yl)methyl)-1H-indazol-6-yl)-5-(1-(tetrahydro-2H-pyran-4-yl)-1H-pyrazol-5-yl)pyrrolo[2,1-f][1,2,4]triazin-4-amine | 496.20 | 1.29 [I] |

TABLE 9-continued

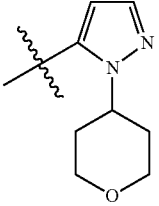 [SMILES: *c1ccnn1C1CCOCC1]

| Ex. No. | Q₁ | Q₂ | Name | [M + H]⁺ | HPLC R$_t$ (min) [Method] |
|---|---|---|---|---|---|
| 55 | 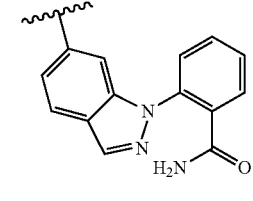 [SMILES: *c1ccc2cnn(-c3ccccc3C(N)=O)c2c1] | 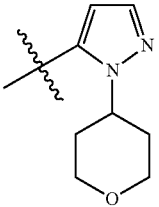 | 2-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)benzamide | 520.30 | 1.10 [I] |
| 56 | 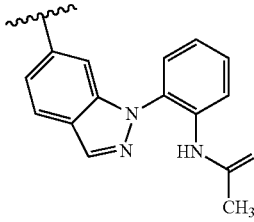 | 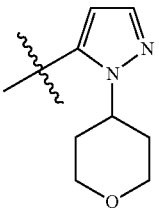 [SMILES: *c1ccnn1C1CCOCC1] | N-(2-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)phenyl)acetamide | 534.30 | 1.34 [I] |
| 57 | 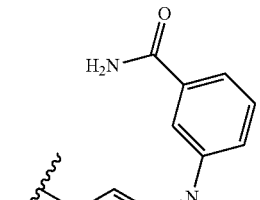 | 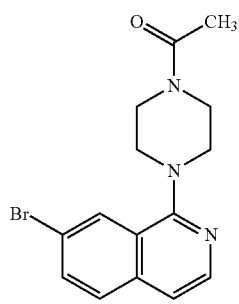 | 3-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)benzamide | 520.40 | 1.21 [I] |

Example 58

1-(4-(7-(4-Amino-5-(1-(tetrahydro-2H-pyran-4-yl)-1H-1,2,3-triazol-5-yl)pyrrolo[2,1-f][1,2,4]triazin-7-yl)isoquinolin-1-yl)piperazin-1-yl)ethanone (58)

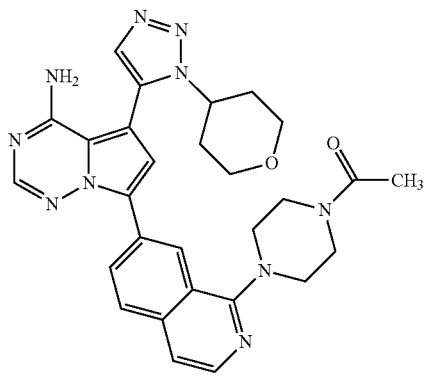

Intermediate 58A: 1-(4-(7-Bromoisoquinolin-1-yl)piperazin-1-yl)ethanone (58A)

To a solution of 7-bromo-1-chloroisoquinoline (0.3 g, 1.237 mmol) in ethylene glycol (5 mL), 1-(piperazin-1-yl)ethanone (0.238 g, 1.856 mmol), DIPEA (0.648 mL, 3.71 mmol) were added. The mixture was heated and stirred at 145° C. for 1 h in a microwave. The mixture was cooled to room temperature, diluted with EtOAc (20 mL), and washed with H₂O (5 mL). The orange organic layer was washed with brine, dried over MgSO₄, and concentrated to give a crude product which was purified by flash chromatography on silica gel eluting with 0-100% EtOAc/hexane (12 g column, 16 min grad) to obtain 1-(4-(7-bromoisoquinolin-1-yl)piperazin-1-yl)ethanone (0.283 g, 0.847 mmol, 68.4% yield). LCMS (M+H)⁺=334.10, 336.10 (1:1 ratio).

Example 58

To a solution of 1-(4-(7-bromoisoquinolin-1-yl)piperazin-1-yl)ethanone (44.2 mg, 0.132 mmol) in dioxane (2 mL) were added 4,4,4',4',5,5,5',5'-octamethyl-2,2'-bi(1,3,2-dioxaborolane) (33.6 mg, 0.132 mmol), potassium acetate (43.2 mg, 0.441 mmol), and PPdCl₂(dppf)-CH₂Cl₂ adduct (18 mg, 0.022 mmol). The microwave reaction vessel was degassed with N2 as described previously. The sealed reaction vessel was heated at 120° C. in a microwave for 20 min. To the cooled reaction mixture were added, water (0.5 mL), 7-bromo-5-(1-(tetrahydro-2H-pyran-4-yl)-1H-1,2,3-triazol-5-yl)pyrrolo[2,1-f][1,2,4]triazin-4-amine (40.1 mg, 0.110 mmol), sodium carbonate (35 mg, 0.33 mmol) and additional PdCl₂(dppf)-CH₂Cl₂ adduct (18 mg). The sealed reaction vessel was degassed and heated at 120° C. in a microwave for 30 min. The reaction mixture was filtered, washed with water, and extracted with ethyl acetate (10 mL×3). The organic layers were mixed, dried, concentrated and purified by preparative LC Method B to afford 1-(4-(7-(4-amino-5-(1-(tetrahydro-2H-pyran-4-yl)-1H-1,2,3-triazol-5-yl)pyrrolo[2,1-f][1,2,4]triazin-7-yl)isoquinolin-1-yl)piperazin-1-yl)ethanone (13.2 mg, 22% yield). LCMS (M+H)⁺=539.20. ¹H NMR (500 MHz, DMSO-d₆) δ 2.04 (d, 2H), 2.11 (s, 3H), 2.18 (m, 4H), 3.40 (m, 2H), 3.17 (d, 2H), 3.94 (d, 4H), 4.15 (m, 1H), 4.63 (m, 2H), 7.43 (d, 1H), 7.51 (s, 1H), 7.90 (s, 2H), 7.98 (m, 1H), 8.15 (d, 1H), 8.22 (s, 1H), 8.28 (d, 1H), 9.27 (s, 1H).

The Examples in Table 10 were synthesized according to the general synthetic procedure described for the synthesis of Example 58, using appropriate commercial materials and intermediates.

TABLE 10

| Ex. No. | Q₁ | R₂ | Name | [M + H]⁺ | HPLC R_t (min) [Method] |
|---|---|---|---|---|---|
| 59 | 1-(tetrahydro-2H-pyran-4-yl)-1H-1,2,3-triazol-5-yl | morpholino | 7-(1-morpholinoisoquinolin-7-yl)-5-(1-(tetrahydro-2H-pyran-4-yl)-1H-1,2,3-triazol-5-yl)pyrrolo[2,1-f][1,2,4]triazin-4-amine | 497.80 | 1.39 [H] |
| 60 | 1-isopropyl-1H-1,2,3-triazol-5-yl | thiomorpholine 1,1-dioxide | 4-(7-(4-amino-5-(1-isopropyl-1H-1,2,3-triazol-5-yl)pyrrolo[2,1-f][1,2,4]triazin-7-yl)isoquinolin-1-yl)thiomorpholine 1,1-dioxide | 504.20 | 1.07 [H] |
| 61 | 1-(tetrahydro-2H-pyran-4-yl)-1H-1,2,3-triazol-5-yl | thiomorpholine 1,1-dioxide | 4-(7-(4-amino-5-(1-(tetrahydro-2H-pyran-4-yl)-1H-1,2,3-triazol-5-yl)pyrrolo[2,1-f][1,2,4]triazin-7-yl)isoquinolin-1-yl)thiomorpholine 1,1-dioxide | 546.05 | 1.119 [H] |

The Examples in Table 11 were prepared according to the procedures described for examples exemplified above, using appropriate intermediates and chemistry known to those skilled in the art.

TABLE 11

| Ex. No. | Q₁ | R₂ | Name | M⁺ | HPLC R$_t$ (min) [Method] |
|---|---|---|---|---|---|
| 62 | 5-(1-(tetrahydro-2H-pyran-4-yl)-1H-pyrazol-5-yl) | piperazin-1-yl | 7-(2-(piperazin-1-yl)pyridin-4-yl)-5-(1-(tetrahydro-2H-pyran-4-yl)-1H-pyrazol-5-yl)pyrrolo[2,1-f][1,2,4]triazin-4-amine | 446.10 | 0.16 F |
| 63 | 5-(1-(tetrahydro-2H-pyran-4-yl)-1H-pyrazol-5-yl) | 4-(oxetan-3-yl)piperazin-1-yl | 7-(2-(4-(oxetan-3-yl)piperazin-1-yl)pyridin-4-yl)-5-(1-(tetrahydro-2H-pyran-4-yl)-1H-pyrazol-5-yl)pyrrolo[2,1-f][1,2,4]triazin-4-amine | 502.3 | 0.65 F |
| 64 | 5-(1-(tetrahydro-2H-pyran-4-yl)-1H-1,2,3-triazol-5-yl) | 4-methylpiperazin-1-yl | 7-(2-(4-methylpiperazin-1-yl)pyridin-4-yl)-5-(1-(tetrahydro-2H-pyran-4-yl)-1H-pyrazol-5-yl)pyrrolo[2,1-f][1,2,4]triazin-4-amine | 460.3 | 0.62 F |
| 65 | 5-(1-(tetrahydro-2H-pyran-4-yl)-1H-pyrazol-5-yl) | 4-acetylpiperazin-1-yl | 1-(4-(4-(4-amino-5-(1-(tetrahydro-2H-pyran-4-yl)-1H-pyrazol-5-yl)pyrrolo[2,1-f][1,2,4]triazin-7-yl)pyridin-2-yl)piperazin-1-yl)ethanone | 488.3 | 0.79 F |

Example 66

2-(4-(4-Amino-5-(1-(tetrahydro-2H-pyran-4-yl)-1H-pyrazol-5-yl)pyrrolo[2,1-f][1,2,4]triazin-7-yl)pyridin-2-yl)benzamide

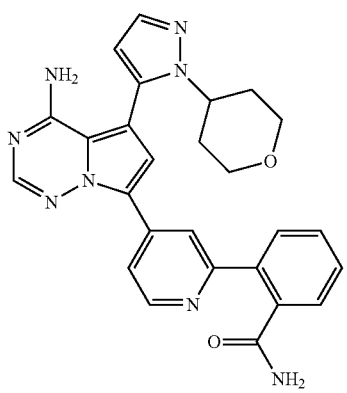

(66)

Intermediate 66A: 7-(2-Chloropyridin-4-yl)-5-(1-(tetrahydro-2H-pyran-4-yl)-1H-pyrazol-5-yl)pyrrolo[2,1-f][1,2,4]triazin-4-amine

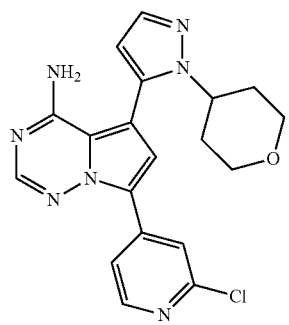

(66A)

To a solution of 7-bromo-5-(1-(tetrahydro-2H-pyran-4-yl)-1H-pyrazol-5-yl)pyrrolo[2,1-f][1,2,4]triazin-4-amine (100 mg, 0.275 mmol) in dioxane (3 mL), was added 2-chloro-4-(4,4,5,5-tetramethyl-1,3,2-dioxaborolan-2-yl)pyridine (79 mg, 0.330 mmol), an aqueous solution of potassium phosphate tribasic (2M, 0.42 mL, 0.83 mmol), and Pd(PPh$_3$)$_4$ (31.8 mg, 0.028 mmol). The reaction vial was purged with nitrogen for 5 minutes, sealed and heated at 100° C. for 3 h. The reaction mixture was filtered through a pad of CELITE® and extracted with EtOAc. The organic layer was washed with brine, water, dried over sodium sulfate, concentrated and purified by prep-HPLC to afford the product (80 mg, 66% yield) as off-white solid. MS (E+) m/z: 396.3 (M+H); LCMS retention time: 2.72 min.

Example 66

To a 1 dram vial flushed with nitrogen, was added Intermediate 66A (15 mg, 0.038 mmol), (2-carbamoylphenyl)boronic acid (9.38 mg, 0.057 mmol), an aqueous solution of potassium phosphate tribasic (2M in water, 0.038 mL, 0.076 mmol) and (2-carbamoylphenyl)boronic acid (9.38 mg, 0.057 mmol). The air above the solids was flushed with nitrogen. Then the vial was capped tightly with a pressure-safe septum cap and heated at 100° C. for 3 h. The reaction mixture was filtered through a pad of CELITE® and concentrated. The crude material was purified via preparative LC/MS with the following condition: Column: Water XBridge c18, 19×200 mm, 5-µm particles; Mobile Phase A: 5:95 acetonitrile/water with 10-mM ammonium acetate; Mobile Phase B: 95:5 acetonitrile/water with 10-mM ammonium acetate; Gradient: 0-100% B over 19 minutes, then a 5-minute hold at 100% B; Flow 20 mL/min. Fractions containing the desired product were combined and dried via centrifugal evaporation to afford Example 66 (8.8 mg, 48% yield). MS (E+) m/z: 481.2 (M+H); LCMS retention time: 1.05 min. $^1$H NMR (500 MHz, DMSO-d$_6$) δ 8.68 (d, J=5.4 Hz, 1H), 8.42 (s, 1H), 8.22-8.08 (m, 2H), 7.82 (br. s., 1H), 7.76-7.65 (m, 2H), 7.61-7.45 (m, 4H), 7.32 (br. s., 1H), 6.49 (d, J=1.3 Hz, 1H), 4.46-4.28 (m, 1H), 3.99-3.78 (m, 3H), 3.54-3.13 (m, 3H), 2.22-2.01 (m, J=95.3 Hz, 2H).

Example 67

2-(5-(4-Amino-5-(1-(tetrahydro-2H-pyran-4-yl)-1H-pyrazol-5-yl)pyrrolo[2,1-f][1,2,4]triazin-7-yl)pyridin-3-yl)benzamide

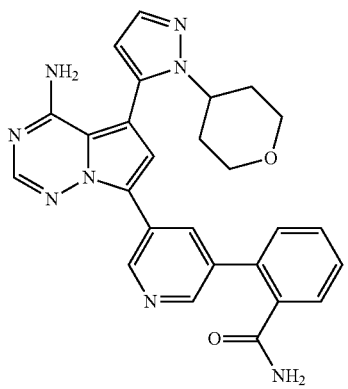

(67)

Example 67 was prepared according to the general synthesis procedure for Example 66. MS (E+) m/z: 481.2 (M+H); LCMS retention time: 1.07 min. $^1$H NMR (500 MHz, DMSO-d$_6$) δ 9.26 (s, 1H), 8.59 (d, J=16.5 Hz, 2H), 8.09 (s, 1H), 7.95 (s, 1H), 7.88 (br. s., 1H), 7.69 (s, 1H), 7.61-7.50 (m, 4H), 7.42 (br. s., 2H), 6.48 (s, 1H), 4.40 (t, J=11.4 Hz, 1H), 3.89 (d, J=13.8 Hz, 2H), 3.51-3.16 (m, 2H), 2.11 (d, J=8.1 Hz, 2H), 1.94-1.73 (m, 2H).

Example 68

7-(2-(2-(Methylsulfonyl)phenyl)pyridin-4-yl)-5-(1-(tetrahydro-2H-pyran-4-yl)-1H-pyrazol-5-yl)pyrrolo[2,1-f][1,2,4]triazin-4-amine

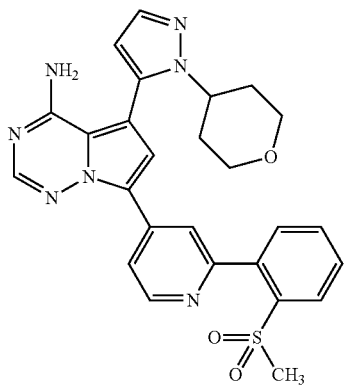

(68)

Example 68 was prepared according to the general synthesis procedure for Example 66. MS (E+) m/z: 516.5 (M+H); LCMS retention time: 1.05 min. $^1$H NMR (500 MHz, DMSO-d$_6$) δ 8.78 (d, J=5.4 Hz, 1H), 8.47 (s, 1H), 8.36 (d, J=5.0 Hz, 1H), 8.26-8.17 (m, 2H), 7.97-7.90 (m, 1H), 7.87-7.81 (m, 1H), 7.78-7.70 (m, 3H), 6.55 (s, 1H), 4.48-4.37 (m, 1H), 4.00-3.87 (m, 2H), 3.46-3.34 (m, 1H), 2.24-2.10 (m, 3H), 2.03-1.75 (m, 2H).

The Examples in Table 12 were prepared according to the procedures described for examples exemplified above, using appropriate intermediates and chemistry known to those skilled in the art.

TABLE 12

| Ex. No. | Structure | Name | M + H |
|---|---|---|---|
| 69 | 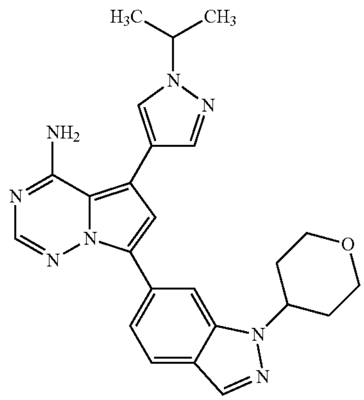 [SMILES: CC(C)n1cc(-c2cc(-c3ccc4cnn(C5CCOCC5)c4c3)n3ncnc(N)c23)cn1] | 7-[1-(oxan-4-yl)-1H-indazol-6-yl]-5-[1-(propan-2-yl)-1H-pyrazol-4-yl]pyrrolo[2,1-f][1,2,4]triazin-4-amine | 443 |
| 70 | 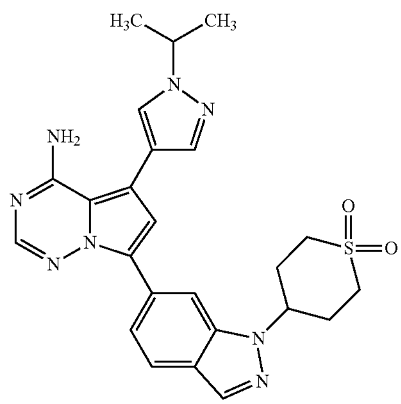 [SMILES: CC(C)n1cc(-c2cc(-c3ccc4cnn(C5CCS(=O)(=O)CC5)c4c3)n3ncnc(N)c23)cn1] | 4-(6-{4-amino-5-[1-(propan-2-yl)-1H-pyrazol-4-yl]pyrrolo[2,14][1,2,4]triazin-7-yl}-1H-indazol-1-yl)-1λ$^6$-thiane-1,1-dione | 491 |
| 71 | 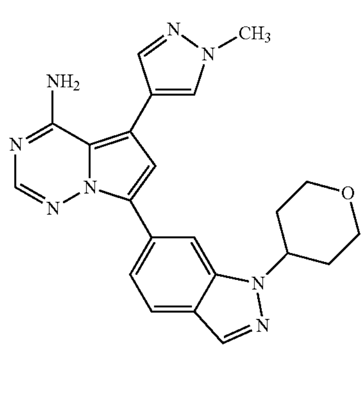 [SMILES: Cn1cc(-c2cc(-c3ccc4cnn(C5CCOCC5)c4c3)n3ncnc(N)c23)cn1] | 5-(1-methyl-1H-pyrazol-4-yl)-7-[1-(oxan-4-yl)-1H-indazol-6-yl]pyrrolo[2,1-f][1,2,4]triazin-4-amine | 415 |

TABLE 12-continued

| Ex. No. | Structure | Name | M + H |
|---|---|---|---|
| 72 | 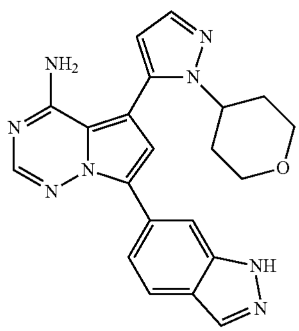 [SMILES: Nc1ncnn2c(-c3ccc4cn[nH]c4c3)cc(-c3ccnn3C3CCOCC3)c12] | 7-(1H-indazol-6-yl)-5-[1-(oxan-4-yl)-1H-pyrazol-5-yl]pyrrolo[2,1-f][1,2,4]triazin-4-amine | 401 |
| 73 | 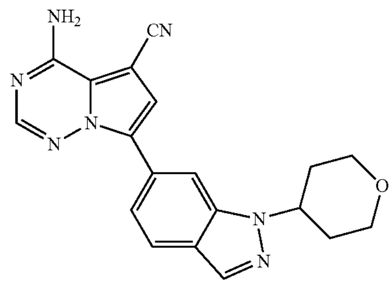 [SMILES: N#Cc1cc(-c2ccc3cnn(C4CCOCC4)c3c2)n2ncnc(N)c12] | 4-amino-7-[1-(oxan-4-yl)-1H-indazol-6-yl]pyrrolo[2,14][1,2,4]triazine-5-carbonitrile | 360 |
| 74 | 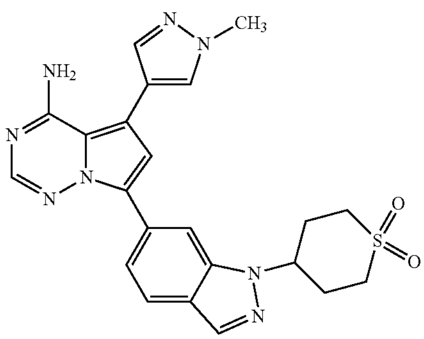 [SMILES: Cn1cc(-c2cc(-c3ccc4cnn(C5CCS(=O)(=O)CC5)c4c3)n3ncnc(N)c23)cn1] | 4-{6-[4-amino-5-(1-methyl-1H-pyrazol-4-yl)pyrrolo[2,1-f][1,2,4]triazin-7-yl]-1H-indazol-1-yl}-1$\lambda^6$-thiane-1,1-dione | 463 |
| 75 | 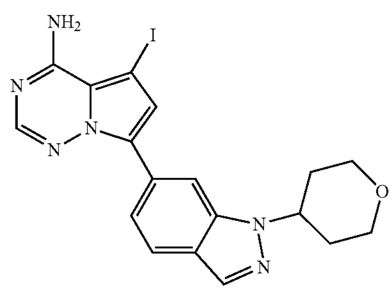 [SMILES: Nc1ncnn2c(-c3ccc4cnn(C5CCOCC5)c4c3)cc(I)c12] | 5-iodo-7-[1-(oxan-4-yl)-1H-indazol-6-yl]pyrrolo[2,1-f][1,2,4]triazin-4-amine | 461 |
| 76 | 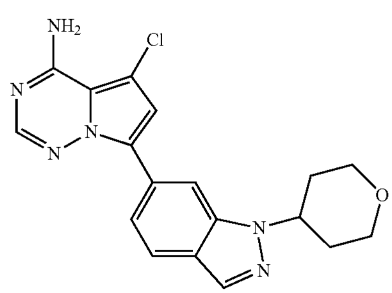 [SMILES: Nc1ncnn2c(-c3ccc4cnn(C5CCOCC5)c4c3)cc(Cl)c12] | 5-chloro-7-[1-(oxan-4-yl)-1H-indazol-6-yl]pyrrolo[2,1-f][1,2,4]triazin-4-amine | 369 |

TABLE 12-continued

| Ex. No. | Structure | Name | M + H |
|---|---|---|---|
| 77 | 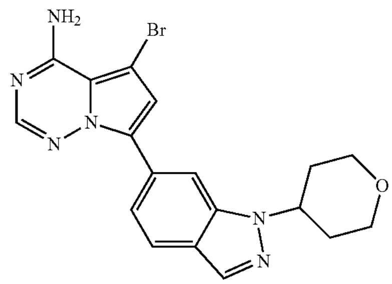 [SMILES: Nc1ncnn2c(-c3ccc4cnn(C5CCOCC5)c4c3)cc(Br)c12] | 5-bromo-7-[1-(oxan-4-yl)-1H-indazol-6-yl]pyrrolo[2,1-f][1,2,4]triazin-4-amine | 414 |
| 78 | 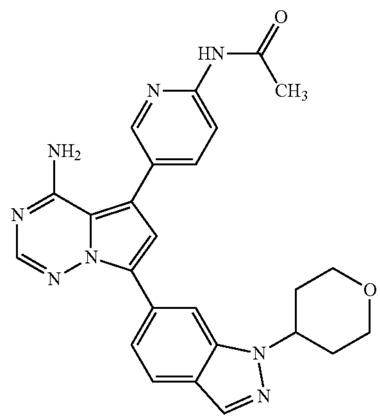 [SMILES: CC(=O)Nc1ccc(-c2cc(-c3ccc4cnn(C5CCOCC5)c4c3)n3ncnc(N)c23)cn1] | N-(5-{4-amino-7-[1-(oxan-4-yl)-1H-indazol-6-yl]pyrrolo[2,1-f][1,2,4]triazin-5-yl}pyridin-2-yl)acetamide | 469 |
| 79 | 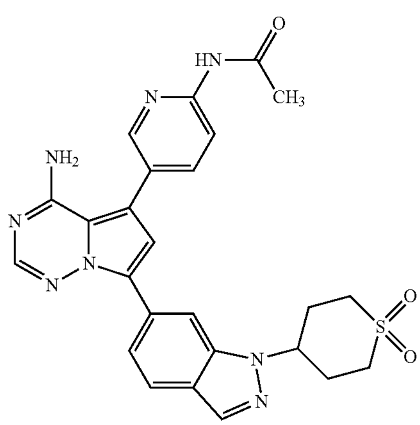 [SMILES: CC(=O)Nc1ccc(-c2cc(-c3ccc4cnn(C5CCS(=O)(=O)CC5)c4c3)n3ncnc(N)c23)cn1] | N-(5-{4-amino-7-[1-(1,1-dioxo-1$\lambda^6$-thian-4-yl)-1H-indazol-6-yl]pyrrolo[2,1-f][1,2,4]triazin-5-yl}pyridin-2-yl)acetamide | 517 |
| 80 | 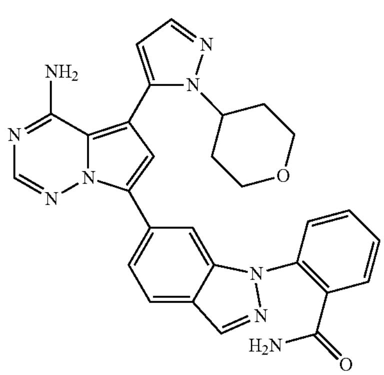 [SMILES: NC(=O)c1ccccc1-n1ncc2ccc(-c3cc(-c4ccnn4C4CCOCC4)c4c(N)ncnn34)cc21] | 2-(6-(4-amino-5-(1-(tetrahydro-2H-pyran-4-yl)-1H-pyrazol-5-yl)pyrrolo[2,1-f][1,2,4]triazin-7-yl)-1H-benzo[d]imidazol-1-yl)benzamide | 520 |

TABLE 12-continued

| Ex. No. | Structure | Name | M + H |
|---|---|---|---|
| 81 | 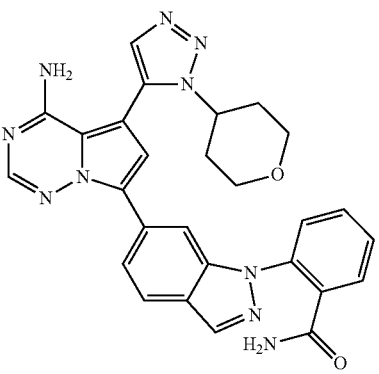 [SMILES: NC(=O)c1ccccc1-n1ncc2ccc(-c3cc(-c4cnnn4C4CCOCC4)c4c(N)ncnn34)cc21] | 2-(6-(4-amino-5-(1-(tetrahydro-2H-pyran-4-yl)-1H-1,2,3-triazol-5-yl)pyrrolo[2,1-f][1,2,4]triazin-7-yl)-1H-benzo[d]imidazol-1-yl)benzamide | 521 |
| 82 | 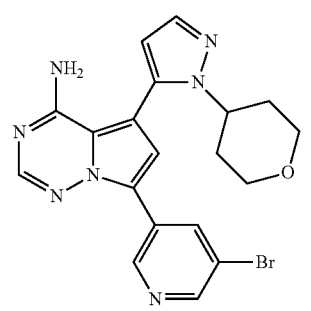 [SMILES: Nc1ncnn2c(-c3cncc(Br)c3)cc(-c3ccnn3C3CCOCC3)c12] | 7-(5-bromopyridin-3-yl)-5-[1-(oxan-4-yl)-1H-pyrazol-5-yl]pyrrolo[2,1-f][1,2,4]triazin-4-amine | 441 |

The Examples in Table 13 were prepared according to the general synthesis procedures in the previous Examples and methods known in the art with appropriate starting materials.

TABLE 13

| Ex. No. | Structure | Name | M + H |
|---|---|---|---|
| 83 | 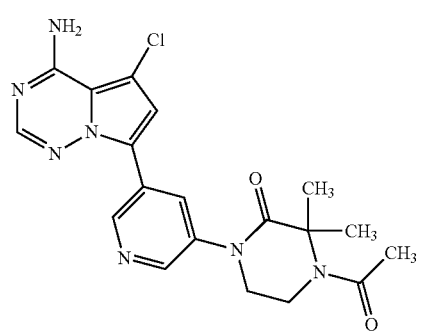 [SMILES: CC(=O)N1CCN(c2cncc(-c3cc(Cl)c4c(N)ncnn34)c2)C(=O)C1(C)C] | 4-acetyl-1-(5-(4-amino-5-chloropyrrolo[2,1-f][1,2,4]triazin-7-yl)pyridin-3-yl)-3,3-dimethylpiperazin-2-one | 415 |

TABLE 13-continued

| Ex. No. | Structure | Name | M + H |
|---|---|---|---|
| 84 | 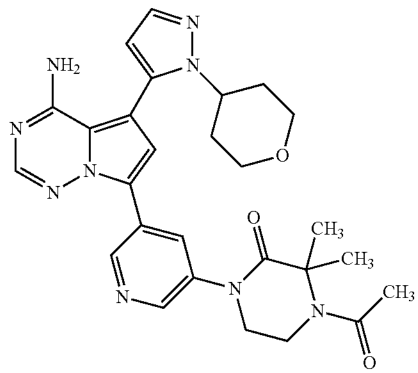 [SMILES: CC(=O)N1CCN(c2cncc(-c3cc(-c4ccnn4C4CCOCC4)c4c(N)ncnn34)c2)C(=O)C1(C)C] | 4-acetyl-1-(5-(4-amino-5-(1-(tetrahydro-2H-pyran-4-yl)-1H-pyrazol-5-yl)pyrrolo[2,1-f][1,2,4]triazin-7-yl)pyridin-3-yl)-3,3-dimethylpiperazin-2-one | 531 |
| 85 | 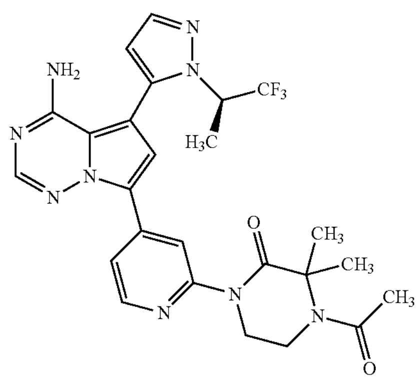 [SMILES: CC(=O)N1CCN(c2cc(-c3cc(-c4ccnn4[C@H](C)C(F)(F)F)c4c(N)ncnn34)ccn2)C(=O)C1(C)C] | (R)-4-acetyl-1-(4-(4-amino-5-(1-(1,1,1-trifluoropropan-2-yl)-1H-pyrazol-5-yl)pyrrolo[2,1-f][1,2,4]triazin-7-yl)pyridin-2-yl)-3,3-dimethylpiperazin-2-one | 543 |
| 86 | 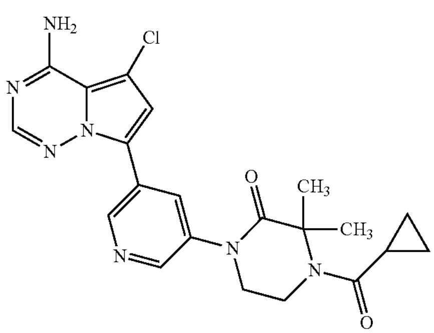 [SMILES: CC1(C)C(=O)N(c2cncc(-c3cc(Cl)c4c(N)ncnn34)c2)CCN1C(=O)C1CC1] | 1-(5-(4-amino-5-chloropyrrolo[2,1-f][1,2,4]triazin-7-yl)pyridin-3-yl)-4-(cyclopropanecarbonyl)-3,3-dimethylpiperazin-2-one | 441 |
| 87 | 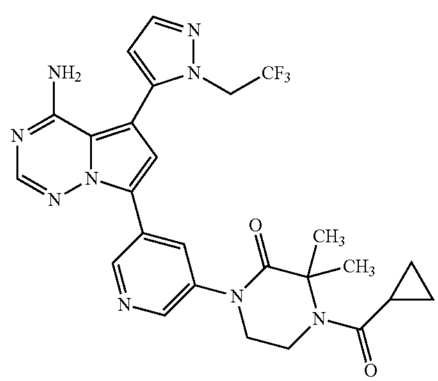 [SMILES: CC1(C)C(=O)N(c2cncc(-c3cc(-c4ccnn4CC(F)(F)F)c4c(N)ncnn34)c2)CCN1C(=O)C1CC1] | 1-(5-(4-amino-5-(1-(2,2,2-trifluoroethyl)-1H-pyrazol-5-yl)pyrrolo[2,1-f][1,2,4]triazin-7-yl)pyridin-3-yl)-4-(cyclopropanecarbonyl)-3,3-dimethylpiperazin-2-one | 555 |

TABLE 13-continued

| Ex. No. | Structure | Name | M + H |
|---|---|---|---|
| 88 | 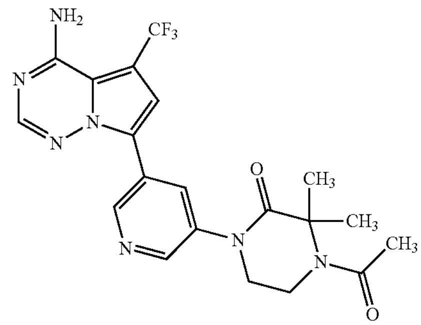 | 4-acetyl-1-(5-(4-amino-5-(trifluoromethyl)pyrrolo[2,1-f][1,2,4]triazin-7-yl)pyridin-3-yl)-3,3-dimethylpiperazin-2-one | 448 |
| 89 | 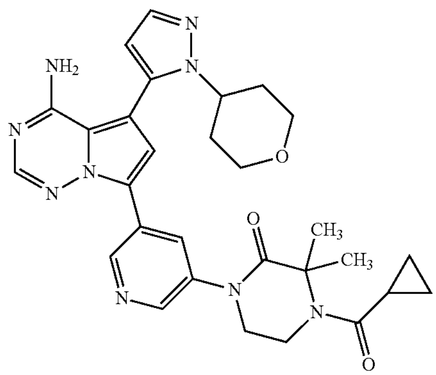 [SMILES: CC1(C)C(=O)N(c2cncc(-c3cc(-c4ccnn4C4CCOCC4)c4c(N)ncnn34)c2)CCN1C(=O)C1CC1] | 1-(5-(4-amino-5-(1-(tetrahydro-2H-pyran-4-yl)-1H-pyrazol-5-yl)pyrrolo[2,1-f][1,2,4]triazin-7-yl)pyridin-3-yl)-4-(cyclopropanecarbonyl)-3,3-dimethylpiperazin-2-one | 557 |
| 90 | 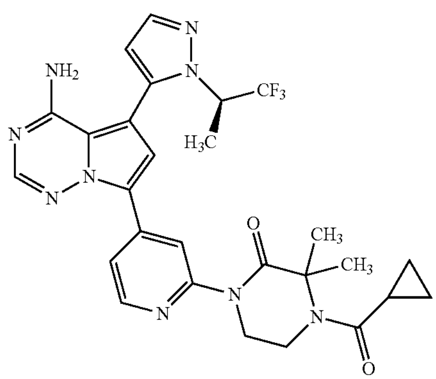 [SMILES: C[C@@H](n1nccc1-c1cc(-c2ccnc(N3CCN(C(=O)C4CC4)C(C)(C)C3=O)c2)n2ncnc(N)c12)C(F)(F)F] | (R)-1-(4-(4-amino-5-(1-(1,1,1-trifluoropropan-2-yl)-1H-pyrazol-5-yl)pyrrolo[2,1-f][1,2,4]triazin-7-yl)pyridin-2-yl)-4-(cyclopropanecarbonyl)-3,3-dimethylpiperazin-2-one | 569 |

TABLE 14

| Ex. No. | Structure | Name | M + H |
|---|---|---|---|
| 91 | 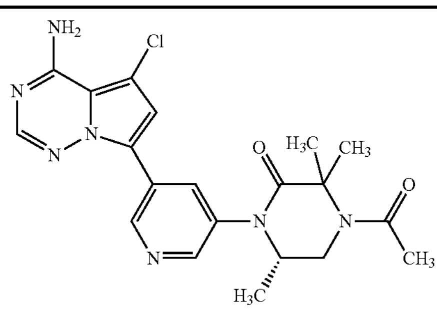 | (S)-4-acetyl-1-(5-(4-amino-5-chloropyrrolo[2,1-f][1,2,4]triazin-7-yl)pyridin-3-yl)-3,3,6-trimethylpiperazin-2-one | 428 |

TABLE 14-continued

| Ex. No. | Structure | Name | M + H |
|---|---|---|---|
| 92 | 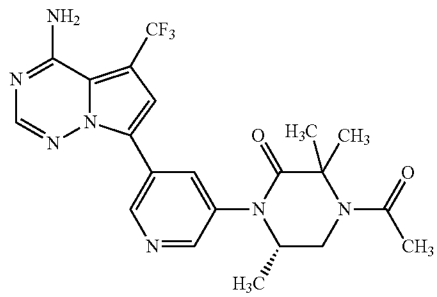 | (S)-4-acetyl-1-(5-(4-amino-5-(trifluoromethyl)pyrrolo[2,1-f][1,2,4]triazin-7-yl)pyridin-3-yl)-3,3,6-trimethylpiperazin-2-one | 461 |
| 93 | 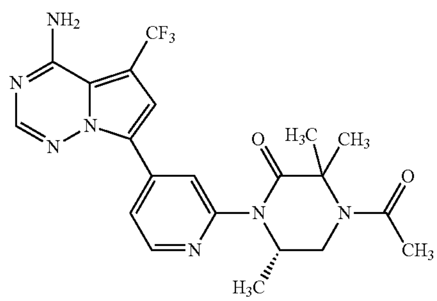 | (S)-4-acetyl-1-(4-(4-amino-5-(trifluoromethyl)pyrrolo[2,1-f][1,2,4]triazin-7-yl)pyridin-2-yl)-3,3,6-trimethylpiperazin-2-one | 461 |
| 94 | 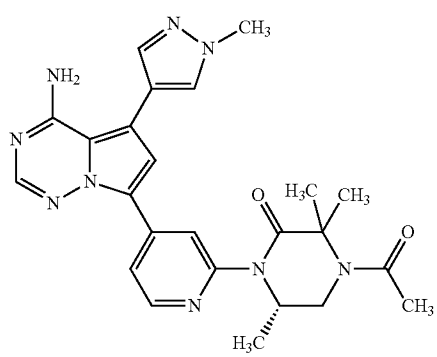 [SMILES: CC(=O)N1C[C@H](C)N(c2cc(-c3cc(-c4cnn(C)c4)c4c(N)ncnn34)ccn2)C(=O)C1(C)C] | (S)-4-acetyl-1-(4-(4-amino-5-(1-methyl-1H-pyrazol-4-yl)pyrrolo[2,1-f][1,2,4]triazin-7-yl)pyridin-2-yl)-3,3,6-trimethylpiperazin-2-one | 474 |
| 95 | 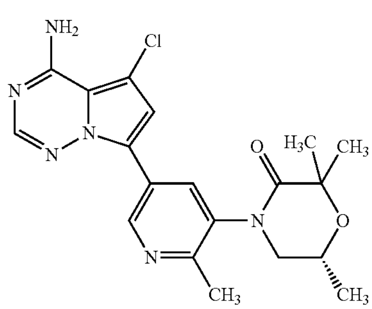 [SMILES: Cc1ncc(-c2cc(Cl)c3c(N)ncnn23)cc1N1C[C@@H](C)OC(C)(C)C1=O] | (R)-4-(5-(4-amino-5-chloropyrrolo[2,1-f][1,2,4]triazin-7-yl)-2-methylpyridin-3-yl)-2,2,6-trimethylmorpholin-3-one | 401 |

TABLE 14-continued

| Ex. No. | Structure | Name | M + H |
|---|---|---|---|
| 96 | 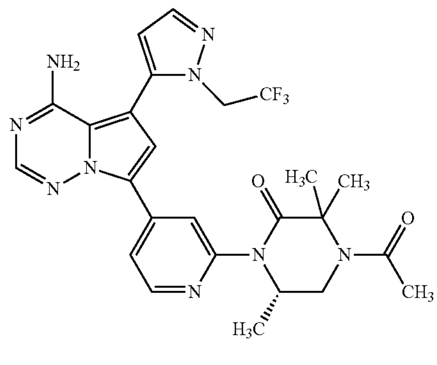 [SMILES: CC(=O)N1C[C@H](C)N(c2cc(-c3cc(-c4ccnn4CC(F)(F)F)c4c(N)ncnn34)ccn2)C(=O)C1(C)C] | (S)-4-acetyl-1-(4-(4-amino-5-(1-(2,2,2-trifluoroethyl)-1H-pyrazol-5-yl)pyrrolo[2,1-f][1,2,4]triazin-7-yl)pyridin-2-yl)-3,3,6-trimethylpiperazin-2-one | 542 |
| 97 | 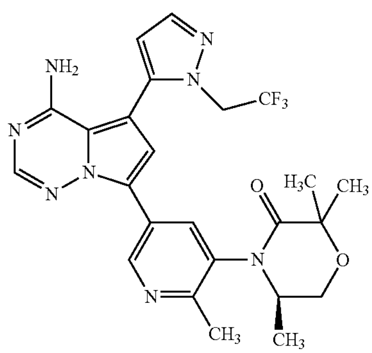 [SMILES: Cc1ncc(-c2cc(-c3ccnn3CC(F)(F)F)c3c(N)ncnn23)cc1N1C(=O)C(C)(C)OC[C@H]1C] | (R)-4-(5-(4-amino-5-(1-(2,2,2-trifluoroethyl)-1H-pyrazol-5-yl)pyrrolo[2,1-f][1,2,4]triazin-7-yl)-2-methylpyridin-3-yl)-2,2,5-trimethylmorpholin-3-one | 515 |
| 98 | 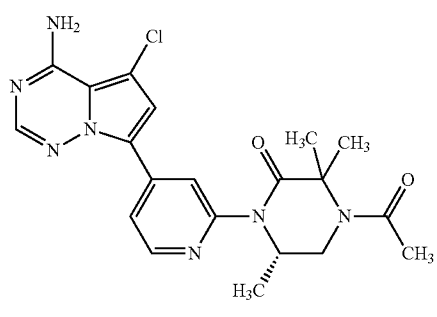 | (S)-4-acetyl-1-(4-(4-amino-5-chloropyrrolo[2,1-f][1,2,4]triazin-7-yl)pyridin-2-yl)-3,3,6-trimethylpiperazin-2-one | 428 |
| 99 | 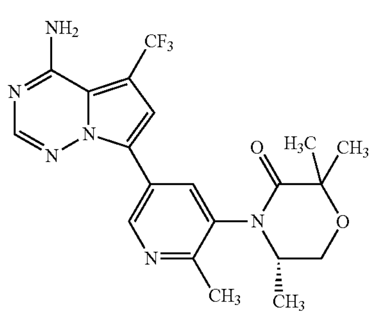 [SMILES: Cc1ncc(-c2cc(C(F)(F)F)c3c(N)ncnn23)cc1N1C(=O)C(C)(C)OC[C@@H]1C] | (S)-4-(5-(4-amino-5-(trifluoromethyl)pyrrolo[2,1-f][1,2,4]triazin-7-yl)-2-methylpyridin-3-yl)-2,2,5-trimethylmorpholin-3-one | 434 |

TABLE 14-continued

| Ex. No. | Structure | Name | M + H |
|---|---|---|---|
| 100 | 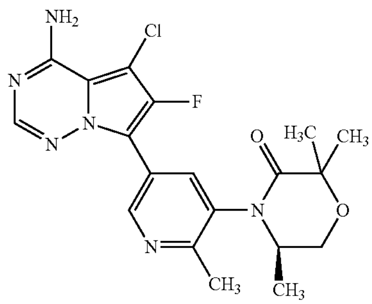 [SMILES: Cc1ncc(-c2c(F)c(Cl)c3c(N)ncnn23)cc1N1C(=O)C(C)(C)OC[C@H]1C] | (R)-4-(5-(4-amino-5-chloro-6-fluoropyrrolo[2,1-f][1,2,4]triazin-7-yl)-2-methylpyridin-3-yl)-2,2,5-trimethylmorpholin-3-one | 419 |
| 101 | 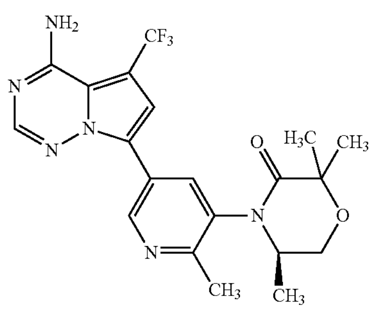 [SMILES: Cc1ncc(-c2cc(C(F)(F)F)c3c(N)ncnn23)cc1N1C(=O)C(C)(C)OC[C@H]1C] | (R)-4-(5-(4-amino-5-(trifluoromethyl)pyrrolo[2,1-f][1,2,4]triazin-7-yl)-2-methylpyridin-3-yl)-2,2,5-trimethylmorpholin-3-one | 434 |
| 102 | 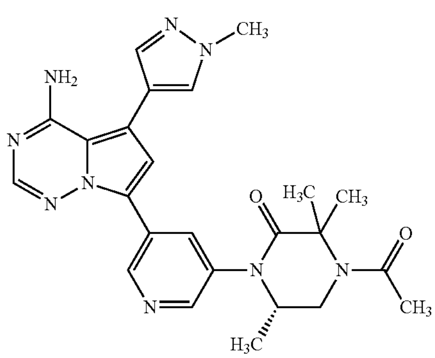 [SMILES: CC(=O)N1C[C@H](C)N(c2cncc(-c3cc(-c4cnn(C)c4)c4c(N)ncnn34)c2)C(=O)C1(C)C] | (S)-4-acetyl-1-(5-(4-amino-5-(1-methyl-1H-pyrazol-4-yl)pyrrolo[2,1-f][1,2,4]triazin-7-yl)pyridin-3-yl)-3,3,6-trimethylpiperazin-2-one | 474 |
| 103 | 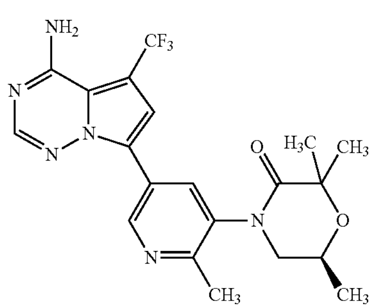 [SMILES: Cc1ncc(-c2cc(C(F)(F)F)c3c(N)ncnn23)cc1N1C[C@H](C)OC(C)(C)C1=O] | (S)-4-(5-(4-amino-5-(trifluoromethyl)pyrrolo[2,1-f][1,2,4]triazin-7-yl)-2-methylpyridin-3-yl)-2,2,6-trimethylmorpholin-3-one | 434 |

TABLE 14-continued

| Ex. No. | Structure | Name | M + H |
|---|---|---|---|
| 104 | 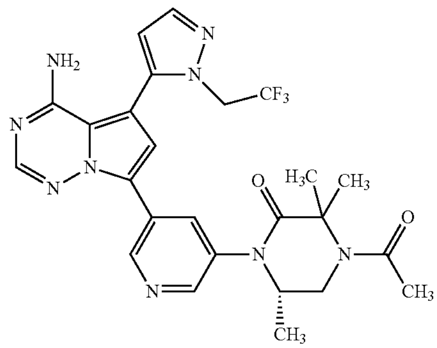 [SMILES: CC(=O)N1C[C@H](C)N(c2cncc(-c3cc(-c4ccnn4CC(F)(F)F)c4c(N)ncnn34)c2)C(=O)C1(C)C] | ((S)-4-acetyl-1-(5-(4-amino-5-(1-(2,2,2-trifluoroethyl)-1H-pyrazol-5-yl)pyrrolo[2,1-f][1,2,4]triazin-7-yl)pyridin-3-yl)-3,3,6-trimethylpiperazin-2-one | 542 |
| 105 | 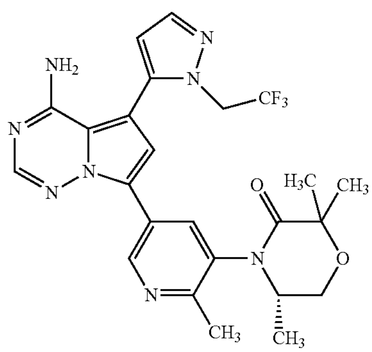 [SMILES: Cc1ncc(-c2cc(-c3ccnn3CC(F)(F)F)c3c(N)ncnn23)cc1N1C(=O)C(C)(C)OC[C@@H]1C] | (S)-4-(5-(4-amino-5-(1-(2,2,2-trifluoroethyl)-1H-pyrazol-5-yl)pyrrolo[2,1-f][1,2,4]triazin-7-yl)-2-methylpyridin-3-yl)-2,2,5-trimethylmorpholin-3-one | 515 |
| 106 | 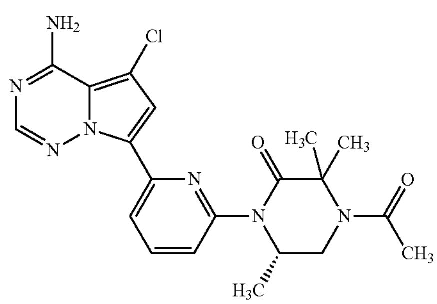 [SMILES: CC(=O)N1C[C@H](C)N(c2cccc(-c3cc(Cl)c4c(N)ncnn34)n2)C(=O)C1(C)C] | (S)-4-acetyl-1-(6-(4-amino-5-chloropyrrolo[2,1-f][1,2,4]triazin-7-yl)pyridin-2-yl)-3,3,6-trimethylpiperazin-2-one | 428 |
| 107 | 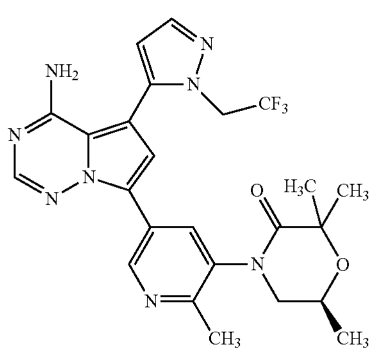 [SMILES: Cc1ncc(-c2cc(-c3ccnn3CC(F)(F)F)c3c(N)ncnn23)cc1N1C[C@H](C)OC(C)(C)C1=O] | (S)-4-(5-(4-amino-5-(1-(2,2,2-trifluoroethyl)-1H-pyrazol-5-yl)pyrrolo[2,1-f][1,2,4]triazin-7-yl)-2-methylpyridin-3-yl)-2,2,6-trimethylmorpholin-3-one | 515 |

TABLE 14-continued

| Ex. No. | Structure | Name | M + H |
|---|---|---|---|
| 108 | 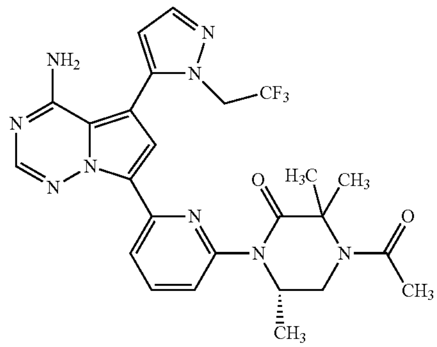 [SMILES: CC(=O)N1C[C@H](C)N(c2cccc(-c3cc(-c4ccnn4CC(F)(F)F)c4c(N)ncnn34)n2)C(=O)C1(C)C] | (S)-4-acetyl-1-(6-(4-amino-5-(1-(2,2,2-trifluoroethyl)-1H-pyrazol-5-yl)pyrrolo[2,1-f][1,2,4]triazin-7-yl)pyridin-2-yl)-3,3,6-trimethylpiperazin-2-one | 545 |
| 109 | 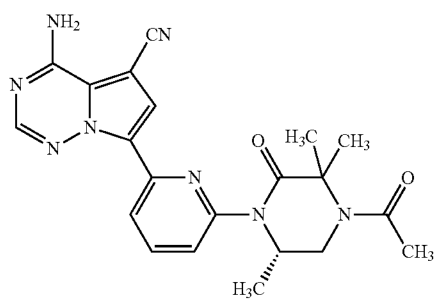 | (S)-7-(6-(4-acetyl-3,3,6-trimethyl-2-oxopiperazin-1-yl)pyridin-2-yl)-4-aminopyrrolo[2,1-f][1,2,4]triazine-5-carbonitrile | 418 |
| 110 | 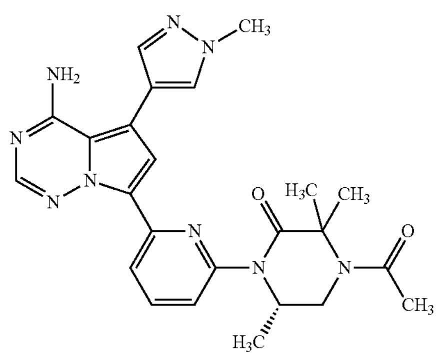 [SMILES: CC(=O)N1C[C@H](C)N(c2cccc(-c3cc(-c4cnn(C)c4)c4c(N)ncnn34)n2)C(=O)C1(C)C] | (S)-4-acetyl-1-(6-(4-amino-5-(1-methyl-1H-pyrazol-4-yl)pyrrolo[2,1-f][1,2,4]triazin-7-yl)pyridin-2-yl)-3,3,6-trimethylpiperazin-2-one | 474 |
| 111 | 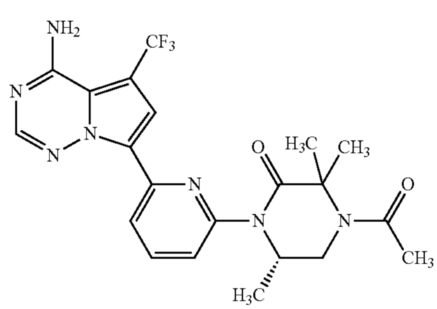 | (S)-4-acetyl-1-(6-(4-amino-5-(trifluoromethyl)pyrrolo[2,1-f][1,2,4]triazin-7-yl)pyridin-2-yl)-3,3,6-trimethylpiperazin-2-one | 461 |

TABLE 14-continued

| Ex. No. | Structure | Name | M + H |
|---|---|---|---|
| 112 | 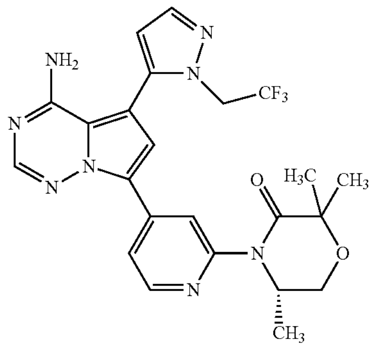 [SMILES: C[C@H]1COC(C)(C)C(=O)N1c1cc(-c2cc(-c3ccnn3CC(F)(F)F)c3c(N)ncnn23)ccn1] | (S)-4-(4-(4-amino-5-(1-(2,2,2-trifluoroethyl)-1H-pyrazol-5-yl)pyrrolo[2,1-f][1,2,4]triazin-7-yl)pyridin-2-yl)-2,2,5-trimethylmorpholin-3-one | 500 |
| 113 | 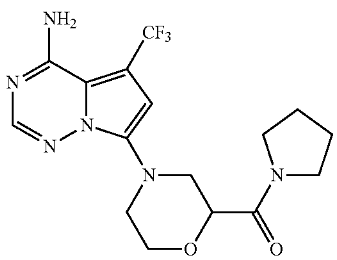 [SMILES: Nc1ncnn2c(N3CCOC(C(=O)N4CCCC4)C3)cc(C(F)(F)F)c12] | (4-(4-amino-5-(trifluoromethyl)pyrrolo[2,1-f][1,2,4]triazin-7-yl)morpholin-2-yl)(pyrrolidin-1-yl)methanone | 384 |
| 114 | 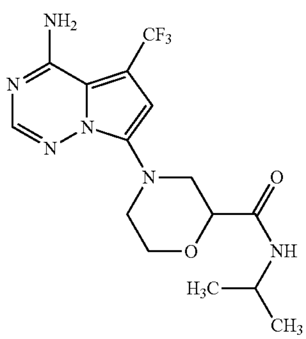 [SMILES: CC(C)NC(=O)C1CN(c2cc(C(F)(F)F)c3c(N)ncnn23)CCO1] | 4-(4-amino-5-(trifluoromethyl)pyrrolo[2,1-f][1,2,4]triazin-7-yl)-N-isopropylmorpholine-2-carboxamide | 372 |
| 115 | 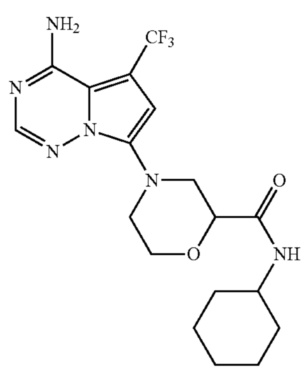 [SMILES: Nc1ncnn2c(N3CCOC(C(=O)NC4CCCCC4)C3)cc(C(F)(F)F)c12] | 4-(4-amino-5-(trifluoromethyl)pyrrolo[2,1-f][1,2,4]triazin-7-yl)-N-cyclohexylmorpholine-2-carboxamide | 412 |
| 116 | 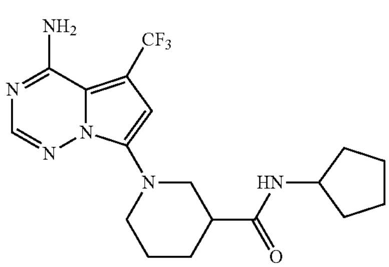 [SMILES: Nc1ncnn2c(N3CCCC(C(=O)NC4CCCC4)C3)cc(C(F)(F)F)c12] | 1-(4-amino-5-(trifluoromethyl)pyrrolo[2,1-f][1,2,4]triazin-7-yl)-N-cyclopentylpiperidine-3-carboxamide | 396 |

TABLE 14-continued

| Ex. No. | Structure | Name | M + H |
|---|---|---|---|
| 117 | 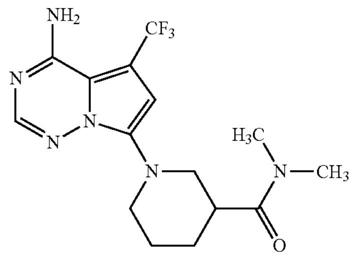 [SMILES: CN(C)C(=O)C1CCCN(c2cc(C(F)(F)F)c3c(N)ncnn23)C1] | 1-(4-amino-5-(trifluoromethyl)pyrrolo[2,1-f][1,2,4]triazin-7-yl)-N,N-dimethylpiperidine-3-carboxamide | 356 |
| 118 | 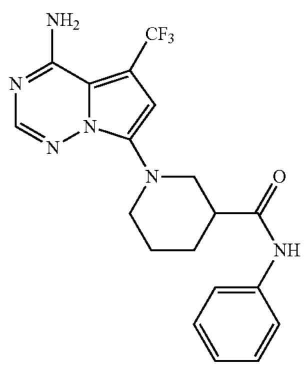 [SMILES: Nc1ncnn2c(N3CCCC(C(=O)Nc4ccccc4)C3)cc(C(F)(F)F)c12] | 1-(4-amino-5-(trifluoromethyl)pyrrolo[2,1-f][1,2,4]triazin-7-yl)-N-phenylpiperidine-3-carboxamide | 404 |
| 119 | 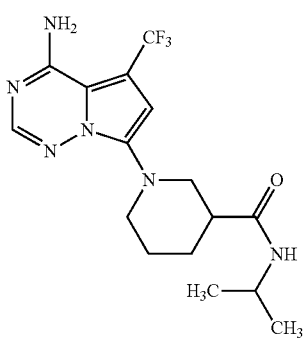 [SMILES: CC(C)NC(=O)C1CCCN(c2cc(C(F)(F)F)c3c(N)ncnn23)C1] | 1-(4-amino-5-(trifluoromethyl)pyrrolo[2,1-f][1,2,4]triazin-7-yl)-N-isopropylpiperidine-3-carboxamide | 370 |

Biological Assays

The pharmacological properties of the compounds of this invention may be confirmed by a number of biological assays. The exemplified biological assays, which follow, have been carried out with compounds of the invention.

ADP-Glo Format PI3K Assays

The ADP-Glo format PI3K assays were performed in Proxiplate 384-well plates (Perkin Elmer #6008280). The final assay volume was 2 µl prepared from 1 µl additions of enzyme/PIP2:PS lipid (Invitrogen #PV5100) mixture and 1 µl ATP (provided in kit, Promega #V9101) and test compounds in assay buffer (50 mM HEPES pH 7.5, 3 mM MgCl$_2$, 100 mM NaCl, 0.5 mM EGTA, 2 mM DTT, 0.03% CHAPS). The reaction was initiated by the combination of enzyme/lipid, ATP, and test compounds. The reaction mixture was incubated at room temperature for 30 minutes (PI3K Alpha, Beta, Gamma) or 3 hours for PI3K Delta. ADP-Glo (2 µl), followed by Kinase Detection reagent (4 µl), were added to reactions following the initial incubation and allowed to incubate 40 minutes at room temperature. The reaction mixture was analyzed on the TOPCOUNT® (Perkin Elmer). Inhibition data were calculated by comparison to no enzyme control reactions for 100% inhibition and vehicle-only reactions for 0% inhibition. The final concentration of enzyme in the assays are PI3K Alpha [0.5 nM], PI3K Beta [2 nM], PI3K Gamma [20 nM], PI3K Delta [0.5 nM]. ATP final concentrations are as follows: for Alpha [10 µM], for Beta [12.5 µM], for Gamma [6.5 µM], for Delta [100 µM]. Lipid final concentration was the same for all enzymes, [25 µM]. Dose response curves were generated to determine the concentration required to inhibit 50% of activity. Compounds were dissolved at 0.12 mM in dimethylsulfoxide (DMSO) and evaluated at eleven concentrations. The IC$_{50}$ values were derived by non-linear regression analysis.

Whole Blood Assay of BCR-Stimulated CD69 Expression on B Cells

The efficacy of PI3K inhibitor compounds in suppressing CD69 expression on B cells human in whole blood assays is useful for predicting efficacious doses in the clinic and minimizing potential side-effects. PI3K inhibitor compounds having higher activity in the whole blood CD69 expression assay are expected to require lower doses than compounds having lower activity, and are expected to cause fewer unwanted side-effects. (Uetrecht, *Chem. Res. Toxicol.*, 12:387-395 (1999); Nakayama, *Drug Metabolism and Disposition*, 37(9):1970-1977 (2009); Sakatis, *Chemical Research in Toxicology* (2012)).

To measure BCR-stimulated B cells, ACD-A human whole blood was treated with various concentrations of test compound and stimulated with 30 μg/mL AffiniPure F(ab')2 fragment goat anti human IgM (Jackson 109-006-1299—endotoxin cleared) and 10 ng/mL human IL-4 (Peprotech 200-04) for 18 h at 37° C. with agitation. The cells were blocked with human gamma globulin (Jackson 009-000-002) and stained with FITC-conjugated mouse anti-human CD20 (BD Pharmingen 555622) and PE-conjugated mouse anti-human CD69 monoclonal antibody (BD Pharmingen 555531), lysed and fixed, then washed. The amount of CD69 expression was quantitated by the median fluorescence intensity (MFI) after gating on the CD20-positive B cell population as measured by FACS analysis.

In the whole blood assay of BCR-Stimulated CD69 expression on B cells, increased efficacy of a PI3K inhibitor compound is indicated by a lower CD69 $IC_{50}$ value.

The exemplified Examples disclosed below were tested in one or both of the ADP-Glo format PI3K assays and the Whole Blood Assay of BCR-Stimulated CD69 Expression on B Cells, each described above. The exemplified Examples disclosed below were found to have PI3K delta inhibitory activity. Table 11 lists the $IC_{50}$ values measured in the ADP-Glo format PI3K delta assay and Table 12 lists the CD69 $IC_{50}$ values measured the Whole Blood Assay of BCR-Stimulated CD69 Expression on B Cells for the following Examples.

TABLE 11

| Example | PI3K delta $IC_{50}$ value (nM) |
| --- | --- |
| 1 | 5 |
| 2 | 14 |
| 3 | 9 |
| 4 | 5 |
| 5 | 5 |
| 6 | 6 |
| 7 | 5 |
| 8 | 2 |
| 9 | 2 |
| 10 | 4 |
| 11 | 0.6 |
| 12 | 0.4 |
| 13 | 1 |
| 14 | 1 |
| 15 | 0.6 |
| 16 | 1 |
| 17 | 6 |
| 18 | 4 |
| 19 | 2 |
| 20 | 2 |
| 21 | 1 |
| 22 | 4 |
| 23 | 5 |
| 24 | 2 |
| 25 | 2 |
| 26 | 7 |
| 27 | 2 |
| 28 | 2 |
| 29 | 2 |
| 30 | 2 |
| 31 | 2 |
| 32 | 1 |
| 33 | 2 |

TABLE 11-continued

| Example | PI3K delta $IC_{50}$ value (nM) |
| --- | --- |
| 34 | 8 |
| 35 | 4 |
| 36 | 2 |
| 37 | 4 |
| 38 | 12 |
| 39 | 2 |
| 40 | 3 |
| 41 | 9 |
| 42 | 8 |
| 43 | 6 |
| 44 | 5 |
| 45 | 2 |
| 46 | 1 |
| 47 | 3 |
| 48 | 3 |
| 49 | 9 |
| 50 | 8 |
| 51 | 5 |
| 52 | 5 |
| 54 | 10 |
| 55 | 2 |
| 56 | 6 |
| 57 | 9 |
| 58 | 9 |
| 59 | 8 |
| 60 | 5 |
| 61 | 4 |
| 62 | 2 |
| 63 | 1 |
| 64 | 4 |
| 65 | 5 |
| 66 | 3 |
| 67 | 3 |
| 68 | 5 |
| 69 | 3 |
| 70 | 4 |
| 71 | 6 |
| 72 | 8 |
| 73 | 11 |
| 74 | 14 |
| 75 | 24 |
| 76 | 40 |
| 77 | 64 |
| 78 | 9 |
| 79 | 4 |
| 80 | 2 |
| — | — |
| 81 | 2 |
| 82 | 25 |
| 83 | 3 |
| 84 | 1 |
| 85 | 3 |
| 86 | 2 |
| 87 | 4 |
| 88 | 2 |
| 89 | 2 |
| 90 | 1 |
| 91 | 0.55 |
| 92 | 1 |
| 93 | 1 |
| 94 | — |
| 95 | 11 |
| 96 | 14 |
| 97 | 13 |
| 98 | 1 |
| 99 | 2 |
| 100 | 10 |
| 101 | 2 |
| 102 | 1 |
| 103 | 28 |
| 104 | 1 |
| 105 | 7 |
| 106 | 13 |
| 107 | 13 |
| 108 | 18 |
| 109 | 2 |
| 110 | 3 |

TABLE 11-continued

| Example | PI3K delta IC$_{50}$ value (nM) |
|---|---|
| 111 | 2 |
| 112 | 4 |
| 113 | 111 |
| 114 | 644 |
| 115 | 210 |
| 116 | 357 |
| 117 | 847 |
| 118 | 214 |
| 119 | 295 |
| — | — |

TABLE 12

| Example | CD69 IC$_{50}$ values (nM) |
|---|---|
| 33 | 41 |
| 36 | 427 |
| 69 | 659 |
| 70 | 351 |
| 71 | 931 |
| 72 | 4349 |
| 73 | 1088 |
| 74 | 1746 |
| 75 | 2757 |
| 76 | 1446 |
| 77 | 1644 |
| 78 | 717 |
| 79 | 454 |
| 83 | 116 |
| 84 | 51 |
| 85 | 82 |
| 86 | 111 |
| 87 | 174 |
| 88 | 242 |
| 89 | 250 |
| 90 | 24 |
| 91 | 3.4 |
| 92 | 20 |
| 93 | 400 |
| 94 | 160 |
| 95 | 350 |
| 96 | 370 |
| 97 | 600 |
| 98 | 110 |
| 99 | 230 |
| 100 | 360 |
| 101 | 60 |
| 102 | 190 |
| 103 | 580 |
| 104 | 60 |
| 105 | 140 |
| 106 | 320 |
| 107 | 350 |
| 108 | 1360 |
| 109 | 160 |
| 110 | 170 |
| 111 | 160 |
| 112 | 200 |
| 113 | 2820 |
| 114 | 3570 |
| 115 | 10000 |
| 116 | 10000 |
| 117 | 10000 |
| 118 | 10000 |
| 119 | 10000 |
| — | — |

The compounds of the present invention possess activity as inhibitors of PI3K delta, and therefore, may be used in the treatment of diseases associated with PI3K activity.

The invention claimed is:

1. A compound of Formula (I):

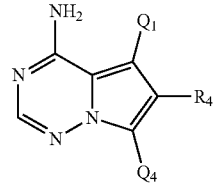

or a salt thereof; wherein:

$Q_1$ is:
  (i) Cl, I, —CN, —CH$_3$, or —CF$_3$; or
  (ii) pyrazolyl, triazolyl, or pyridinyl, each substituted with $R_1$;

$R_1$ is $C_{1-3}$ alkyl, $C_{1-3}$ fluoroalkyl, $C_{3-6}$ cycloalkyl, —NHC(O)($C_{1-3}$ alkyl), or tetrahydropyranyl;

$Q_2$ is morpholinyl, piperidinyl, pyridinyl, indazolyl, isoquinolinyl, or benzo[d]imidazolyl, each substituted with $R_2$ and $R_3$;

$R_2$ is H, F, Cl, Br, $C_{1-3}$ alkyl, $C_{1-3}$ fluoroalkyl, —C(O)(pyrrolidinyl), —C(O)NR$_a$R$_a$, —CH$_2$C(O)NR$_a$R$_a$, —C(O)NR$_a$($C_{4-6}$ cycloalkyl), —C(O)NR$_a$(phenyl), $C_{1-3}$ hydroxy-fluoroalkyl, —CH$_2$($C_{3-6}$ cycloalkyl), —CH$_2$($C_{3-6}$ fluorocycloalkyl), =O, R$_x$, or —CH$_2$R$_x$;

$R_x$ is isoxazolyl, pyrrolidinonyl, tetrahydropyranyl, thiopyran 1,1-dioxide, morpholinyl, morpholinonyl, thiomorpholine 1,1-dioxide, pyridinonyl, phenyl, piperazinyl, piperazinonyl, or piperidinyl, each substituted with zero to 5 substituents independently selected from $C_{1-3}$ alkyl, —C(O)NR$_a$R$_a$, —C(O)($C_{1-3}$ alkyl), —C(O)($C_{1-3}$ hydroxyalkyl), —C(O)($C_{3-6}$ cycloalkyl), —C(O)CH$_2$O($C_{1-3}$ alkyl), —NHC(O)($C_{1-3}$ alkyl), —S(O)$_2$($C_{1-3}$ alkyl), and oxetanyl;

$R_3$ is H, F, or —CH$_3$;

$R_4$ is H or F; and each $R_a$ is independently H or $C_{1-3}$ alkyl.

2. The compound according to claim 1 or a salt thereof; wherein:

$R_1$ is —CH$_3$, —CH(CH$_3$)$_2$, —CH$_2$CF$_3$, —CH(CH$_3$)CF$_3$, cyclopropyl, cyclohexyl, —NHC(O)CH$_3$, or tetrahydropyranyl; and $R_2$ is H, Br, —CH$_3$, —CH(CH$_3$)$_2$, —CH$_2$CH$_2$F, —CH$_2$C(O)N(CH$_3$)$_2$, —CH$_2$CH(OH)CH$_2$F, —CH$_2$(cyclopropyl), —CH$_2$(difluorocyclopropyl), —CH$_2$(methyl isoxazolyl), —CH$_2$(pyrrolidinonyl), =O, tetrahydropyranyl, dimethyl tetrahydropyranyl, thiopyran 1,1-dioxide, morpholinyl, thiomorpholine 1,1-dioxide, methyl pyridinonyl, phenyl substituted with —C(O)NH$_2$, NHC(O)CH$_3$, or —S(O)$_2$CH$_3$; piperazinyl or piperazinonyl, each substituted with zero to 5 substituents independently selected from —CH$_3$, —C(O)CH$_3$, —C(O)(cyclopropyl), and oxetanyl; or piperidinyl or piperidinonyl, each substituted with —CH$_3$, —C(O)CH$_3$, —C(O)CH$_2$OH, or —C(O)CH$_2$OCH$_3$.

3. The compound according to claim 1 or a salt thereof, wherein $Q_2$ is:

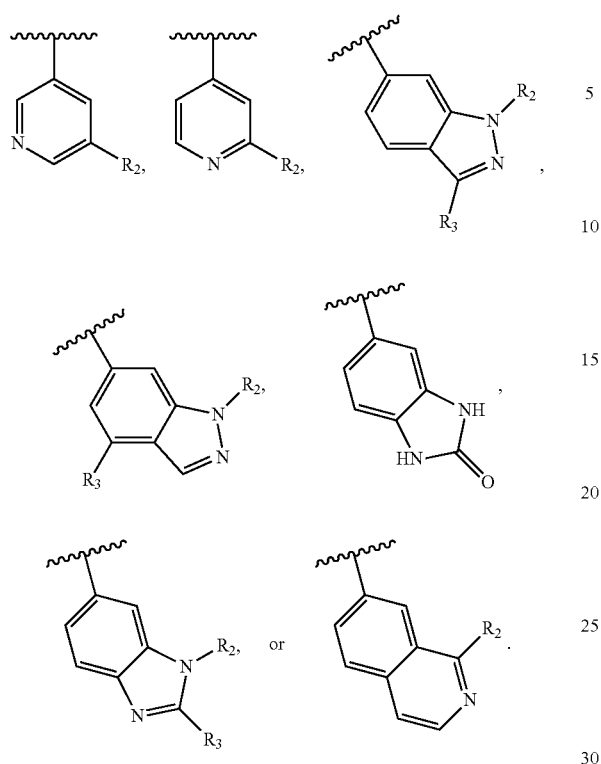
4. The compound according to claim 1 or a salt thereof, wherein:
$Q_1$ is Cl, I, —CN, or —CF$_3$.
5. The compound according to claim 1 or a salt thereof, wherein:
$Q_1$ is pyrazolyl, triazolyl, or pyridinyl, each substituted with $R_1$.
6. The compound according to claim 1 or a salt thereof, wherein $Q_2$ is:
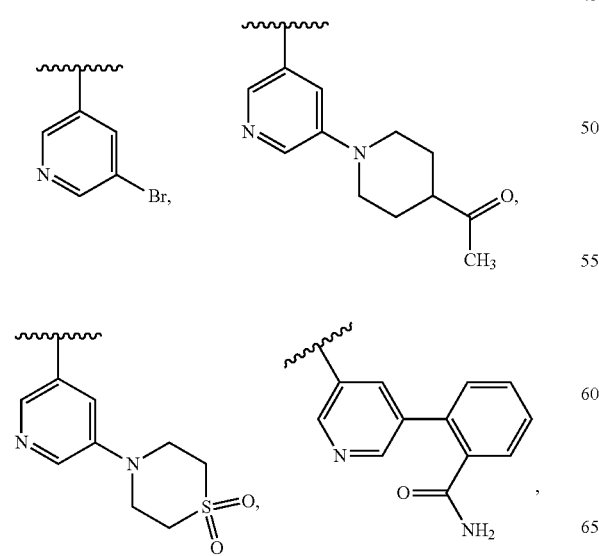
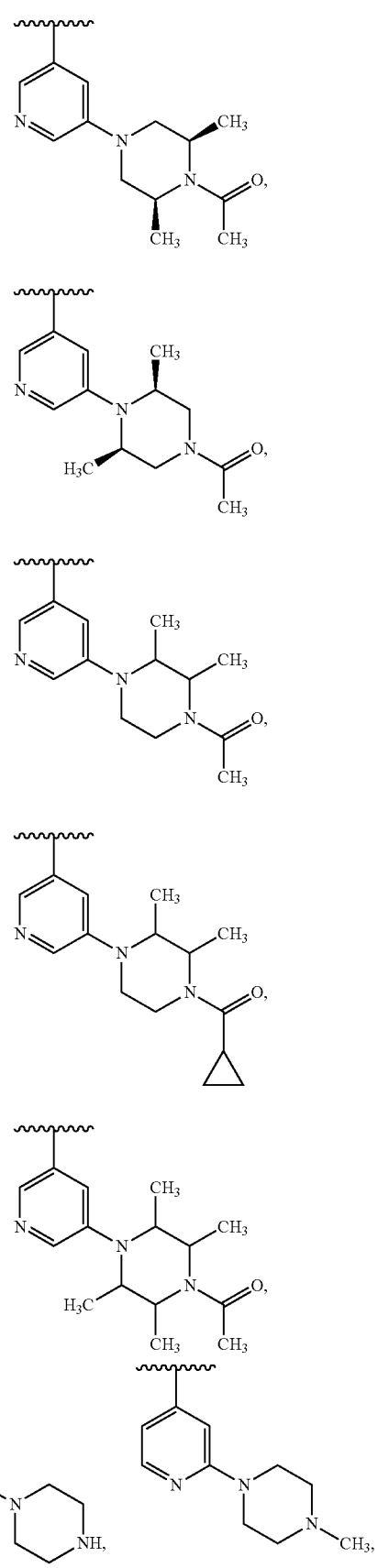

131
-continued
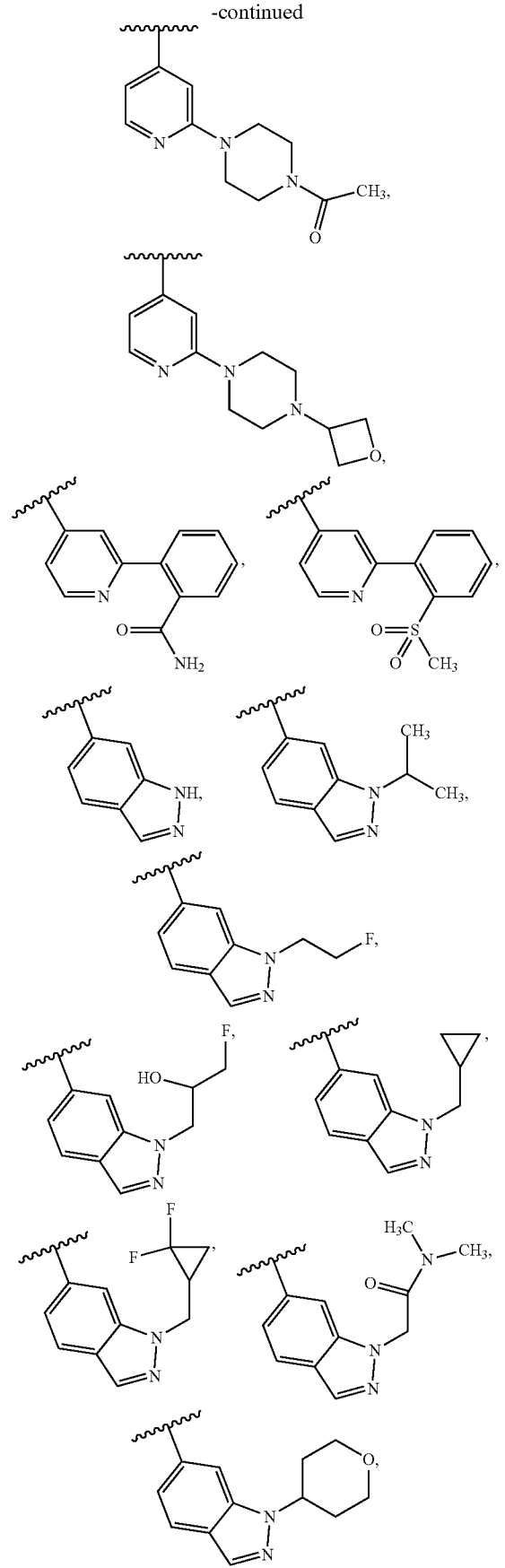
132
-continued
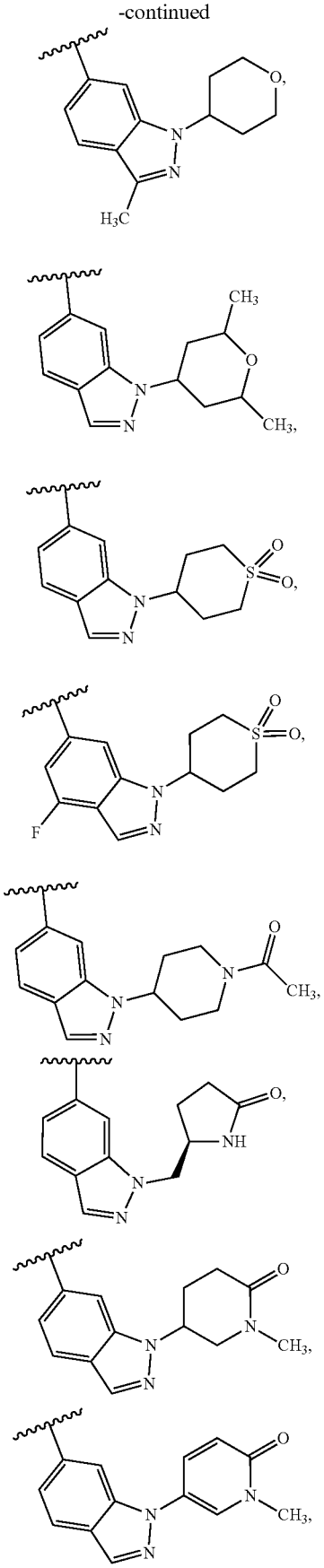

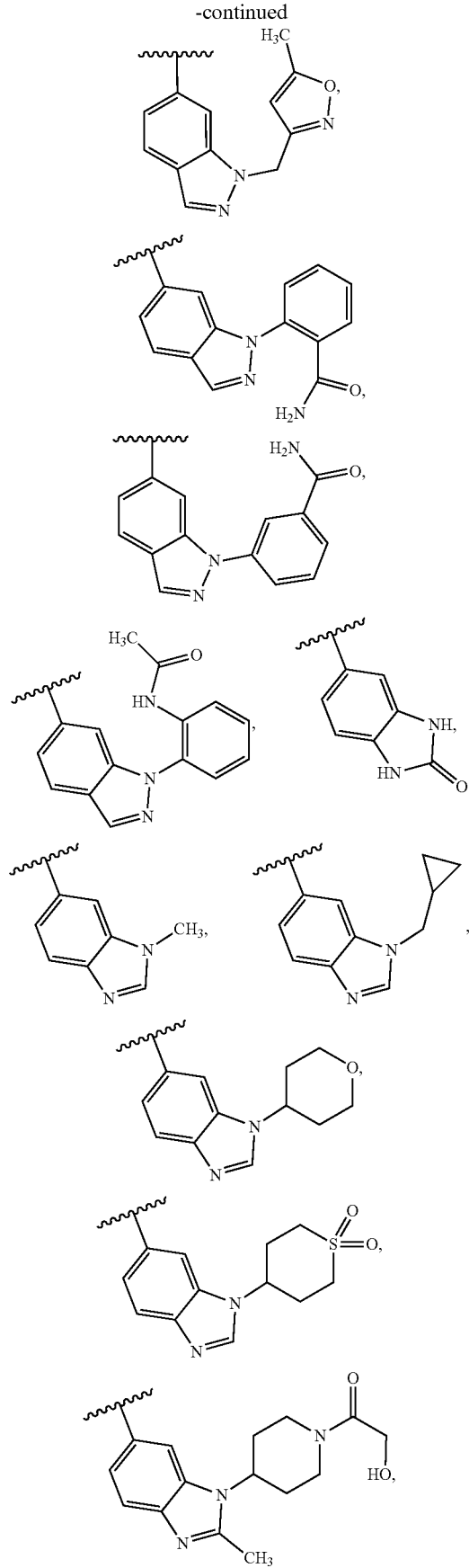
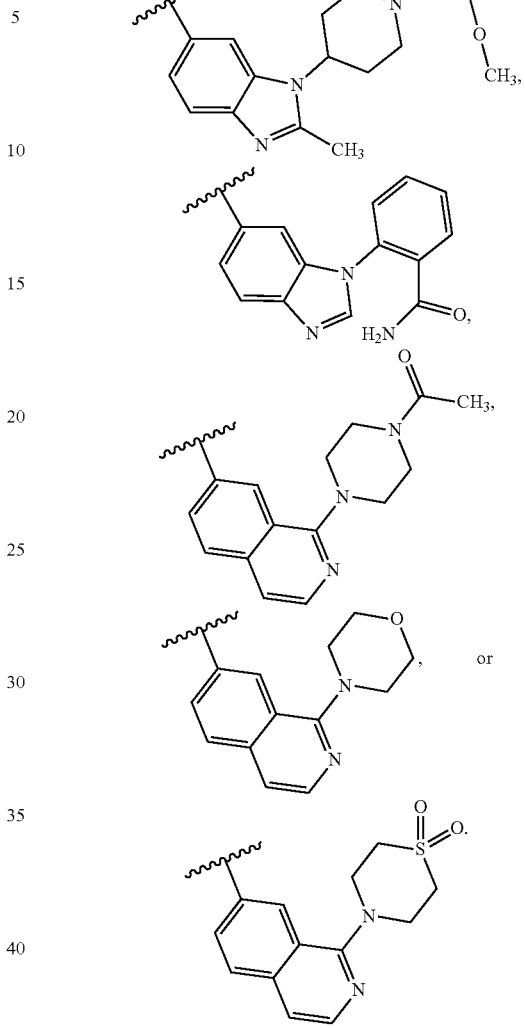

7. The compound according to claim 1 or a salt thereof, wherein said compound is selected from 1-(4-(5-(4-amino-5-(1-(tetrahydro-2H-pyran-4-yl)-1H-pyrazol-5-yl)pyrrolo[2,1-f][1,2,4]triazin-7-yl)pyridin-3-yl)piperazin-1-yl)ethanone, TFA (1); 5-(4-amino-5-(1-cyclohexyl-1H-pyrazol-5-yl)pyrrolo[2,1-J][1,2,4]triazin-7-yl)-1H-benzo[d]imidazol-2(3H)-one (2); 5-(1-cyclohexyl-1H-pyrazol-5-yl)-7-(1-methyl-1H-benzo[d]imidazol-6-yl)pyrrolo[2,1-f][1,2,4]triazin-4-amine (3); 1-(4-(5-(4-amino-5-(1-(tetrahydro-2H-pyran-4-yl)-1H-1,2,3-triazol-5-yl)pyrrolo[2,1-f][1,2,4]triazin-7-yl)pyridin-3-yl)piperazin-1-yl)ethanone, TFA (4); 1-(4-(5-(4-amino-5-(1-isopropyl-1H-1,2,3-triazol-5-yl)pyrrolo[2,1-f][1,2,4]triazin-7-yl)pyridin-3-yl)piperazin-1-yl)ethanone, TFA (5); 4-(5-(4-amino-5-(1-(tetrahydro-2H-pyran-4-yl)-1H-pyrazol-5-yl)pyrrolo[2,1-f][1,2,4]triazin-7-yl)pyridin-3-yl)thiomorpholine 1,1-dioxide (6); 4-(5-(4-amino-5-(1-(tetrahydro-2H-pyran-4-yl)-1H-1,2,3-triazol-5-yl)pyrrolo[2,1-f][1,2,4]triazin-7-yl)pyridin-3-yl) thiomorpholine 1,1-dioxide (7); 4-(5-(4-amino-5-(1-isopropyl-1H-1,2,3-triazol-5-yl)pyrrolo[2,1-f][1,2,4]triazin-7-yl)pyridin-3-yl)thiomorpholine 1,1-dioxide (8); 1-((cis)-4-(5-(4-amino-5-(1-(tetrahydro-2H-pyran-4-yl)-1H- pyrazol-5-yl)pyrrolo[2,1-f][1,2,4]triazin-7-yl)pyridin-3-yl)-2,6-dimethylpiperazin-1-yl)ethanone (9); 1-((cis)-4-(5-(4-amino-5-(1-(tetrahydro-2H-pyran-4-yl)-1H-1,2,3-triazol-5-yl)pyrrolo[2,1-f][1,2,4]triazin-7-yl)pyridin-3-yl)-2,6-dimethylpiperazin-1-yl)ethanone (10); 1-((cis)-4-(5-(4-amino-5-(1-(tetrahydro-2H-pyran-4-yl)-1H-pyrazol-5-yl)pyrrolo[2,1-f][1,2,4]triazin-7-yl)pyridin-3-yl)-3,5-dimethylpiperazin-1-yl)ethanone (11); 1-((cis)-4-(5-(4-amino-5-(1-(tetrahydro-2H-pyran-4-yl)-1H-1,2,3-triazol-5-yl)pyrrolo[2,1-f][1,2,4]triazin-7-yl)pyridin-3-yl)-3,5-dimethylpiperazin-1-yl) ethanone (12); 1-((cis)-4-(5-(4-amino-5-(1-isopropyl-1H-1,2,3-triazol-5-yl)pyrrolo[2,1-f][1,2,4]triazin-7-yl)pyridin-3-yl)-3,5-dimethylpiperazin-1-yl)ethanone (13); 1-(4-(5-(4-amino-5-(1-(tetrahydro-2H-pyran-4-yl)-1H-pyrazol-5-yl)pyrrolo[2,1-f][1,2,4]triazin-7-yl) pyridin-3-yl)-2,3,5,6-tetramethylpiperazin-1-yl) ethanone (14); 1-(4-(5-(4-amino-5-(1-(tetrahydro-2H-pyran-4-yl)-1H-1,2,3-triazol-5-yl)pyrrolo[2,1-f][1,2,4]triazin-7-yl)pyridin-3-yl)-2,3,5,6-tetramethylpiperazin-1-yl)ethanone (15); 7-(1-(tetrahydro-2H-pyran-4-yl)-1H-indazol-6-yl)-5-(1-(tetrahydro-2H-pyran-4-yl)-1H-pyrazol-5-yl)pyrrolo[2,1-f][1,2,4]triazin-4-amine (16); 7-(1-(2-fluoroethyl)-1H-indazol-6-yl)-5-(1-(tetrahydro-2H-pyran-4-yl)-1H-pyrazol-5-yl)pyrrolo [2,1-f][1,2,4]triazin-4-amine (17); 5-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)-1-methylpyridin-2(1H)-one (18); 5-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)-1-methylpiperidin-2-one (19); 1-(4-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)piperidin-1-yl)ethanone (20); 1-(4-(6-(4-amino-5-(1-(tetrahydro-2H-pyran-4-yl)-1H-1,2,3-triazol-5-yl)pyrrolo[2,1-f][1,2,4]triazin-7-yl)-1H-indazol-1-yl) piperidin-1-yl)ethanone (21); 1-(4-(6-(4-amino-5-(1-(tetrahydro-2H-pyran-4-yl)-1H-pyrazol-5-yl)pyrrolo[2,1-f][1,2,4]triazin-7-yl)-2-methyl-1H-benzo[d]imidazol-1-yl)piperidin-1-yl)-2-hydroxyethanone (22); 1-(4-(6-(4-amino-5-(1-(tetrahydro-2H-pyran-4-yl)-1H-pyrazol-5-yl)pyrrolo[2,1-f][1,2,4]triazin-7-yl)-2-methyl-1H-benzo[d]imidazol-1-yl) piperidin-1-yl)-2-methoxyethanone (23); 5-(1-(tetrahydro-2H-pyran-4-yl)-1H-1,2,3-triazol-5-yl)-7-(1-(tetrahydro-2H-pyran-4-yl)-1H-indazol-6-yl)pyrrolo[2,1-f][1,2,4]triazin-4-amine (24); 5-(1-isopropyl-1H-1,2,3-triazol-5-yl)-7-(1-(tetrahydro-2H-pyran-4-yl)-1H-indazol-6-yl)pyrrolo[2,1-f][1,2,4]triazin-4-amine (25); 5-(1-cyclohexyl-1H-1,2,3-triazol-5-yl)-7-(1-(tetrahydro-2H-pyran-4-yl)-1H-indazol-6-yl)pyrrolo[2,1-f][1,2,4]triazin-4-amine (26); 7-(1-(2,6-dimethyltetrahydro-2H-pyran-4-yl)-1H-indazol-6-yl)-5-(1-(tetrahydro-2H-pyran-4-yl)-1H-pyrazol-5-yl)pyrrolo[2,1-f][1,2,4]triazin-4-amine (27); 7-(3-methyl-1-(tetrahydro-2H-pyran-4-yl)-1H-indazol-6-yl)-5-(1-(tetrahydro-2H-pyran-4-yl)-1H-pyrazol-5-yl)pyrrolo [2,1-f][1,2,4]triazin-4-amine (28); 7-(3-methyl-1-(tetrahydro-2H-pyran-4-yl)-1H-indazol-6-yl)-5-(1-(tetrahydro-2H-pyran-4-yl)-1H-1,2,3-triazol-5-yl)pyrrolo[2,1-f][1,2,4]triazin-4-amine (29); 7-(1-(tetrahydro-2H-pyran-4-yl)-1H-benzo[d]imidazol-6-yl)-5-(1-(tetrahydro-2H-pyran-4-yl)-1H-pyrazol-5-yl)pyrrolo[2,1-f][1,2,4]triazin-4-amine (30); 5-(1-(tetrahydro-2H-pyran-4-yl)-1H-1,2,3-triazol-5-yl)-7-(1-(tetrahydro-2H-pyran-4-yl)-1H-benzo[d]imidazol-6-yl)pyrrolo[2,1-f][1,2,4]triazin-4-amine (31); 5-(1-cyclohexyl-1H-1,2,3-triazol-5-yl)-7-(1-(tetrahydro-2H-pyran-4-yl)-1H-benzo[d]imidazol-6-yl)pyrrolo[2,1-f][1,2,4]triazin-4-amine (32); 4-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)tetrahydro-2H-thiopyran 1,1-dioxide (33); 4-(6-(4-amino-5-(1-(2,2,2-trifluoroethyl)-1H-pyrazol-5-yl)pyrrolo[2,1-f][1,2,4]triazin-7-yl)-1H-indazol-1-yl)tetrahydro-2H-thiopyran 1,1-dioxide (34); 4-(6-(4-amino-5-(1-cyclohexyl-1H-1,2,3-triazol-5-yl)pyrrolo[2,1-f][1,2,4]triazin-7-yl)-1H-indazol-1-yl) tetrahydro-2H-thiopyran 1,1-dioxide (35); 4-(6-(4-amino-5-(1-(tetrahydro-2H-pyran-4-yl)-1H-1,2,3-triazol-5-yl)pyrrolo[2,1-f][1,2,4]triazin-7-yl)-4-fluoro-1H-indazol-1-yl) tetrahydro-2H-thiopyran 1,1-dioxide (36); 4-(6-(4-amino-5-(1-(tetrahydro-2H-pyran-4-yl)-1H-pyrazol-5-yl)pyrrolo[2,1-f][1,2,4]triazin-7-yl)-4-fluoro-1H-indazol-1-yl)tetrahydro-2H-thiopyran 1,1-dioxide (37); 4-(6-(4-amino-5-(1-cyclopropyl-1H-pyrazol-5-yl)pyrrolo [2,1-f][1,2,4]triazin-7-yl)-4-fluoro-1H-indazol-1-yl)tetrahydro-2H-thiopyran 1,1-dioxide (38); 4-(6-(4-amino-5-(1-(tetrahydro-2H-pyran-4-yl)-1H-pyrazol-5-yl)pyrrolo[2,1-f][1,2,4]triazin-7-yl)-1H-benzo[d]imidazol-1-yl)tetrahydro-2H-thiopyran 1,1-dioxide (39); 4-(6-(4-amino-5-(1-(tetrahydro-2H-pyran-4-yl)-1H-1,2,3-triazol-5-yl)pyrrolo[2,1-f][1,2,4]triazin-7-yl)-1H-benzo[d]imidazol-1-yl)tetrahydro-2H-thiopyran 1,1-dioxide (40); 4-(6-(4-amino-5-(1-(2,2,2-trifluoroethyl)-1H-pyrazol-5-yl)pyrrolo[2,1-f][1,2,4]triazin-7-yl)-1H-benzo[d]imidazol-1-yl)tetrahydro-2H-thiopyran 1,1-dioxide (41); 7-(1-isopropyl-1H-indazol-6-yl)-5-(1-(tetrahydro-2H-pyran-4-yl)-1H-pyrazol-5-yl)pyrrolo[2,1-f][1,2,4]triazin-4-amine (42); 7-(1-(cyclopropylmethyl)-1H-indazol-6-yl)-5-(1-(tetrahydro-2H-pyran-4-yl)-1H-1,2,3-triazol-5-yl)pyrrolo[2,1-f][1,2,4]triazin-4-amine (43); 7-(1-(cyclopropylmethyl)-1H-indazol-6-yl)-5-(1-(tetrahydro-2H-pyran-4-yl)-1H-pyrazol-5-yl)pyrrolo[2,1-f][1,2,4]triazin-4-amine (44); 7-(1-(cyclopropylmethyl)-1H-benzo[d]imidazol-6-yl)-5-(1-(tetrahydro-2H-pyran-4-yl)-1H-1,2,3-triazol-5-yl)pyrrolo[2,1-f][1,2,4]triazin-4-amine (45); 7-(1-(cyclopropylmethyl)-1H-benzo[d]imidazol-6-yl)-5-(1-(tetrahydro-2H-pyran-4-yl)-1H-pyrazol-5-yl)pyrrolo[2,1-f][1,2,4]triazin-4-amine (46); 7-(1-((2,2-difluorocyclopropyl) methyl)-1H-indazol-6-yl)-5-(1-(tetrahydro-2H-pyran-4-yl)-1H-1,2,3-triazol-5-yl)pyrrolo [2,1-f][1,2,4]triazin-4-amine (47); 7-(1-((2,2-difluorocyclopropyl) methyl)-1H-indazol-6-yl)-5-(1-(tetrahydro-2H-pyran-4-yl)-1H-pyrazol-5-yl)pyrrolo[2,1-f][1,2,4] triazin-4-amine (48); 1-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)-3-fluoropropan-2-ol (49); 1-(6-(4-amino-5-(1-(tetrahydro-2H-pyran-4-yl)-1H-1,2,3-triazol-5-yl)pyrrolo[2,1-f][1,2,4]triazin-7-yl)-1H-indazol-1-yl)-3-fluoropropan-2-ol (50); 2-(6-(4-amino-5-(1-(tetrahydro-2H-pyran-4-yl)-1H-pyrazol-5-yl) pyrrolo[2,1-f][1,2,4]triazin-7-yl)-1H-indazol-1-yl)-N,N-dimethylacetamide (51); (R)-5-((6-(4-amino-5-(1-(tetrahydro-2H-pyran-4-yl)-1H-pyrazol-5-yl)pyrrolo[2,1-f][1,2,4]triazin-7-yl)-1H-indazol-1-yl) methyl)pyrrolidin-2-one (52); 7-(1-((5-methylisoxazol-3-yl) methyl)-1H-indazol-6-yl)-5-(1-(tetrahydro-2H-pyran-4-yl)-1H-pyrazol-5-yl)pyrrolo[2,1-f][1,2,4]triazin-4-amine (54); 2-(6-(4-amino-5-(1-(tetrahydro-2H-pyran-4-yl)-1H-pyrazol-5-yl) pyrrolo[2,1-f][1,2,4]triazin-7-yl)-1H-indazol-1-yl) benzamide (55); N-(2-(6-(4-amino-5-(1-(tetrahydro-2H-pyran-4-yl)-1H-pyrazol-5-yl)pyrrolo[2,1-f][1,2,4]triazin-7-yl)-1H-indazol-1-yl)phenyl)acetamide (56); 3-(6-(4-amino-5-(1-(tetrahydro-2H-pyran-4-yl)-1H-pyrazol-5-yl)pyrrolo [2,1-f][1,2,4]triazin-7-yl)-1H-indazol-1-yl)benzamide (57); 1-(4-(7-(4-amino-5-(1-(tetrahydro-2H-pyran-4-yl)-1H-1,2,3-triazol-5-yl)pyrrolo[2,1-f][1,2,4]triazin-7-yl) isoquinolin-1-yl)piperazin-1-yl)ethanone (58); 7-(1-morpholinoisoquinolin-7-yl)-5-(1-(tetrahydro-2H-pyran-4-yl)-1H-1,2,3-triazol-5-yl)pyrrolo[2,1-f][1,2,4]triazin-4-amine (59); 4-(7-(4-amino-5-(1-isopropyl-1H-1,2,3-triazol-5-yl)pyrrolo[2,1-f][1,2,4]triazin-7-yl) isoquinolin-1-yl)thiomorpholine 1,1-dioxide (60); 4-(7-(4-amino-5-(1-(tetrahydro-2H-pyran-4- yl)-1H-1,2,3-triazol-5-yl)pyrrolo[2,1-f][1,2,4]triazin-7-yl) isoquinolin-1-yl) thiomorpholine 1,1-dioxide (61); 7-(2-(piperazin-1-yl)pyridin-4-yl)-5-(1-(tetrahydro-2H-pyran-4-yl)-1H-pyrazol-5-yl)pyrrolo[2,1-f][1,2,4]triazin-4-amine (62); 7-(2-(4-(oxetan-3-yl)piperazin-1-yl)pyridin-4-yl)-5-(1-(tetrahydro-2H-pyran-4-yl)-1H-pyrazol-5-yl)pyrrolo[2,1-f][1,2,4]triazin-4-amine (63); 7-(2-(4-methylpiperazin-1-yl)pyridin-4-yl)-5-(1-(tetrahydro-2H-pyran-4-yl)-1H-pyrazol-5-yl)pyrrolo[2,1-f][1,2,4]triazin-4-amine (64); 1-(4-(4-(4-amino-5-(1-(tetrahydro-2H-pyran-4-yl)-1H-pyrazol-5-yl)pyrrolo[2,1-f][1,2,4]triazin-7-yl)pyridin-2-yl) piperazin-1-yl)ethanone (65); 2-(4-(4-amino-5-(1-(tetrahydro-2H-pyran-4-yl)-1H-pyrazol-5-yl)pyrrolo[2,1-f][1,2,4]triazin-7-yl)pyridin-2-yl)benzamide (66); 2-(5-(4-amino-5-(1-(tetrahydro-2H-pyran-4-yl)-1H-pyrazol-5-yl) pyrrolo[2,1-f][1,2,4]triazin-7-yl)pyridin-3-yl)benzamide (67); 7-(2-(2-(methylsulfonyl)phenyl)pyridin-4-yl)-5-(1-(tetrahydro-2H-pyran-4-yl)-1H-pyrazol-5-yl)pyrrolo[2,1-f][1,2,4]triazin-4-amine (68); 7-[1-(oxan-4-yl)-1H-indazol-6-yl]-5-[1-(propan-2-yl)-1H-pyrazol-4-yl]pyrrolo[2,1-f][1,2,4]triazin-4-amine (69); 4-(6-{4-amino-5-[1-(propan-2-yl)-1H-pyrazol-4-yl]pyrrolo[2,1-f]-9-[1,2,4]triazin-7-yl}-1H-indazol-1-yl)-1λ$^6$-thiane-1,1-dione (70); 5-(1-methyl-1H-pyrazol-4-yl)-7-[1-(oxan-4-yl)-1H-indazol-6-yl]pyrrolo[2,1-f][1,2,4]triazin-4-amine (71); 7-(1H-indazol-6-yl)-5-[1-(oxan-4-yl)-1H-pyrazol-5-yl]pyrrolo[2,1-f][1,2,4]triazin-4-amine (72); 4-amino-7-[1-(oxan-4-yl)-1H-indazol-6-yl]pyrrolo[2,1-f][1,2,4]triazine-5-carbonitrile (73); 4-{6-[4-amino-5-(1-methyl-1H-pyrazol-4-yl)pyrrolo[2,1-f][1,2,4]triazin-7-yl]-1H-indazol-1-yl}-1λ$^6$-thiane-1,1-dione (74); 5-iodo-7-[1-(oxan-4-yl)-1H-indazol-6-yl]pyrrolo[2,1-f][1,2,4]triazin-4-amine (75); 5-chloro-7-[1-(oxan-4-yl)-1H-indazol-6-yl]pyrrolo[2,1-f][1,2,4]triazin-4-amine (76); N-(5-{4-amino-7-[1-(oxan-4-yl)-1H-indazol-6-yl]pyrrolo[2,1-f][1,2,4]triazin-5-yl}pyridin-2-yl)acetamide (78); N-(5-{4-amino-7-[1-(1,1-dioxo-1λ$^6$-thian-4-yl)-1H-indazol-6-yl]pyrrolo[2,1-f][1,2,4]triazin-5-yl}pyridin-2-yl)acetamide (79); 2-(6-(4-amino-5-(1-(tetrahydro-2H-pyran-4-yl)-1H-pyrazol-5-yl) pyrrolo[2,1-f][1,2,4]triazin-7-yl)-1H-benzo[d]imidazol-1-yl)benzamide (80); 2-(6-(4-amino-5-(1-(tetrahydro-2H-pyran-4-yl)-1H-1,2,3-triazol-5-yl)pyrrolo[2,1-f][1,2,4]triazin-7-yl)-1H-benzo[d]imidazol-1-yl)benzamide (81); 7-(5-bromopyridin-3-yl)-5-[1-(oxan-4-yl)-1H-pyrazol-5-yl]pyrrolo[2,1-f][1,2,4]triazin-4-amine (82); 4-acetyl-1-(5-(4-amino-5-chloropyrrolo[2,1-f][1,2,4]triazin-7-yl)pyridin-3-yl)-3,3-dimethylpiperazin-2-one (83); 4-acetyl-1-(5-(4-amino-5-(1-(tetrahydro-2H-pyran-4-yl)-1H-pyrazol-5-yl)pyrrolo[2,1-f][1,2,4]triazin-7-yl)pyridin-3-yl)-3,3-dimethylpiperazin-2-one (84); (R)-4-acetyl-1-(4-(4-amino-5-(1-(1,1,1-trifluoropropan-2-yl)-1H-pyrazol-5-yl)pyrrolo[2,1-f][1,2,4]triazin-7-yl)pyridin-2-yl)-3,3-dimethylpiperazin-2-one (85); 1-(5-(4-amino-5-chloropyrrolo[2,1-f][1,2,4]triazin-7-yl) pyridin-3-yl)-4-(cyclopropanecarbonyl)-3,3-dimethylpiperazin-2-one (86); 1-(5-(4-amino-5-(1-(2,2,2-trifluoroethyl)-1H-pyrazol-5-yl) pyrrolo[2,1-f][1,2,4]triazin-7-yl)pyridin-3-yl)-4-(cyclopropanecarbonyl)-3,3-dimethylpiperazin-2-one (87); 4-acetyl-1-(5-(4-amino-5-(trifluoromethyl)pyrrolo[2,1-f][1,2,4]triazin-7-yl)pyridin-3-yl)-3,3-dimethylpiperazin-2-one (88); 1-(5-(4-amino-5-(1-(tetrahydro-2H-pyran-4-yl)-1H-pyrazol-5-yl)pyrrolo[2,1-f][1,2,4]triazin-7-yl)pyridin-3-yl)-4-(cyclopropanecarbonyl)-3,3-dimethylpiperazin-2-one (89); (R)-1-(4-(4-amino-5-(1-(1,1,1-trifluoropropan-2-yl)-1H-pyrazol-5-yl)pyrrolo[2,1-f][1,2,4]triazin-7-yl)pyridin-2-yl)-4-(cyclopropanecarbonyl)-3,3-dimethylpiperazin-2-one (90); (S)-4-acetyl-1-(5-(4-amino-5-chloropyrrolo[2,1-f][1,2,4]triazin-7-yl)pyridin-3-yl)-3,3,6-trimethylpiperazin-2-one (91); (S)-4-acetyl-1-(5-(4-amino-5-(trifluoromethyl)pyrrolo[2,1-f][1,2,4]triazin-7-yl)pyridin-3-yl)-3,3,6-trimethylpiperazin-2-one (92); (S)-4-acetyl-1-(4-(4-amino-5-(trifluoromethyl)pyrrolo[2,1-f][1,2,4]triazin-7-yl)pyridin-2-yl)-3,3,6-trimethylpiperazin-2-one (93); (S)-4-acetyl-1-(4-(4-amino-5-(1-methyl-1H-pyrazol-4-yl) pyrrolo[2,1-f][1,2,4]triazin-7-yl)pyridin-2-yl)-3,3,6-trimethylpiperazin-2-one (94); (R)-4-(5-(4-amino-5-chloropyrrolo[2,1-f][1,2,4]triazin-7-yl)-2-methylpyridin-3-yl)-2,2,6-trimethylmorpholin-3-one (95); S)-4-acetyl-1-(4-(4-amino-5-(1-(2,2,2-trifluoroethyl)-1H-pyrazol-5-yl)pyrrolo[2,1-f][1,2,4]triazin-7-yl)pyridin-2-yl)-3,3,6-trimethylpiperazin-2-one (96); (R)-4-(5-(4-amino-5-(1-(2,2,2-trifluoroethyl)-1H-pyrazol-5-yl)pyrrolo[2,1-f][1,2,4]triazin-7-yl)-2-methylpyridin-3-yl)-2,2,5-trimethylmorpholin-3-one (97); (S)-4-acetyl-1-(4-(4-amino-5-chloropyrrolo[2,1-f][1,2,4]triazin-7-yl)pyridin-2-yl)-3,3,6-trimethylpiperazin-2-one (98); (S)-4-(5-(4-amino-5-(trifluoromethyl)pyrrolo[2,1-f][1,2,4]triazin-7-yl)-2-methylpyridin-3-yl)-2,2,5-trimethylmorpholin-3-one (99); (R)-4-(5-(4-amino-5-chloro-6-fluoropyrrolo[2,1-f][1,2,4]triazin-7-yl)-2-methylpyridin-3-yl)-2,2,5-trimethylmorpholin-3-one (100); (R)-4-(5-(4-amino-5-(trifluoromethyl)pyrrolo[2,1-f][1,2,4]triazin-7-yl)-2-methylpyridin-3-yl)-2,2,5-trimethylmorpholin-3-one (101); (S)-4-acetyl-1-(5-(4-amino-5-(1-methyl-1H-pyrazol-4-yl)pyrrolo[2,1-f][1,2,4]triazin-7-yl)pyridin-3-yl)-3,3,6-trimethylpiperazin-2-one (102); (S)-4-(5-(4-amino-5-(trifluoromethyl)pyrrolo[2,1-f][1,2,4]triazin-7-yl)-2-methylpyridin-3-yl)-2,2,6-trimethylmorpholin-3-one (103); ((S)-4-acetyl-1-(5-(4-amino-5-(1-(2,2,2-trifluoroethyl)-1H-pyrazol-5-yl)pyrrolo[2,1-f][1,2,4]triazin-7-yl) pyridin-3-yl)-3,3,6-trimethylpiperazin-2-one (104); (S)-4-(5-(4-amino-5-(1-(2,2,2-trifluoroethyl)-1H-pyrazol-5-yl)pyrrolo[2,1-f][1,2,4]triazin-7-yl)-2-methylpyridin-3-yl)-2,2,5-trimethylmorpholin-3-one (105); (S)-4-acetyl-1-(6-(4-amino-5-chloropyrrolo[2,1-f][1,2,4]triazin-7-yl)pyridin-2-yl)-3,3,6-trimethylpiperazin-2-one (106); (S)-4-(5-(4-amino-5-(1-(2,2,2-trifluoroethyl)-1H-pyrazol-5-yl)pyrrolo[2,1-f][1,2,4]triazin-7-yl)-2-methylpyridin-3-yl)-2,2,6-trimethylmorpholin-3-one (107); (S)-4-acetyl-1-(6-(4-amino-5-(1-(2,2,2-trifluoroethyl)-1H-pyrazol-5-yl)pyrrolo[2,1-f][1,2,4]triazin-7-yl)pyridin-2-yl)-3,3,6-trimethylpiperazin-2-one (108); (S)-7-(6-(4-acetyl-3,3,6-trimethyl-2-oxopiperazin-1-yl)pyridin-2-yl)-4-aminopyrrolo[2,1-f][1,2,4]triazine-5-carbonitrile (109); (S)-4-acetyl-1-(6-(4-amino-5-(1-methyl-1H-pyrazol-4-yl)pyrrolo[2,1-f][1,2,4]triazin-7-yl)pyridin-2-yl)-3,3,6-trimethylpiperazin-2-one (110); (S)-4-acetyl-1-(6-(4-amino-5-(trifluoromethyl) pyrrolo[2,1-f][1,2,4]triazin-7-yl)pyridin-2-yl)-3,3,6-trimethylpiperazin-2-one (111); (S)-4-(4-(4-amino-5-(1-(2,2,2-trifluoroethyl)-1H-pyrazol-5-yl)pyrrolo[2,1-f][1,2,4]triazin-7-yl) pyridin-2-yl)-2,2,5-trimethylmorpholin-3-one (112); (4-(4-amino-5-(trifluoromethyl) pyrrolo[2,1-f][1,2,4]triazin-7-yl) morpholin-2-yl)(pyrrolidin-1-yl)methanone (113); 4-(4-amino-5-(trifluoromethyl)pyrrolo[2,1-f][1,2,4]triazin-7-yl)-N-isopropylmorpholine-2-carboxamide (114); 4-(4-amino-5-(trifluoromethyl)pyrrolo[2,1-f][1,2,4]triazin-7-yl)-N-cyclohexylmorpholine-2-carboxamide (115); 1-(4-amino-5-(trifluoromethyl)pyrrolo[2,1-f][1,2,4]triazin-7-yl)-N-cyclopentylpiperidine-3-carboxamide (116); 1-(4-amino-5-(trifluoromethyl)pyrrolo[2,1-f][1,2,4]triazin-7-yl)-N,N-dimethylpiperidine-3-carboxamide (117); 1-(4-amino-5-(trifluoromethyl)pyrrolo[2,1-f][1,2,4]triazin-7-yl)-N-phenylpiperidine-3-carboxamide (118); and 1-(4-amino-5-(trifluoromethyl)pyrrolo[2,1-f][1,2,4]triazin-7-yl)-N-isopropylpiperidine-3-carboxamide (119).

8. A pharmaceutical composition comprising one or more compounds according to claim 1 and a pharmaceutically acceptable carrier or diluent.

9. A method of treating a disease, comprising administering to a patient a therapeutically-effective amount of a compound according to claim 1, wherein the disease is inflammatory or autoimmune disease.

10. The method according to claim 9, wherein said autoimmune disease or chronic inflammatory disease is systemic lupus erythematosus, lupus nephritis, rheumatoid arthritis, multiple vasculitides, idiopathic thrombocytopenic purpura, myasthenia gravis, allergic rhinitis, or multiple sclerosis.

* * * * *

UNITED STATES PATENT AND TRADEMARK OFFICE
CERTIFICATE OF CORRECTION

PATENT NO. : 10,023,576 B2
APPLICATION NO. : 15/521199
DATED : July 17, 2018
INVENTOR(S) : Rajeev S. Bhide et al.

Page 1 of 2

It is certified that error appears in the above-identified patent and that said Letters Patent is hereby corrected as shown below:

In the Claims

Column 128, Lines 5-13, Claim 1, delete " 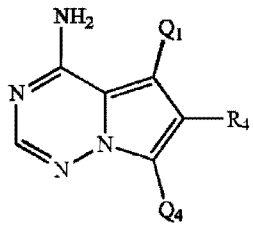 " and insert -- 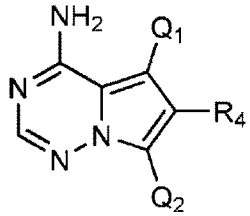 --, therefor.

Column 129 (Structure), Lines 45-55, Claim 6, delete " 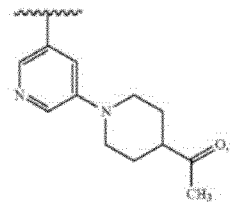 " and insert -- 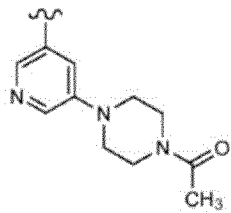 --, therefor.

Signed and Sealed this
Twelfth Day of February, 2019

Andrei Iancu
*Director of the United States Patent and Trademark Office*

Column 134, Line 50 (Approximately), Claim 7, delete "1-J][1" and insert -- 1-f][1 --, therefor.

Column 138, Line 10 (Approximately), Claim 7, delete "S)" and insert -- (S) --, therefor.